United States Patent
Meruelo et al.

(10) Patent No.: US 12,097,257 B2
(45) Date of Patent: Sep. 24, 2024

(54) INDUCTION AND ENHANCEMENT OF ANTITUMOR IMMUNITY INVOLVING SINDBIS VIRUS VECTORS EXPRESSING IMMUNE CHECKPOINT PROTEINS

(71) Applicant: NEW YORK UNIVERSITY, New York, NY (US)

(72) Inventors: Daniel Meruelo, Scarborough, NY (US); Alicia Hurtado Martinez, New York, NY (US); Christine Pampeno, New York, NY (US); Iris Scherwitzl, New York, NY (US)

(73) Assignee: New York University, New York, NY (US)

( * ) Notice: Subject to any disclaimer, the term of this patent is extended or adjusted under 35 U.S.C. 154(b) by 1052 days.

(21) Appl. No.: 16/977,290

(22) PCT Filed: Mar. 4, 2019

(86) PCT No.: PCT/US2019/020562
§ 371 (c)(1),
(2) Date: Sep. 1, 2020

(87) PCT Pub. No.: WO2019/173223
PCT Pub. Date: Sep. 12, 2019

(65) Prior Publication Data
US 2021/0000946 A1  Jan. 7, 2021

Related U.S. Application Data

(60) Provisional application No. 62/638,773, filed on Mar. 5, 2018, provisional application No. 62/725,802, filed on Aug. 31, 2018.

(51) Int. Cl.
| | | |
|---|---|---|
| *A61K 39/39* | (2006.01) | |
| *A61K 39/00* | (2006.01) | |
| *A61P 35/00* | (2006.01) | |
| *C07K 14/47* | (2006.01) | |
| *C07K 14/705* | (2006.01) | |
| *C12N 7/00* | (2006.01) | |

(52) U.S. Cl.
CPC .......... *A61K 39/39* (2013.01); *A61K 39/0011* (2013.01); *A61P 35/00* (2018.01); *C07K 14/4748* (2013.01); *C07K 14/70521* (2013.01); *C07K 14/70575* (2013.01); *C07K 14/70578* (2013.01); *C12N 7/00* (2013.01); *A61K 2039/5256* (2013.01); *C07K 2319/055* (2013.01); *C07K 2319/30* (2013.01); *C12N 2770/36132* (2013.01); *C12N 2770/36143* (2013.01)

(58) Field of Classification Search
None
See application file for complete search history.

(56) References Cited

U.S. PATENT DOCUMENTS

| | | |
|---|---|---|
| 4,946,778 A | 8/1990 | Ladner et al. |
| 5,399,346 A | 3/1995 | Anderson et al. |
| 6,432,699 B1 | 8/2002 | Meruelo et al. |
| 7,303,898 B2 | 12/2007 | Hurtado et al. |
| 7,306,792 B2 | 12/2007 | Meruelo |
| 8,084,026 B2 | 12/2011 | Glaser et al. |
| 8,093,021 B2 | 1/2012 | Hurtado et al. |
| 8,178,346 B2 | 5/2012 | Mancebo et al. |
| 8,282,916 B2 | 10/2012 | Meruelo et al. |
| 8,530,232 B2 | 9/2013 | Hurtado et al. |
| 9,423,401 B2 | 8/2016 | Varki et al. |
| 2015/0017194 A1 | 1/2015 | Akahata et al. |
| 2016/0000843 A1 | 1/2016 | Lowe et al. |
| 2016/0008431 A1 | 1/2016 | Meruelo et al. |
| 2016/0264643 A1 | 9/2016 | Lazar et al. |
| 2017/0233450 A1 | 8/2017 | Akahata et al. |
| 2018/0000912 A1 | 1/2018 | Meruelo et al. |
| 2020/0377598 A1 | 12/2020 | Meruelo et al. |

FOREIGN PATENT DOCUMENTS

| | | |
|---|---|---|
| CA | 2337905 A1 * | 3/2000 |
| WO | WO 2002/094994 | 11/2002 |
| WO | WO 2015/035213 | 3/2015 |

(Continued)

OTHER PUBLICATIONS

Jonas, B.A., "Combination of an oncolytic virus with PD-L1 blockade keeps cancer in check", Science Translational Medicine, Apr. 19, 2017, vol. 9, Issue 386, p. 2781.

Tanque, K., et al., "Armed Oncolytic Adenovirus-Expressing PD-L1 Mini-Body Enhances Antitumor Effects of Chimeric Antigen Receptor T Cells in Solid Tumors", Cancer Research, Feb. 24, 2017, vol. 77, Issue 8, pp. 2040-2051.

Aarnoudse et al., "Interleukin-2-induced, Melanoma-Specific T Cells Recognize Camel, an Unexpected Translation Product of LAGE-1," Int J Cancer., 1999, 82(3):442-8.

(Continued)

*Primary Examiner* — Nicole Kinsey White
(74) *Attorney, Agent, or Firm* — Hodgson Russ LLP

(57) ABSTRACT

Provided are polynucleotides and viral vectors, particularly, *Alphavirus* vectors such as Sindbis viral vectors, which encode an immune checkpoint protein, or a ligand binding portion of the checkpoint protein, or an immune checkpoint protein or ligand binding portion thereof fused to one or more immunoglobulin (Ig) domains, e.g., an Ig hinge region and an Ig heavy chain constant domain. Methods of treating a mammalian subject having a cancer or tumor are provided, in which the viral vectors, e.g., a Sindbis virus vector, encoding the immune checkpoint protein, a ligand binding portion thereof, or a checkpoint protein fusion protein as described, are administered to the subject, resulting in an anti-cancer or anti-tumor immune response, significant reduction in tumor growth in the treated subject and increased survivability.

12 Claims, 12 Drawing Sheets

Specification includes a Sequence Listing.

(56) References Cited

FOREIGN PATENT DOCUMENTS

| WO | WO 2016/149643 | 9/2016 |
|---|---|---|
| WO | 2017152042 A2 | 9/2017 |
| WO | WO 2017/152042 | 9/2017 |
| WO | 2018023025 A1 | 2/2018 |
| WO | WO 2018/161092 | 9/2018 |

OTHER PUBLICATIONS

Adair et al. "The TAG Family of Cancer/Testis Antigens Is Widely Expressed in a Variety of Malignancies and Gives Rise to HLA-A2-restricted Epitopes," J Immunother., 2008, 31(1):7-17.
Albershardt et al., "LV305, a dendritic cell-targeting integration-deficient ZVex TM-based lentiviral vector encoding NY-ESO-1, induces potent anti-tumor immune response," Molecular Therapy Oncolytics, 2016, 3(16010): 11 pages.
Albershardt et al., "LV305, a dendritic cell-targeting integration-deficient ZVex™-based lentiviral vector encoding NY-ESO-1, induces potent anti-tumor immune response," Molecular Therapy—Oncolytics, 2016, 3:16010, XP055373918.
Alexander, J. et al., "Development of High Potency Universal DR-restricted Helper Epitopes by Modification of High Affinity DR-blocking Peptides," Immunity, 1994, 1(9): 751-761.
Alisa et al., "Analysis of CD4+ T-Cell Responses to a Novel Alpha-Fetoprotein-Derived Epitope in Hepatocellular Carcinoma Patients," Clin. Cancer Res., 2005, 11(18):6686-94.
Altman, J.D. et al., "Phenotypic Analysis of Antigen-Specific T Lymphocytes," Science, 1996, 274(5284):94-96.
Andersen et al., "Identification of a Cyclin B1-derived CTL Epitope Eliciting Spontaneous Responses in Both Cancer Patients and Healthy Donors," Cancer Immunol Immunother, 2011, 60(2):227-34.
Anderson et al., "Endogenously Synthesized Peptide With an Endoplasmic Reticulum Signal Sequence Sensitizes Antigen Processing Mutant Cells to Class I-restricted Cell-Mediated Lysis," J Exp Med., 1991, 174(2):489-492.
Anderson et al., "Identification of MAGE-C1 (CT-7) Epitopes for T-cell Therapy of Multiple Myeloma," Cancer Immunol Immunother, 2011, 60(7):985-97.
Anderson, "Prospects for Human Gene Therapy," Science, 1984, 226(4673):401-409.
Andtbacka et al., "Talimogene Laherparepvec Improves Durable Response Rate in Patients With Advanced Melanoma," J Clin Oneal, 2015, 33(25):2780-2788.
Asai et al., "In Vitro Generated Cytolytic T Lymphocytes Reactive Against Head and Neck Cancer Recognize Multiple Epitopes Presented by HLA-A2, Including Peptides Derived From the p53 and MDM-2 Proteins," Cancer Immun., Apr. 16, 2002, 2(3): 17 pages.
Asemissen et al., "Identification of a Highly Immunogenic HLA-A*01-binding T Cell Epitope of WT1," Clin. Cancer Res., 2006, 12(24):7476-82.
Aurisicchio et al., "A Novel Minigene Scaffold for Therapeutic Cancer Vaccines," Oncoimmunology, Oct. 27, 2014, 3(e27529): 14 pages.
Ayyoub et al., "An Immunodominant SSX-2-derived Epitope Recognized by CD4+ T Cells in Association With HLA-DR," J Clin Invest., 2004, 113(8):1225-33.
Ayyoub et al., "Assessment of Vaccine-Induced CD4 T Cell Responses to the 119-143 Immunodominant Region of the Tumor-Specific Antigen NY-ESO-1 Using DRB1*0101 Tetramers," Clin Cancer Res., 2010, 16(18):4607-15.
Ayyoub et al., "CD4+ T Cell Responses to SSX-4 in Melanoma Patients, " J Immunol., 2005, 174(8):5092-9.
Ayyoub et al., "Distinct but Overlapping T Helper Epitopes in the 37-58 Region of SSX-2," Clin Immunol., 2005, 114(1):70-8.
Ayyoub et al., "Identification of an SSX-2 Epitope Presented by Dendritic Cells to Circulating Autologous CD4+ T Cells," J Immunol., 2004, 172(11):7206-11.

Ayyoub et al., "Proteasome-assisted Identification of a SSX-2-derived Epitope Recognized by Tumor-Reactive CTL Infiltrating Metastatic Melanoma," J Immunol., 2002, 168(4):1717-22.
Backert et al., "Immunoinformatics and Epitope Prediction in the Age of Genomic Medicine," Genome Medicine, 2015, 7(119): 12 pages.
Bagnoli et al., "A Step Further in Understanding the Biology of the Folate Receptor in Ovarian Carcinoma," Gynecol. Oncol., 2003, 88:S140-4.
Bakker et al., "Identification of a Novel Peptide Derived From the Melanocyte-Specific gp100 Antigen as the Dominant Epitope Recognized by an HLA-A2.1-restricted Anti-Melanoma CTL Line," Int J Cancer., 1995, 62(1):97-102.
Bast et al., "CA 125 and the Detection of Recurrent Ovarian Cancer: A Reasonably Accurate Biomarker for a Difficult Disease," Cancer, 2010, 116(12):2850-2853.
Bast et al., "Monitoring Human Ovarian Carcinoma With a Combination of CA 125, CA 19-9, and Carcinoembryonic Antigen," Am. J. Obstet. Gynecol., 1984, 149(5):553-9.
Baurain et al., "High Frequency of Autologous Anti-Melanoma CTL Directed Against an Antigen Generated by a Point Mutation in a New Helicase Gene," J. Immunol., 2000, 164(11):6057-66.
Bei et al., "TAA polywpitope DNA-based vaccines: a potential tool for cancer therapy," Journal of Biomedicine and Biotechnology, Jan. 2010, 2010: 12 pages.
Bellone et al., "Induction of Human Tumor-Associated Differentially Expressed gene-12 (TADG-12/TMPRSS3)-specific Cytotoxic T Lymphocytes in Human Lymphocyte antigen-A2.1-positive Healthy Donors and Patients With Advanced Ovarian Cancer," Cancer, 2009, 115(4):800-811.
Benlalam et al., "Identification of Five New HLA-B*3501-restricted Epitopes Derived From Common Melanoma-Associated Antigens, Spontaneously Recognized by Tumor-Infiltrating Lymphocytes," J. Immunol., 2003, 171:(11):6283-6289.
Benton et al., "Screening Lambdagt Recombinant Clones by Hybridization to Single Plaques in Situ," Science, 1977, 196(4286):180-182.
Bertino et al., "The Immune System in Hepatocellular Carcinoma and Potential New Immunotherapeutic Strategies," Biomed. Res. Int., 2015, 2015(731469): 13 pages.
Bilsborough et al., "A MAGE-3 Peptide Presented by HLA-B44 Is Also Recognized by Cytolytic T Lymphocytes on HLA-B18, " Tissue Antigens, 2002, 60(1):16-24.
Bioley et al., "Vaccination With Recombinant NY-ESO-1 Protein Elicits Immunodominant HLA-DR52b-restricted CD4+ T Cell Responses With a Conserved T Cell Receptor Repertoire," Clin Cancer Res., 2009, 15(13): 4467-74.
Bloomer et al., "Highly Efficient and Sustained Gene Transfer in Adult Neurons With a Lentivirus Vector," J. Virol., 1997, 71(9):6641-6649.
Boel et al., "BAGE: A New Gene Encoding an Antigen Recognized on Human Melanomas by Cytolytic T Lymphocytes," Immunity, 1995, 2(2): 167-75.
Bosch et al., "Recognition of BCR-ABL Positive Leukemic Blasts by Human CD4+ T Cells Elicited by Primary in Vitro Immunization With a BCR-ABL Breakpoint Peptide," Blood, 1996, 88(9):3522-7.
Breckpot et al., "Identification of New Antigenic Peptide Presented by HLA-Cw7 and Encoded by Several MAGE Genes Using Dendritic Cells Transduced With Lentiviruses," J Immunol, 2004, 172(4):2232-7.
Breckpot et al., "Lentiviral Vectors for Cancer Immunotherapy: Transforming Infectious Particles Into Therapeutics," Gene Ther., 2007, 14(11):847-862.
Bredenbeek et al., "Sindbis Virus Expression Vectors: Packaging of RNA Replicons by Using Defective Helper RNAs," Journal od Virology, Nov. 1993, 67(11):6439-6446.
Brichard et al., "A Tyrosinase Nonapeptide Presented by HLA-B44 Is Recognized on a Human Melanoma by Autologous Cytolytic T Lymphocytes," Eur. J. Immunol., 1996, 26(1):224-30.
Brigham et al., "In Vivo Transfection of Murine Lungs With a Functioning Prokaryotic Gene Using a Liposome Vehicle," Am. J. Med .. Sci., 1989, 298(4):278-81.

(56) References Cited

OTHER PUBLICATIONS

Bright et al., "Overexpressed Oncogenic Tumor-Self Antigens," Hum Vaccin. Immunother., 2014, 10(11):3297-3305.

Brossart et al., "Her-2/neu-derived Peptides Are Tumor-Associated Antigens Expressed by Human Renal Cell and Colon Carcinoma Lines and Are Recognized by in Vitro Induced Specific Cytotoxic T Lymphocytes," Cancer Res., 1998, 58(4): 732-6.

Brossart et al., "Identification of HLA-A2-restricted T-cell Epitopes Derived From the MUC1 Tumor Antigen for Broadly Applicable Vaccine Therapies," Blood, 1999, 93(12):4309-4317.

Butterfield et al., "Generation of Human T-cell Responses to an HLA-A2.1-restricted Peptide Epitope Derived From Alpha-Fetoprotein," Cancer Res., 1999, 59(13):3134-42.

Campi et al., "CD4(+) T Cells From Healthy Subjects and Colon Cancer Patients Recognize a Carcinoembryonic Antigen-Specific Immunodominant Epitope," Cancer Res., 2003, 63(23):8481-6.

Cancer Medicine, 6th ed., Kufe et al. (ed)., 2003 Section 2: Cancer Immunology, Chapter 12: Tumor Antigens, 18 pages.

cancerimmunitv.org [online], "T cell-defined tumor antigens," available on or before Oct. 20, 2013, via Internet Archive: Wayback Machine URL <https://web.archive.org/web/20131020055211/http://www.cancerimmunity.org/peptide//>, retrieved on Jul. 8, 2020, URL <http://www.cancerimmunity.org/peptide//>, 4 pages.

Castelli et al., "Novel HLA-Cw8-restricted T Cell Epitopes Derived From Tyrosinase-Related protein-2 and gp100 Melanoma Antigens, " J. Immunol., 1999, 162(3): 1739-48.

Castle et al., "Immunomic, Genomic and Transcriptomic Characterization of CT26 Colorectal Carcinoma," BMC Genomics, 2014, 15(190): 12 pages.

Cayouette et al., "Adenovirus-mediated Gene Transfer of Ciliary Neurotrophic Factor Can Prevent Photoreceptor Degeneration in the Retinal Degeneration (Rd) Mouse," Human Gene Therapy, 1997, 8(4):423-430.

Cesson et al., "MAGE-A3 and MAGE-A4 Specific CD4(+) T Cells in Head and Neck Cancer Patients: Detection of Naturally Acquired Responses and Identification of New Epitopes," Cancer Immunol Immunother., 60(1):23-35.

Chang et al., "Peptide Length-Based Prediction of peptide-MHC Class II Binding," Bioinformatics, 2006, 22(22):2761-2767.

Chaux et al., "A Mage-1 Peptide Recognized on HLA-DR15 by CD4(+) T Cells, " Eur J Immunol., 2001, 31(6):1910-6.

Chaux et al., "Identification of Five MAGE-A1 Epitopes Recognized by Cytolytic T Lymphocytes Obtained by in Vitro Stimulation With Dendritic Cells Transduced With MAGE-A1," J Immunol., 1999, 163(5):2928-36.

Chaux et al., "Identification of Mage-3 Epitopes Presented by HLA-DR Molecules to CD4(+) T Lymphocytes, " J Exp Med., 1999, 189(5):767-78.

Cheever et al., "The Prioritization of Cancer Antigens: A National Cancer Institute Pilot Project for the Acceleration of Translational Research," Clin Cancer Res., 2009, 15(17):5323-5337.

Chekmasova et al., "Successful Eradication of Established Peritoneal Ovarian Tumors in SCID-Beige Mice Following Adoptive Transfer of T Cells Genetically Targeted to the MUC16 Antigen," Clin. Cancer Res., 2010, 16(14):3594-606.

Chen et al., "Immunodominant CD4+ Responses Identified in a Patient Vaccinated With Full-Length NY-ESO-1 Formulated With ISCOMATRIX Adjuvant," Proc Natl Acad Sci USA., 2004, 101(25):9363-8.

Chen et al., "Identification of NY-ESO-1 Peptide Analogues Capable of Improved Stimulation of Tumor-Reactive CTL," J Immunol., 2000, 165(2):948-55.

Chester et al., "Immunotherapeutic Approaches to Ovarian Cancer Treatment," J Immunother., 2015, Cancer 3(7): 10 pages.

Chiari et al., "Two Antigens Recognized by Autologous Cytolytic T Lymphocytes on a Melanoma Result From a Single Point Mutation in an Essential Housekeeping Gene," Cancer Res., 1999, 59(22):5785-92.

Chiriva-Inernati et al., "Sperm Protein 17 Is a Suitable Target for Adoptive T-cell-based Immunotherapy in Human Ovarian Cancer," J. Immunother., 2008, 31(8):693-703.

Chiriva-Internati et al., "Identification of a Sperm Protein 17 CTL Epitope Restricted by HLA-A1," Int J Cancer, 2003, 107(5):863-5.

Cole et al., "The EBV-hybridoma technique and its application to human lung cancer," Paper, Presentated at Monoclonal Antibodies and Cancer Therapy, Jan. 26- Feb. 2, 1985, 12 pages.

Consogno et al., "Identification of Immunodominant Regions Among Promiscuous HLA-DR-restricted CD4+ T-cell Epitopes on the Tumor Antigen MAGE-3," Blood., 2003, 101(3):1038-44.

Corbiere et al., "Antigen Spreading Contributes to MAGE Vaccination-Induced Regression of Melanoma Metastases," Cancer Res., 2011, 71(4): 1253-62.

Corbiere et al., "Identification of a MAGE-1 Peptide Recognized by Cytolytic T Lymphocytes on HLA-B*5701 Tumors," Tissue Antigens, 2004, 63(5):453-7.

Cornetta et al., "Gene Transfer Into Primates and Prospects for Gene Therapy in Humans," Prog. Nucleic. Acid Research and Molecular Biology, 1989, 36:311-322.

Correale et al., "In Vitro Generation of Human Cytotoxic T Lymphocytes Specific for Peptides Derived From Prostate-Specific Antigen," J Natl. Cancer Inst., 1997, 89(4):293-300.

Coulie et al., "A Mutated Intron Sequence Codes for an Antigenic Peptide Recognized by Cytolytic T Lymphocytes on a Human Melanoma," Proc. Natl. Acad. Sci. U.S.A., 1995, 92(17):7976-80.

Cox et al., "Identification of a Peptide Recognized by Five Melanoma-Specific Human Cytotoxic T Cell Lines," Science, 1994, 264(5159):716-719.

Criscitiello, "Tumor-associated Antigens in Breast Cancer," Breast Care, 2012, 7(4):262-266.

Crosti et al., "Identification of Novel Subdominant Epitopes on the Carcinoembryonic Antigen Recognized by CD4+ T Cells of Lung Cancer Patients," J Immunol., 2006, 176(8):5093-9.

Dalet et al., "An Antigenic Peptide Produced by Reverse Splicing and Double Asparagine Deamidation," Proc. Natl. Acad. Sci., U.S.A., 2011, 108(29):E323-31.

De Backer et al., "Characterization of the GAGE Genes That Are Expressed in Various Human Cancers and in Normal Testis," Cancer Res., 1999, 59(13):3157-65.

Di Modugno et al., "Human Mena Protein, a Serex-Defined Antigen Overexpressed in Breast Cancer Eliciting Both Humoral and CD8+ T-cell Immune Response," Int. J Cancer, 2004, 109(6):909-18.

Ding et al., "Activation of CD4+ T cells by delivery of the B7 costimulatory signal on bystander antigen-presenting cells (trans-costimulation)," European Journal of Immunology, 1994, 24(4):859-866.

Djenidi et al., "CD8+CD103+ Tumor-Infiltrating Lymphocytes Are Tumor-Specific Tissue-Resident Memory T Cells and a Prognostic Factor for Survival in Lung Cancer Patients," J Immunol., 2015, 194(7):3475-3486.

Duffour et al., "A MAGE-A4 Peptide Presented by HLA-A2 Is Recognized by Cytolytic T Lymphocytes," Eur J Immunol., 1999, 29(10):3329-37.

Duffy, "Carcinoembryonic Antigen as a Marker for Colorectal Cancer: Is It Clinically Useful?," Clin. Chem., 2001, 47(4):624-30.

Ebert et al., "A Long, Naturally Presented Immunodominant Epitope From NY-ESO-1 Tumor Antigen: Implications for Cancer Vaccine Design," Cancer Res., 2009, 69(3):1046-54.

Echchakir et al., "A Point Mutation in the alpha-actinin-4 Gene Generates an Antigenic Peptide Recognized by Autologous Cytolytic T Lymphocytes on a Human Lung Carcinoma," Cancer Res., 2001, 61(10):4078-83.

Eglitis et al., "Retroviral Vectors for Introduction of Genes Into Mammalian Cells," Biotechniques, 1988, 6(7):608-614.

Eikawa et al., "Induction of CD8 T-cell Responses Restricted to Multiple HLA Class I Alleles in a Cancer Patient by Immunization With a 20-mer NY-ESO-If (NY-ESO-1 91-110) Peptide," Int J Cancer, 2013, 132(2):345-54.

El Hage et al., "Preprocalcitonin Signal Peptide Generates a Cytotoxic T Lymphocyte-Defined Tumor Epitope Processed by a Proteasome-Independent Pathway," Proc. Natl. Acad. Sci. U.S.A., 2008, 105(29):10119-24.

(56) References Cited

OTHER PUBLICATIONS

Enamorado et al., "Enhanced anti-tumor immunity requires the interplay between resident and circulating memory CD8+ T Cell," Nat Commun, Jul. 17, 2017, 8(6073): 11 pages.
EP Extended Search Report in Euroepean Appln. No. 18717142.6, dated Sep. 27, 2019.
EP Office Action in European Appln. No. 18717142.6, dated Jul. 28, 2021, 9 pages.
Facciabene et al., "DNA and Adenoviral Vectors Encoding Carcinoembryonic Antigen Fused to Immunoenhancing Sequences Augment Antigen-Specific Immune Response and Confer Tumor Protection," Hum Gene Ther., 2006, 17(1):81-92.
Facciabene et al., "Vectors Encoding Carcinoembryonic Antigen Fused to the B Subunit of Heat-Labile Enterotoxin Elicit Antigen-Specific Immune Responses and Antitumor Effects," Vaccine, 2007, 26:47-58.
Felgner et al., "Lipofection: A Highly Efficient, Lipid-Mediated DNA-transfection Procedure," Proc. Natl. Acad. Sci., 1987, 84(21):7413.
Fikes et al., "Design of multi-epitope, analogue-bassed cancer vaccines," Expert Opinion on Biological Therapy, Jan. 1, 2003, 3(6):985-993.
Fisk et , "Identification of an Immunodominant Peptide of HER-2/neu Protooncogene Recognized by Ovarian Tumor-Specific Cytotoxic T Lymphocyte Lines," J Exp Med., 1995, 181(6):2109-17.
Foks et al., "Immune checkpoint proteins: exploring their therapeutic potential to regulate atherosclerosis," British Journal of Pharmacology, 2017, 174(22):3940-3955.
Fossum et al., "Overlapping Epitopes Encompassing a Point Mutation (12 Gly-->Arg) in p21 Ras Can Be Recognized by HLA-DR, -DP and -DQ Restricted T Cells," J Immunol., 1993, 23(10):2687-2691.
Friedman, "Progress Toward Human Gene Therapy," Science, 1989, 244(4910):1275-1281.
Fuertes et al., "Host Type I IFN Signals Are Required for Antitumor CD8+ T Cell Responses Through CD8{alpha}+ Dendritic Cells," J Exp Med, 2011,208(10):2005-2016.
Fujiki et al., "Identification and Characterization of a WT1 (Wilms Tumor Gene) Protein-Derived HLA-DRB1*0405-restricted 16-mer Helper Peptide That Promotes the Induction and Activation of WT1-specific Cytotoxic T Lymphocytes," J. Immunother., 2007, 30(3):282-93.
Fukuyama et al., "Identification of a New Cancer/Germline Gene, KK-LC-1, Encoding an Antigen Recognized by Autologous CTL Induced on Human Lung Adenocarcinoma," Cancer Res., 2006, 66(9):4922-8.
Galanis et al., "Phase I Trial of Intraperitoneal Administration of an Oncolytic Measles Virus Strain Engineered to Express Carcinoembryonic Antigen for Recurrent Ovarian Cancer," Cancer Res., 2010, 70(3):875-82.
Gambacorti-Passerini et al., "Human CD4 Lymphocytes Specifically Recognize a Peptide Representing the Fusion Region of the Hybrid Protein pml/RAR Alpha Present in Acute Promyelocytic Leukemia Cells," Blood., 1993, 81(5):1369-75.
Garoff et al., "The Signal Sequence of the p62 Protein of Semliki Forest Virus Is Involved in Initiation but Not in Completing Chain Translocation," J Cell. Biol., 1990, 111(3):867-876.
Garon et al., "Pembrolizumab for the Treatment of Non-Small-Cell Lung Cancer," N Engl J Med, 2015, 372(21):2018-2028.
Gastl et al., "Ep-CAM Overexpression in Breast Cancer as a Predictor of Survival," Lancet, 2000, 356(9246):1981-2.
Gaudin et al., "A hsp70-2 Mutation Recognized by CTL on a Human Renal Cell Carcinoma," J. Immunol., 1999, 162(3):1730-8.
Gaugler et al., "Human Gene MAGE-3 Codes for an Antigen Recognized on a Melanoma by Autologous Cytolytic T Lymphocytes," J Exp Med., 1994, 179(3):921-30.
GenBank Accession No. AK155610.1, "Mus musculus B6-derived CD11 +ve dendritic cells cDNA, RIKEN full-length enriched library, clone:F730022K13 product:tumor necrosis factor (ligand) superfamily, member 9, full insert sequence," dated Oct. 6, 2010, 4 pages.

GenBank Accession No. BC104807.1, "*Homo sapiens* tumor necrosis factor (ligand) superfamily, member 9, mRNA (cDNA clone MGC:132467 IMAGE:8143810), complete cds," dated Jan. 19, 2006, 2 pages.
GenBank Accession No. NM_005018.2, "*Homo sapiens* programmed cell death 1 (PDCD1), mRNA," dated Sep. 15, 2016, 4 pages.
GenBank Accession No. NP_005009.2, "programmed cell death protein 1 precursor [*Homo sapiens*]," dated Sep. 15, 2016, 3 pages.
GenBank Accession No. P01857.1, "RecName: Full=Ig gamma-1 chain C region," dated Feb. 15, 2017, 8 pages.
Gjertsen et al., "Cytotoxic CD4+ and CD8+ T Lymphocytes, Generated by Mutant p21-ras (12Val) Peptide Vaccination of a Patient, Recognize 12Val-dependent Nested Epitopes Present Within the Vaccine Peptide and Kill Autologous Tumour Cells Carrying This Mutation," Int. J. Cancer, 72(5):784-90.
Gnjactic et al., "NY-ESO-1: Review of an Immunogenic Tumor Antigen," Immunotherapy of Cancer In: Advances in Cancer Research, 2006, 95:1-30.
Gnjatic et al., "NY-ESO-1: Review of an Immunogenic Tumor Antigen," Immunotherapy of Cancer In: Advances in Cancer Research, 2006, 95:1-30, XP008073732.
Gnjatic et al., "Strategy for monitoring T cell responses to NY_ESO-1 in patients with any HLA class I allele," Proceedings of the National Academy of Sciences of the United States of America, Sep. 26, 2000, 97(20):10917-10922.
Godelaine et al. "A New Tumor-Specific Antigen Encoded by MAGE-C2 and Presented to Cytolytic T Lymphocytes by HLA-B44," Cancer Immunol Immunother., 2007, 56(6):753-9.
Goodyear et al., "Dominant Responses With Conservation of T-cell Receptor Usage in the CD8+ T-cell Recognition of a Cancer Testis Antigen Peptide Presented Through HLA-Cw7 in Patients With Multiple Myeloma," Cancer Immunol Immunother., 2011, 60(12):1751-61.
Graf et al., "A Neoepitope Generated by an FLT3 Internal Tandem Duplication (FLT3-ITD) Is Recognized by Leukemia-Reactive Autologous CD8+ T Cells," Blood, 2007, 109(7):2985-8.
Granot et al., "Activation of Cytotoxic and Regulatory Functions of NK Cells by Sindbis Viral Vectors," PLoS One, 2011, 6(6):e20598, 14 pages.
Granot et al., "Sindbis Viral Vectors Transiently Deliver Tumor-Associated Antigens to Lymph Nodes and Elicit Diversified Antitumor CD8+ T-cell Immunity," Mol. Ther., 2014, 22(1):112-122.
Granot et al., "Sindbis Viral Vectors Transiently Deliver Tumor-associated Antigens to Lymph Nodes and Elicit Diversified Antitumor CD8+ T-cell Immunity," Molecular Therapy, 2014, 22(1):112-122, XP-002767391.
Granot et al., "The Role of Natural Killer Cells in Combinatorial Anti-Cancer Therapy Using Sindbis Viral Vectors and Irinotecan," Cancer Gene Ther., 2012, 19(8):588-591.
Grunstein et al., "Colony Hybridization: A Method for the Isolation of Cloned DNAs That Contain a Specific Gene," Proc. Nat Acad. Sci., USA, 1975, 72(10):3961-3975.
Guillaume et al., "Soluble MHC-peptide complexes: tools for the monitoring of T cell responses in clinical trials and basic research," Cancer Immunity, 2009, 9:7, 6 pages.
Guilloux et al., "A Peptide Recognized by Human Cytolytic T Lymphocytes on HLA-A2 Melanomas Is Encoded by an Intron Sequence of the N-acetylglucosaminyltransferase V Gene," J Exp Med., 1996, 183(3):1173-83.
Guo et al., "Direct Recognition and Lysis of Leukemia Cells by WT1-specific CD4+ T Lymphocytes in an HLA Class II-restricted Manner," Blood, 2005, 106(4): 1415-8.
Guo et al., "Editorial of the Special Issue: Oncolytic Viruses as a Novel Form of Immunotherapy for Cancer," Biomedicines, Aug. 24, 2017, 5(52): 5 pages.
Guo et al., "HLA-A2-restricted Cytotoxic T Lymphocyte Epitopes From Human Hepsin as Novel Targets for Prostate Cancer Immunotherapy," Scand J Immunol., 2013, 78(3):248-57.
Hanada et al., "Immune Recognition of a Human Renal Cancer Antigen Through Post-Translational Protein Splicing, " Nature, 2004, 427(6971):252-6.

(56) References Cited

OTHER PUBLICATIONS

Harvard.edu [online], "Tantigen: Tumor T cell Antigen Database," available on or before Sep. 5, 2016, via Internet Archive: Wayback Machine URL <https://web.archive.org/web/20160905170314/http://cvc.dfci.harvard.edu/tadb/> retrieved on Sep. 9, 2020, URL <http://cvc.dfci.harvard.edu/tadb/>, 1 page.

Hasegawa et al., "In Vitro Stimulation of CD8 and CD4 T Cells by Dendritic Cells Loaded With a Complex of Cholesterol-Bearing Hydrophobized Pullulan and NY-ESO-1 Protein: Identification of a New HLA-DR15-binding CD4 T-cell Epitope," Clin Cancer Res., 2006, 12(6): 1921-7.

Hassan et al., "Localization of Mesothelin in Epithelial Ovarian Cancer," Appl. Immunohistochem. Mol. Morphol., 2005, 13(3):243-7.

Heidecker et al., Cytolytic T Lymphocytes Raised Against a Human Bladder Carcinoma Recognize an Antigen Encoded by Gene MAGE-A12, J Immunol., 2000, 164(11):6041-5.

Helm et al., "Targeting c-MYC With T-cells," PLoS ONE, 2013, 8(10):e77375, 14 pages.

Herbst et al., "Predictive correlates of response to the anti-PD-L1 antibody MPDL3280A in cancer patients," Nature, 2014, 515(7528):563-567.

Herman et al., "A Peptide Encoded by the Human MAGE3 Gene and Presented by HLA-B44 Induces Cytolytic T Lymphocytes That Recognize Tumor Cells Expressing MAGE3," Immunogenetics, 1996, 43(6):377-83.

Hiltbold et al., "Naturally Processed Class II Epitope From the Tumor Antigen MUCI Primes Human CD4+ T Cells," Cancer Res., 1998, 58(22):5066-70.

Hogan et al., "The Peptide Recognized by HLA-A68.2-restricted, Squamous Cell Carcinoma of the Lung-Specific Cytotoxic T Lymphocytes Is Derived From a Mutated Elongation Factor 2 Gene," Cancer Res., 1998, 58(22):5144-50.

Holland's Cancer Medicine, 6th ed. BC Decker Inc., 2003, Zarour et al., "Tumor Antigens," Section 2, Chapter 12, 22 pages.

Hong et al., "Diverse Solid Tumors Expressing a Restricted Epitope of L1-CAM Can Be Targeted by Chimeric Antigen Receptor Redirected T Lymphocytes," J. Immunother., 2014, 37(2):93-104.

Horiguchi et al., "Screening of HLA-A24-restricted Epitope Peptides From Prostate-Specific Membrane Antigen That Induce Specific Antitumor Cytotoxic T Lymphocytes," Clin Cancer Res., 2002, 8(12):3885-92.

Horton et al., "Gene Splicing by Overlap Extension: Tailor-Made Genes Using the Polymerase Chain Reaction," BioTechniques, 1990, 8(5):528-535.

Huang et al., "Cytolytic T Lymphocytes Recognize an Antigen Encoded by MAGE-A10 on a Human Melanoma," J Immunol., 1999, 162(11):6849-54.

Huang et al., "T Cells Associated With Tumor Regression Recognize Frameshifted Products of the CDKN2A Tumor Suppressor Gene Locus and a Mutated HLA Class I Gene Product," J Immunol., 2004, 172(10):6057-64.

Hung et al., "Antigen-specific Immunotherapy of Cervical and Ovarian Cancer," Immunol. Rev., 2008, 222:43-69.

Hural et al., "Identification of naturally processed CD4 T cell epitopes from the prostate-specific antigen kallikrein 4 using peptide-based in vitro stimulation," J. Immunol., Jul. 1, 2002, 169(1):557-565.

Hurtado et al., "Identification of Amino Acids of Sindbis Virus E2 Protein Involved in Targeting Tumor Metastases in Vivo," Mol Ther, 2005, 12(5):813-82.

Ikeda et al., "Characterization of an Antigen That Is Recognized on a Melanoma Showing Partial HLA Loss by CTL Expressing an NK Inhibitory Receptor," Immunity, 1997, 6(2):199-208.

Ito et al., "Immunological Characterization of Missense Mutations Occurring Within Cytotoxic T Cell-Defined p53 Epitopes in HLA-A*0201+ Squamous Cell Carcinomas of the Head and Neck," Int. J Cancer, 2007, 120(12):2618-2624.

Jager et al., "Identification of a Naturally Processed NY-ESO-1 Peptide Recognized by CD8+ T Cells in the Context of HLA-B51," Cancer Immun., 2002, 2(12): 13 pages.

Jager et al., "Identification of NY-ESO-1 Epitopes Presented by Human Histocompatibility Antigen (HLA)-DRB4*0101-0103 and Recognized by CD4(+) T Lymphocytes of Patients With NY-ESO-1-expressing Melanoma, " J Exp Med., 2000, 191(4):625-30.

Jager et al., "Recombinant Vaccinia/Fowlpox NY-ESO-1 Vaccines Induce Both Humoral and Cellular NY-ESO-1-specific Immune Responses in Cancer Patients," Proc. Natl. Acad. Sci. U.S.A., 2006, 103(39):14453-8.

Jager et al., "Simultaneous Humoral and Cellular Immune Response Against Cancer-Testis Antigen NY-ESO-1: Definition of Human Histocompatibility Leukocyte Antigen (HLA)-A2-binding Peptide Epitopes," J Exp Med., 1998, 187(2):265-70.

Janjic et al., "Spontaneous CD4+ T Cell Responses Against TRAG-3 in Patients With Melanoma and Breast Cancers," J Immunol., 2006, 177(4):2717-27.

Jaramillo et al., "Identification of HLA-A3-restricted CD8+ T Cell Epitopes Derived From mammaglobin-A, a Tumor-Associated Antigen of Human Breast Cancer," Int. J. Cancer, 2002, 102(5):499-506.

Jerome et al., "Tumor-specific Cytotoxic T Cell Clones From Patients With Breast and Pancreatic Adenocarcinoma Recognize EBV-immortalized B Cells Transfected With Polymorphic Epithelial Mucin Complementary DNA," J Immunol., Aug. 1, 1993, 151(3): 1654-62 (Abstract Only).

Jin et al., "Construction and Characterization of a CTLA-4-targeted scFv-melittin Fusion Protein as a Potential Immunosuppressive Agent for Organ Transplant," Cell Biochem Biophys, 2013, 67(3):1067-74.

Johnson, "Gene Therapy for Cystic Fibrosis, " Chest, 1995, 107(2 Suppl): 77S-83S.

Jose et al., "A Structural and Functional Perspective of Alphavirus Replication and Assembly," Future Microbiol., 2009, 4(7):837-856.

Kang et al., "Identification of a Tyrosinase Epitope Recognized by HLA-A24-restricted, Tumor-Infiltrating Lymphocytes," J. Immunol., 1995, 155(3): 1343-8.

Karanikas et al., "High Frequency of Cytolytic T Lymphocytes Directed Against a Tumor-Specific Mutated Antigen Detectable With HLA Tetramers in the Blood of a Lung Carcinoma Patient With Long Survival," Cancer Res., 2001, 61(9):3718-24.

Kaufman et al., "Oncolytic Viruses: A New Class of Immunotherapy Drugs," Nat Rev Drug Discov., 14:642-662.

Kawakami et al., "Identification of New Melanoma Epitopes on Melanosomal Proteins Recognized by Tumor Infiltrating T Lymphocytes Restricted by HLA-A1, -A2, and -A3 Alleles," J Immunol., 1998, 161(12):6985-92.

Kawakami et al., "Isolation of a New Melanoma Antigen, MART-2, Containing a Mutated Epitope Recognized by Autologous Tumor-Infiltrating T Lymphocytes," J Immunol., 2001, 166(4):2871-7.

Kawakami et al., "Recognition of Multiple Epitopes in the Human Melanoma Antigen gp100 by Tumor-Infiltrating T Lymphocytes Associated With in Vivo Tumor Regression," J Immunol., Apr. 15, 1995, 154(8):3961-3968 (Abstract Only).

Kawashima et al., "Identification of HLA-A3-restricted Cytotoxic T Lymphocyte Epitopes From Carcinoembryonic Antigen and HER-2/neu by Primary in Vitro Immunization With Peptide-Pulsed Dendritic Cells," Cancer Res., 1999, 59(2):431-5.

Kawashima et al., "The Multi-Epitope Approach for Immunotherapy for Cancer: Identification of Several CTL Epitopes From Various Tumor-Associated Antigens Expressed on Solid Epithelial Tumors, " Hum Immunol., 1998, 59(1): 1-14.

Kenter et al., "Vaccination against HPV-16 Oncoproteins for Vulvar Intraepithelial Neoplasia," N Engl J Med., 2009, 361:1838-1847.

Kessler et al., "Efficient Identification of Novel HLA-A(*)0201-presented Cytotoxic T Lymphocyte Epitopes in the Widely Expressed Tumor Antigen PRAME by Proteasome-Mediated Digestion Analysis," J. Exp. Med., 2001, 193(1):73-88.

Kho et al., "Prognostic Variables for Patient Return-to-Work Interval Following Carpal Tunnel Release in a Workers' Compensation Population," Hand (NY), 2017, 12(3):246-251.

(56) References Cited

OTHER PUBLICATIONS

Kido et al., "Use of a Retroviral Vector With an Internal Opsin Promoter to Direct Gene Expression to Retinal Photoreceptor Cells," Current Eye Research, 1996, 15:833-844.

Kimmel, "Identification and Characterization of Specific Clones: Strategy for Confirming the Validity of Presumptive Clones," Methods Enzymol., 1987, 152:507-511.

Kittlesen et al., "Human Melanoma Patients Recognize an HLA-A1-restricted CTL Epitope From Tyrosinase Containing Two Cysteine Residues: Implications for Tumor Vaccine Development," J. Immunol., 1998, 160(5):2099-106.

Knappik et al., "Fully Synthetic Human Combinatorial Antibody Libraries (HuCAL) Based on Modular Consensus Frameworks and CDRs Randomized With Trinucleotides," J Mol. Biol., 2000, 296(1):57-86.

Knights et al., "Modified Tumour Antigen-Encoding mRNA Facilitates the Analysis of Naturally Occurring and Vaccine-Induced CD4 and CD8 T Cells in Cancer Patients," Cancer Immunol Immunother., 2009, 58(3):325-38.

Knudsen et al., "Kinetic and Phenotypic Analysis of CD8+ T Cell Responses After Priming With Alphavirus Replicons and Homologous or Heterologous Booster Immunizations," J Virology, 2014, 8(21):12438-12451.

Kobayashi et al., "New MAGE-4 Antigenic Peptide Recognized by Cytolytic T Lymphocytes on HLA-A1 Tumor Cells," Tissue Antigens., 2003, 62(5):426-32.

Kobayashi et al., "CD4+ T Cells From Peripheral Blood of a Melanoma Patient Recognize Peptides Derived From Nonmutated Tyrosinase," Cancer Res., 1998, 58(2):296-301.

Kobayashi et al., "Identification of an Antigenic Epitope for Helper T Lymphocytes From Carcinoembryonic Antigen," Clin Cancer Res., 2002, 8(10):3219-25.

Kobayashi et al., "Recognition of Prostate and Melanoma Tumor Cells by Six-Transmembrane Epithelial Antigen of Prostate-Specific Helper T Lymphocytes in a Human Leukocyte Antigen Class II-restricted Manner," Cancer Res., 2007, 67(11):5498-504.

Kobayashi et al., "Tumor-reactive T Helper Lymphocytes Recognize a Promiscuous MAGE-A3 Epitope Presented by Various Major Histocompatibility Complex Class II Alleles," Cancer Res., 2001, 61(12):4773-8.

Kohler et al., "Continuous Cultures of Fused Cells Secreting Antibody of Predefined Specificity," Nature, 1975, 256(5517):495-497.

Kozbor et al., "The Production of Monoclonal Antibodies From Human Lymphocytes," Immunology Today, 1983, 4(3):72-9.

La Salle et al., "An Adenovirus Vector for Gene Transfer Into Neurons and Glia in the Brain," Science, 1993, 259(5097):988-990.

Lapointe et al., "Retrovirally Transduced Human Dendritic Cells Can Generate T Cells Recognizing Multiple MHC Class I and Class II Epitopes From the Melanoma Antigen Glycoprotein 100," J Immunol., 2001, 167(8):4758-64.

Larkin et al., "Combined Nivolumab and Ipilimumab or Monotherapy in Untreated Melanoma," N Engl J Med, 373:23-34.

Le et al., "A Live-Attenuated Listeria Vaccine (ANZ-100) and a Live-Attenuated Listeria Vaccine Expressing Mesothelin (CRS-207) for Advanced Cancers: Phase I Studies of Safety and Immune Induction," Clin. Cancer Res., 2012, 18(3):858-68.

Lechner et al., "Immunogenicity of murine solid tumor models as a defining feature of in vivo behavior and response to immunotherapy," Journal of Immunotherapy, 2013 36(9):477-489.

Lennerz et al., "The Response of Autologous T Cells to a Human Melanoma Is Dominated by Mutated Neoantigens," Proc. Natl. Acad. Sci. U.S.A., 2005, 102(44):16013-8.

Li et al., "Detection of Autoantibodies to Multiple Tumor-Associated Antigens in the Immunodiagnosis of Ovarian Cancer," Mol. Med. Report, 2008, 1(4):589-594.

Li et al., "Identification of a WT1 Protein-Derived Peptide, WT1, as a HLA-A 0206-restricted, WT1-specific CTL Epitope, " Microbial. Immunol., 2008, 52(11):551-558.

Lin et al., "HLA-DPB1*05: 01-restricted WT1332-specific TCR-transduced CD4+ T Lymphocytes Display a Helper Activity for WT1-specific CTL Induction and a Cytotoxicity Against Leukemia Cells," J. Immunother., 2013, 36(3): 159-70.

Linard et al., "A Ras-Mutated Peptide Targeted by CTL Infiltrating a Human Melanoma Lesion," J. Immunol., 2002, 168(9):4802-8.

Linnebacher et al., "Frameshift Peptide-Derived T-cell Epitopes: A Source of Novel Tumor-Specific Antigens," Int. J. Cancer., 2001, 93(1):6-11.

Liu et al., "Cells that present both specific ligand and costimulatory activity are the most efficient inducers of clonal expansion of normal CD4 T cells," Proceedings of the National Academy of Sciences, 1992. 89(9):3845-3849.

Liu et al., "Ovarian Cancer Immunotherapy: Opportunities, Progresses and Challenges," J Hematol., Oncol., 2010, 3(7): 11 pages.

Loveland et al., "Mannan-MUC1-pulsed Dendritic Cell Immunotherapy: A Phase I Trial in Patients With Adenocarcinoma," Clin. Cancer Res., 2006, 12(3 Pt 1):869-77.

Lu et al., "Mutated PPP1R3B Is Recognized by T Cells Used to Treat a Melanoma Patient Who Experienced a Durable Complete Tumor Regression," J Immunol., 2013, 190(12):6034-42.

Luiten et al., "A MAGE-A1 peptide is recognized on HLA-B7 human tumors by cytolytic T lymphocytes," Tissue Antigens, 2000, 55(2):149-152.

Luiten et al., "A MAGE-A1 peptide presented to cytolytic T lymphocytes by both HLA-B35 and HLA-A1 molecules," Tissue Antigens, 2000, 56(1):77-81.

Lupetti et al., "Translation of a Retained Intron in Tyrosinase-Related Protein (TRP) 2 mRNA Generates a New Cytotoxic T Lymphocyte (CTL)-defined and Shared Human Melanoma Antigen Not Expressed in Normal Cells of the Melanocytic Lineage, " J Exp Med., 1998, 188(6):1005-16.

Ma et al., "A MAGE-C2 Antigenic Peptide Processed by the Immunoproteasome Is Recognized by Cytolytic T Cells Isolated From a Melanoma Patient After Successful Immunotherapy," Int J Cancer, 2011, 129(10):2427-3.

Ma et al., "Two New Tumor-Specific Antigenic Peptides Encoded by Gene MAGE-C2 and Presented to Cytolytic T Lymphocytes by HLA-A2," Int J Cancer, 2004, 109(5):698-702.

Maccalli et al., "Identification of a Colorectal Tumor-Associated Antigen (COA-1) Recognized by CD4(+) T Lymphocytes," Cancer Res., 2003, 63(20):6735-43.

Maier et al., "Peptide Motifs of HLA-A3, -A24, and -B7 Molecules as Determined by Pool Sequencing," Immunogenetics, 1994, 40(4):306-3.

Makita et al., "Leukemia-associated Fusion Proteins, Dek-Can and Bcr-Abl, Represent Immunogenic HLA-DR-restricted Epitopes Recognized by Fusion Peptide-Specific CD4+ T Lymphocytes," Leukemia, 2002, 16(12):2400-7.

Malik et al., "Resident Memory T Cells in the Skin Mediate Durable Immunity to Melanoma," Sci Immunol, Apr. 14, 2017, 2(eaam6346): 12 pages.

Mandic et al., "One NY-ESO-1-derived Epitope That Promiscuously Binds to Multiple HLA-DR and HLA-DP4 Molecules and Stimulates Autologous CD4+ T Cells From Patients With NY-ESO-1-expressing Melanoma," J Immunol., 2005, 174(3):1751-9.

Mandruzzato et al., "A CASP-8 Mutation Recognized by Cytolytic T Lymphocytes on a Human Head and Neck Carcinoma," J. Exp. Med., 1997, 186(5):785-93.

Manici et al., "Melanoma Cells Present a MAGE-3 Epitope to CD4(+) Cytotoxic T Cells in Association With Histocompatibility Leukocyte Antigen DR11," J Exp Med., 1999, 189(5):871-6.

Marks et al., "By-passing immunization: building high affinity human antibodies by chain shuffling," Biotechnology, Jul. 1992, 10(7):779-783.

Massari et al., "Immune Checkpoint Inhibitors for Metastatic Bladder Cancer," Cancer Treat Rev., 2018, 64:11-20.

Matsuzaki et al., "Recognition of Naturally Processed and Ovarian Cancer Reactive CD8+ T Cell Epitopes Within a Promiscuous HLA Class II T-helper Region of NY-ESO-1," Cancer Immunol Immunother., 2008, 57(8)1185-95.

McCafferty et al., "Phage antibodies: filamentous phage displaying antibody variable domains," Nature, 1990, 348(6301):552-554.

(56) References Cited

OTHER PUBLICATIONS

Melero et al., "Monoclonal antibodies against the 4-1BB T-cell activation molecule eradicate established tumors," Nature Medicine, 1997, 3(6):682-685.
Mellman et al., "Cancer immunotherapy comes of age," Nature, 2011, 480(7378):480-489.
Meng et al., "Identification of an HLA-DPB1*0501 Restricted Melan-A/MART-1 Epitope Recognized by CD4+ T Lymphocytes: Prevalence for Immunotherapy in Asian Populations," J. Immunother., 2011, 23(7):525-534.
Michaux et al., "A Spliced Antigenic Peptide Comprising a Single Spliced Amino Acid Is Produced in the Proteasome by Reverse Splicing of a Longer Peptide Fragment Followed by Trimming," J Immunol., 2014, 192(4):1962-71.
Miller et al., "Improved Retroviral Vectors for Gene Transfer and Expression," Biotechnology, 1989, 7(9):980-990.
Miller, "Retrovirus Packaging Cells ," Human Gene Therapy, 1990, 1:5-14.
Minev et al. "Cytotoxic T cell immunity against telomerase reverse transscriptase in humans," Proceedings of the National Academy of Sciences of the United States of America, Apr. 25, 2000, 97(9):4796-4801.
Miwa et al., "Expression of the Wilms' tumor gene (WT1) in human leukemias, " Leukemia, May 1992, 6(5):405-409 (Abstract Only).
Miyagawa et al., "A Newly Identified MAGE-3-derived, HLA-A24-restricted Peptide Is Naturally Processed and Presented as a CTL Epitope on MAGE-3-expressing Gastrointestinal Cancer Cells," Oncology, 2006, 70(1):54-62.
Miyahara et al., "Determination of Cellularly Processed HLA-A2402-restricted Novel CTL Epitopes Derived From Two Cancer Germ Line Genes, MAGE-A4 and SAGE," Clin Cancer Res., 2005, 11(15):5581-9.
Miyoshi et al., "Stable and Efficient Gene Transfer Into the Retina Using an HIV-based Lentiviral Vector," Proc. Natl. Acad Sci. US.A., 94(19):10319-10323.
Mizote et al., "Three Novel NY-ESO-1 Epitopes Bound to DRB1*0803, DQB1*0401 and DRB1*0901 Recognized by CD4 T Cells From CHP-NY-ESO-1-vaccinated Patients," Vaccine, 2010, 28(32):5338-46.
Moen, "Directions in Gene Therapy," Blood Cells, 1991, 17(2):407-416 (Abstract Only).
Moesta et al., "Local Delivery of Onco VEX mGM-CSF Generates Systemic Antitumor Immune Responses Enhanced by Cytotoxic T-Lymphocyte-Associated Protein Blockade," Clin Cancer Res., 2017, 23(20):6190-6202.
Monji et al., "Identification of a Novel Human Cancer/Testis Antigen, KM-HN-1, Recognized by Cellular and Humoral Immune Responses," Clin Cancer Res., Sep. 15, 2004, 10:6047-57.
Moreau-Aubry et al., "A Processed Pseudogene Codes for a New Antigen Recognized by a CD8(+) T Cell Clone on Melanoma," J Exp Med., 2000, 191(9): 1617-24.
Morel et al., "A Tyrosinase Peptide Presented by HLA-B35 Is Recognized on a Human Melanoma by Autologous Cytotoxic T Lymphocytes," Int. J. Cancer, 1999, 83(6):755-9.
Morgan et al., "High Efficiency TCR Gene Transfer Into Primary Human Lymphocytes Affords Avid Recognition of Melanoma Tumor Antigen Glycoprotein 100 and Does Not Alter the Recognition of Autologous Melanoma Antigens," J. Immunol., 2003, 171(6):3287-3295.
Morizono et al., "Redirecting Lentiviral Vectors Pseudotyped With Sindbis Virus-Derived Envelope Proteins to DC-SIGN by Modification of N-linked Glycans of Envelope Proteins," J Viral., 2010, 84(14):6923-693.
Morris et al., "Development and characterization of recombinant human Fc: OX40L fusion protein linked via a coiled-coil trimerization domain," Molecular Immunology, 2007, 44(12):3112-3121.
Motzer et al., "Nivolumab for Metastatic Renal Cell Carcinoma: Results of a Randomized Phase II Trial," J Clin Oneal, 2015, 33(13):1430-1437.
Munir et al., "HLA-restricted CTL That Are Specific for the Immune Checkpoint Ligand PD-L1 Occur With High Frequency in Cancer Patients," Cancer Res., 2013, 73(6): 1764-76.
Muraoka et al., "Establishment of Animal Models to Analyze the Kinetics and Distribution of Human Tumor Antigen-Specific CD8+ T Cells," Vaccine, 2013, 31(17):2110-2118.
Nakatsuka et al., "Immunohistochemical Detection of WT1 Protein in a Variety of Cancer Cells," Mod. Pathol., 2006, 19(6):804-814.
Naldini et al., "In Vivo Gene Delivery and Stable Transduction of Nondividing Cells by a Lentiviral Vector," Science, 1996, 272(5259):263-267.
Needleman et al., "A General Method Applicable to the Search for Similarities in the Amino Acid Sequence of Two Proteins," J. Mol. Biol., 1970, 48:443-453.
Neumann et al., "A Peptide Epitope Derived From the Cancer Testis Antigen HOM-MEL-40/SSX2 Capable of Inducing CD4+ and CD8+ T-cell as Well as B-cell Responses," Cancer Immunol Immunother., 2011, 60(9):1333-46.
Neumann et al., "Identification of an HLA-DR-restricted Peptide Epitope With a Promiscuous Binding Pattern Derived From the Cancer Testis Antigen HOM-MEL-40/SSX2," Int J Cancer, 2004, 112(4):661-8.
Nezafat et al., "A novel multi-epitope peptide vaccine against cancer: An in silico approach," Journal of Theoretical Biology, Feb. 7, 2014, 349:121-134.
Nielsen et al., "MHC Class II Epitope Predictive Algorithms," Immunology, 2010, 130(3):319-328.
Noppen et al., "Naturally Processed and Concealed HLA-A2.1-restricted Epitopes From Tumor-Associated Antigen Tyrosinase-Related protein-2," Int. J. Cancer, 2000, 87(2):241-6.
Novellino et al., "Identification of a Mutated Receptor-Like Protein Tyrosine Phosphatase Kappa as a Novel, Class II HLA-restricted Melanoma Antigen," J. Immunol., 2003, 170(12):6363-70.
Nuber et al., "Fine Analysis of Spontaneous MAGE-C1/CT7-specific Immunity in Melanoma Patients," Proc Natl Acad Sci U.S.A. 107(34):15187-92.
Ochsenreither et al., "Cyclin-A1 Represents a New Immunogenic Targetable Antigen Expressed in Acute Myeloid Leukemia Stem Cells With Characteristics of a Cancer-Testis Antigen," Blood, 2012, 119(23):5492-501.
Oehlrich et al., "Generation of RAGE-1 and MAGE-9 Peptide-Specific Cytotoxic T-lymphocyte Lines for Transfer in Patients With Renal Cell Carcinoma," Int. J. Cancer, 2005, 117(2):256-64.
Ohminami et al., "HLA Class I-restricted Lysis of Leukemia Cells by a CD8(+) Cytotoxic T-lymphocyte Clone Specific for WT1 Peptide," Blood, 2000, 95(1):286-93.
Ohue et al., "Spontaneous Antibody, and CD4 and CD8 T-cell Responses Against XAGE-1b (GAGED2a) in Non-Small Cell Lung Cancer Patients," Int J Cancer, 2012, 131(5):E649-58.
Oiso et al., "A Newly Identified MAGE-3-derived Epitope Recognized by HLA-A24-restricted Cytotoxic T Lymphocytes," Int J Cancer, 1999, 81(3):387-94.
Oji et al., "Expression of the wilms' tumor gene WTI in solid tumors and its involvement intumor cell growth," Japan J Cancer. Res., Feb. 1999, 90(19):194-204.
Oka et al., "Cancer Immunotherapy Targeting Wilms' Tumor Gene WT1 Product," J Immunol., 2000, 164(4):1873-80.
Okugawa et al., "A Novel Human HER2-derived Peptide Homologous to the Mouse K(d)-restricted Tumor Rejection Antigen Can Induce HLA-A24-restricted Cytotoxic T Lymphocytes in Ovarian Cancer Patients and Healthy Individuals," Eur J Immunol., 2000, 30(11):3338-46.
Oliveira et al., "Alternative antigen processing for MHC class I: mutiple roads lead to rome," Frontiers in Immunology, Jun. 5, 2015, 6(298): 10 pages.
Olson et al., "HLA-A2-restricted T-cell epitopes specific for prostatic acid phosphatase," Cancer Immunol Immunother., 2010, 59(6):943-53.
Olson et al., "The Androgen Receptor: A Biologically Relevant Vaccine Target for the Treatment of Prostate Cancer," Cancer Immunol., 2010, Immunother., 62(3):585-596.

(56) References Cited

OTHER PUBLICATIONS

Ono et al., "Plasmid DNAs directly injected into mouse brain with lipofectin can be incorporated and expressed by brain cells," Neuroscience Letters, 1990, 117(3): 259-263.
Osen et al., "Screening of Human Tumor Antigens for CD4 T Cell Epitopes by Combination of HLA-transgenic Mice, Recombinant Adenovirus and Antigen Peptide Libraries," PLoS One., 2010, 5(11):e14137, 13 pages.
Ottaviani et al., "A MAGE-1 Antigenic Peptide Recognized by Human Cytolytic T Lymphocytes on HLA-A2 Tumor Cells," Cancer Immunol Immunother., 2005, 54(12):1214-20.
Ottaviani et al., "A New MAGE-4 Antigenic Peptide Recognized by Cytolytic T Lymphocytes on HLA-A24 Carcinoma Cells," Cancer Immunol Immunother., 2006, 55(7):867-72.
Panelli et al., "A Tumor-Infiltrating Lymphocyte From a Melanoma Metastasis With Decreased Expression of Melanoma Differentiation Antigens Recognizes MAGE-12," J Immunol., 2000, 164(8):4382-92.
Pardoll, "The Blockade of Immune Checkpoints in Cancer Immunotherapy," Nat Rev Cancer, 2012, 12(4):252-264.
Parker et al., "Scheme for Ranking Potential HLA-A2 Binding Peptides Based on Independent Binding of Individual Peptide Side-Chains," J Immunol., 1994, 152(1):163-175.
Parkhurst et al., "Identification of a Shared HLA-A*0201-restricted T-cell Epitope From the Melanoma Antigen Tyrosinase-Related Protein 2 (TRP2)," Cancer Res., 1998, 58(21):4895-901.
Parkhurst et al., "Induction of CD4+ Th1 Lymphocytes That Recognize Known and Novel Class II MHC Restricted Epitopes From the Melanoma Antigen gp100 by Stimulation With Recombinant Protein," J Immunother., 2004, 27(2):79-91.
Parkhurst et al., "T Cells Targeting Carcinoembryonic Antigen Can Mediate Regression of Metastatic Colorectal Cancer but Induce Severe Transient Colitis," Mol. Ther., 2011, 19(3):620-6.
Parmiani et al., "Cancer Immunotherapy With Peptide-Based Vaccines: What Have We Achieved? Where Are We Going?," J. Nat. Cancer Inst., 94(11):805-818.
Paschen et al., "Detection of Spontaneous CD4+ T-cell Responses in Melanoma Patients Against a Tyrosinase-Related protein-2-derived Epitope Identified in HLA-DRB1*0301 Transgenic Mice," Clin. Cancer Res., 2005, (14):5241-7.
Pascolo et al., "A MAGE-A1 HLA-A A*0201 Epitope Identified by Mass Spectrometry," Cancer Res., 2001, 61(10):4072-7.
PCT International Preliminary Report on Patentability in International Appln. PCT/US2019/020562, dated Sep. 17, 2020, 10 pages.
PCT International Search Report and Written Opinion in International Appln. No. PCT/US2018/020985, dated Aug. 20, 2018, 22 pages.
PCT International Search Report and Written Opinion in International Appln. No. PCT/US2019/020562, dated Jun. 6, 2019, 13 pages.
Pettitt et al., "CAR-T Cells: A Systematic Review and Mixed Methods Analysis of the Clinical Trial Landscape," Mol. Ther., 2018, 26(2):342-35.
Pichard et al., "Detection, Isolation, and Characterization of Alpha-Fetoprotein-Specific T Cell Populations and Clones Using MHC Class I Multimer Magnetic Sorting," J Immunother., 2008, 31(3):246-53.
Pieper et al., "Biochemical Identification of a Mutated Human Melanoma Antigen Recognized by CD4(+) T Cells, " J Exp Med., 1999, 189(5):757-66.
Pils et al., "In Ovarian Cancer the Prognostic Influence of HER2/neu Is Not Dependent on the CXCR4/SDF-1 Signalling Pathway," Br. J. Cancer, 96(3):485-91.
Powers et al., "Evolutionary Relationships and Systematics of the Alphaviruses," J Viral., 2001, 75(21): 10118-10131.
Principals and Practice of the Biologic Therapy for Cancer, 3rd ed., Resenberg (ed)., 2000, Chapter 16.7: Identification of Human Tumor antigens by Serological Expression Cloning, p. 557-570.
Probst-Kepper et al., "An Alternative Open Reading Frame of the Human Macrophage Colony-Stimulating Factor Gene Is Independently Translated and Codes for an Antigenic Peptide of 14 Amino Acids Recognized by Tumor-Infiltrating CD8 T Lymphocytes," J Exp Med. 193(10):1189-98.
Qian et al., "Dickkopf-1 (DKK1) Is a Widely Expressed and Potent Tumor-Associated Antigen in Multiple Myeloma," Blood, 2007, 110(5):1587-94.
Raghavan et al., "Extended Repertoire of Permissible Peptide Ligands for HLA-B*2702," Protein Science, 1996, 5(10):2080-208.
Rajasagi et al., "Systematic Identification of Personal Tumor-Specific Neoantigens in Chronic Lymphocytic Leukemia," Blood, 2014, 124(3):453-62.
Rammensee et al., "SYFPEITHI: database for MHC ligands and peptide motifs," Immunogenetics, 1999, 50:213-219.
Reche et al., "Enhancement to the RANKPEP Resource for the Prediction of Peptide Binding to MHC Molecules Using Profiles, " Immunogenetics, 2004, 56:405-419.
Reche et al., "Prediction of MHC Class I Binding Peptides Using Profile Motifs," Human Immunol., 2002, 63(9):701-709.
Reche et al., "Prediction of peptide-MHC Binding Using Profiles," Methods Mol. Biol., 2007, 409:185-200.
Reuschenbach et al., "A systematic review of humoral immune responses against tumor antigens," Cancer Immunol. Immunother., Oct. 2009, 58(10):1535-1544.
Ribas, "Adaptive Immune Resistance: How Cancer Protects From Immune Attack," Cancer Discov, 2015, 5(9):915-919.
Riley et al., "Identification of a New Shared HLA-A2.1 Restricted Epitope From the Melanoma Antigen Tyrosinase," J. Immunother., 2001, 24(3):212-220.
Rimoldi et al., "Efficient Simultaneous Presentation of NY-ESO-1/LAGE-1 Primary and Nonprimary Open Reading Frame-Derived CTL Epitopes in Melanoma," The Journal of Immunology, 2000, 165(12):7253-7261.
Ripberger et al., "Identification of an HLA-A0201-restricted CTL Epitope Generated by a Tumor-Specific Frameshift Mutation in a Coding Microsatellite of the OGT Gene," J Clin Immunol., Sep. 2003, 23(5):415-423.
Robbins et al., "A Mutated f3-Catenin Gene Encodes a Melanoma-specific Antigen Recognized by Tumor Infiltrating Lymphocytes, " J. Exp. Med., 1996, 183(3):1185-1192.
Robbins et al., "Mining exomic sequencing data to identify mutated antigens recognized by adoptively transferred tumor-reactive T cells," Nature Med., Jun. 2013, 19(6):747-752.
Robbins et al., "Multiple HLA class II-restricted melanocyte differentiation antigens are recognized by tumor-infiltrating lymphocytes from a patient with melanoma," J. Immunol., 2002, 169(10):6036-6047.
Robbins et al., "The intronic region of an incompletely spliced gp100 gene transcript encodes an epitope recognized by melanoma-reactive tumor-infiltrating lymphocytes," J Immunol., Jul. 1, 1997, 159(1):303-308.
Rodeberg et al., "Recognition of six-transmembrane epithelial antigen of the prostate-expressing tumor cells by peptide antigen-induced cytotoxic T lymphocytes," Clin. Cancer Res., 2005, 11(12):4545-4552.
Rongcun et al., "Identification of New HER2/neu-Derived Peptide Epitopes That Can Elicit Specific CTL Against Autologous and Allogeneic Carcinomas and Melanomas," J Immunol., 1999, 163(2):1037-1044.
Ronsin et al., "A Non-AUG-Defined Alternative Open Reading Frame of the Intestinal Carboxyl Esterase mRNA Generates an Epitope Recognized by Renal Cell Carcinoma-Reactive Tumor-Infiltrating Lymphocytes In Situ," J Immunol., 1999, 163(1):483-490.
Rosenberg et al., "Gene Transfer into Humans—Immunotherapy of Patients with Advanced Melanoma, Using Tumor-Infiltrating Lymphocytes Modified by Retroviral Gene Transduction," The New England Journal of Medicine, Aug. 30, 1990, 323(9):570-578.
Roska et al., "Dissection of the functions of antigen-presenting cells in the induction of T cell activation," The Journal of Immunology, 1985, 135(5):2953-2961.
Russo et al., "Dendritic cells acquire the MAGE-3 human tumor antigen from apoptotic cells and induce a class I-restricted T cell

(56) References Cited

OTHER PUBLICATIONS response," Proceedings of the National Academy of Sciences of the United States of America, 2000, 97(5):2185-2190.
Sanders, "No False Start for Novel Pseudotyped Vectors," Curr. Opin. Biotechnol., 2002, 13(5):437-442.
Sanmamed et al., "Agonists of co-stimulation in cancer immunotherapy directed against CD137, OX40, GITR, CD27, CD28, and ICOS," Seminars in Oncology, 2015, 42(4):640-655.
Scardino et al., "HER-2/neu and hTERT cryptic epitopes as novel targets for broad spectrum tumor immunotherapy," J Immunol., 2002, 168(11):5900-5906.
Scardino et al., "Identification of HER-2/neu immunogenic epitopes presented by renal cell carcinoma and other human epithelial tumors," Eur J Immunol., Nov. 2001, 31(11):3261-3270.
Scherwitzl et al., "Systemically administered Sindbis virus in combination with immune checkpoint blockade induces curative antitumor immunity," Molecular Therapy: Oncolytics, Jun. 2018, 9:51-63.
Schiavetti et al., "A human endogenous retroviral sequence encoding an antigen recognized on melanoma by cytolytic T lymphocytes," Cancer Res., Oct. 2002, 62(19):5510-5516.
Schmitz et al., "Generation of survivin-specific CD8+ T effector cells by dendritic cells pulsed with protein or selected peptides," Cancer Res., 2000, 60(17):4845-4849.
Schroers et al., "Human telomerase reverse transcriptase-specific T-helper responses induced by promiscuous major histocompatibility complex class II-restricted epitopes," Clin. Cancer Res., 2003, 9(13):4743-4755.
Schroers et al., "Identification of HLA DR7-restricted epitopes from human telomerase reverse transcriptase recognized by CD4+ T-helper cells," Cancer Res., 2002, 62(9):2600-2605.
Schultz et al., "A MAGE-3 peptide recognized on HLA-B35 and HLA-A1 by cytolytic T lymphocytes, " Tissue Antigens, 2001, 57(2):103-109.
Schultz et al., "A MAGE-A3 peptide presented by HLA-DP4 is recognized on tumor cells by CD4+ cytolytic T lymphocytes," Cancer Res., 2000, 60(22):6272-6275.
Schultz et al., "Functional analysis of tumor-specific Th cell responses detected in melanoma patients after dendritic cell-based immunotherapy," J Immunol., 2004, 172(2):1304-1310.
Schultz et al., "The production of a new MAGE-3 peptide presented to cytolytic T lymphocytes by HLA-B40 requires the immunoproteasome," J Exp Med., 2002, 195(4):391-399.
Schwab et al., "Past, present and future targets for immunotherapy in ovarian cancer," Immunotherapy, 2014, 6(12):1279-1293.
Schwitalle et al., "Immunogenic peptides generated by frameshift mutations in DNA mismatch repair-deficient cancer cells," Cancer Immun., 2004, 4(1):14.
Seidah et al., "The Biology and Therapeutic Targeting of the Proprotein Convertases," Nature Reviews Drug Discovery, 2012, 11(5):367-38.
Sensi et al., "Identification of a novel gp100/pMel17 peptide presented by HLA-A*6801 and recognized on human melanoma by cytolytic T cell clones," Tissue Antigens., 2002, 59(4):273-279.
Sensi et al., "Immunogenicity without Immunoselection: A Mutant but Functional Antioxidant Enzyme Retained in a Human Metastatic Melanoma and Targeted by CD8+ T Cells with a Memory Phenotype," Cancer Res., 2005, 65(2):632-640.
Sharkey et al., "CD4(+) T-cell recognition of mutated B-RAF in melanoma patients harboring the V599E mutation," Cancer Res., 2004, 64(5): 1595-1599.
Sharkey et al., "Ross River virus glycoprotein-pseudotyped retroviruses and stable cell lines for their production," J Virology, Mar. 2001, 75(6):2653-2659.
Sharma et al., "Immune Checkpoint Targeting in Cancer Therapy: Toward Combination Strategies With Curative Potential," Cell, 2015, 161:205-214.
Sharp, "Gene Therapy," The Lancet, May 1991, 337:1277-1278.

Shimono et al., "Identification of DR9-restricted XAGE antigen on lung adenocarcinoma recognized by autologous CD4 T-cells," Int J Oncol., Apr. 2007, 30(4):835-840.
Siegel et al., "Induction of antitumour immunity using survivin peptide-pulsed dendritic cells in a murine lymphoma model," Br. J. Haematology, Sep. 2003, 122(6):911-914.
Skipper et al., "An HLA-A2-restricted Tyrosinase Antigen on Melanoma Cells Results from Posttranslational Modification and Suggests a Novel Pathway for Processing of Membrane Proteins," J. Exp. Med., Feb. 1996, 183(2):527-534.
Skipper et al., "Shared epitopes for HLA-A3-restricted melanoma-reactive human CTL include a naturally processed epitope from Pmel-17/gp100.," J Immunol., Dec. 1, 1996, 157(11):5027-5033.
Slager et al., "CD4+ Th2 Cell Recognition of HLA-DR-Restricted Epitopes Derived from CAMEL: A Tumor Antigen Translated in an Alternative Open Reading Frame," J Immunol., Feb. 2003, 170(3):1490-1497.
Slager et al., "Identification of multiple HLA-DR-restricted epitopes of the tumor-associated antigen CAMEL by CD4+ Th1/Th2 lymphocytes," J Immunol., 2004, 172(8):5095-5102.
Slager et al., "Induction of CAMEL/NY-ESO-ORF2-specific CD8 φ T cells upon stimulation with dendritic cells infected with a modified Ad5 vector expressing a chimeric Ad5/35 fiber," Cancer Gene Ther., 2004, 11(3):227-236.
Slansky et al., "Enhanced antigen-specific antitumor immunity with altered peptide ligands that stabilize the MHC-peptide-TCR complex," Immunity, Oct. 2000, 13(4):529-538.
Spizzo et al., "Overexpression of epithelial cell adhesion molecule (Ep-CAM) is an independent prognostic marker for reduced survival of patients with epithelial ovarian cancer," Gynecology Oncology, 2006, 103(2):483-488.
Spranger et al., "Up-regulation of PD-L1, IDO, and Tregs in the Melanoma tumor microenvironment is driven by CD8+ T cells," Sci Transl Med, 2013, 5(200ra116):1-10.
Staubinger et al., "Liposomes as carriers for intracellular delivery of nucleic acids," Methods in Enzymology, 1983, 101:512-527.
Stroobant et al., "Inefficient exogenous loading of a tapasin-dependent peptide onto HLA-B*44:02 can be improved by acid treatment or fixation of target cells," Eur J Immunol., 2012, 42(6):1417-1428.
Suda et al., "Identification of human leukocyte antigen-A24-restricted epitope peptides derived from gene products upregulated in lung and esophageal cancers as novel targets for immunotherapy," Cancer Sci., Nov. 2007, 98(11):1803-1808.
Sun et al., "A new LAGE-1 peptide recognized by cytolytic T lymphocytes on HLA-A68 tumors," Cancer Immunol Immunother., 2006, 55(6):644-652.
Suri et al., "Targeting cancer testis antigens for biomarkers and immunotherapy in colorectal cancer: Current status and challenges," World J Gastrointestinal Oncology, Dec. 2015, 7(12):492-502.
Taglimonte et al., "Antigen-specific vaccines for cancer treatment," Human Vaccines and Immunotherapeutics, Oct. 31, 2014, 10(11):3332-3346.
Tahara et al., "Identification of a MAGE-2-encoded Human Leukocyte AntigenA24-binding Synthetic Peptide That Induces Specific Antitumor Cytotoxic T Lymphocytes," Clin Cancer Res., Aug. 1999, 5(8):2236-2241.
Tajima et al., "Identification of an epitope from the epithelial cell adhesion molecule eliciting HLA-A*2402-restricted cytotoxic T-lymphocyte responses," Tissue Antigens, Dec. 2004, 64(6):650-659.
Takenoyama et al., "A point mutation in the NFYC gene generates an antigenic peptide recognized by autologous cytolytic T lymphocytes on a human squamous cell lung carcinoma," Int. J Cancer, 2006, 118(8):1992-1997.
Tandon et al., "Emerging strategies for EphA2 receptor targeting for cancer therapeutics," Expert Opin. Ther. Targets, Dec. 2010, 15(1):31-51.
Tanzarella et al., "Identification of a Promiscuous T-Cell Epitope Encoded by Multiple Members of the MAGE Family," Cancer Res., Jun. 1999, 59(11):2668-2674.

(56) References Cited

OTHER PUBLICATIONS

Thomas et al., "Mesothelin-specific CD8(+) T Cell Responses Provide Evidence of in Vivo Cross-Priming by Antigen-Presenting Cells in Vaccinated Pancreatic Cancer Patients," J Exp Med., 200(3):297-306.
Thomson et al., "Delivery of Multiple CD8 Cytotoxic T Cell Epitopes by DNA Vaccination," J. Immunol., Feb. 1998, 160(4):1717-1723.
Tolstoshev et al., "Gene expression using retroviral vectors," Current Opinion in Biotechnology, Oct. 1990, 1(1):55-61.
Tomita et al., "A novel tumor-associated antigen, cell division cycle 45-like can induce cytotoxic T-lymphocytes reactive to tumor cells," Cancer Sci., Apr. 2011, 102(4):697-705.
Tomita et al., "Identification of immunogenic LY6K long peptide encompassing both CD4+ and CD8+ T-cell epitopes and eliciting CD4+ T-cell immunity in patients with malignant disease," Oncoimmunology, Feb. 2014 3(e28100):1-15.
Topalian et al., "Melanoma-specific CD4+ T cells recognize nonmutated HLA-DR-restricted tyrosinase epitopes," J. Exp. Med., May 1, 1996, 183(5): 1965-1971.
Topalian et al., "Revelation of a Cryptic Major Histocompatibility Complex Class II-restricted Tumor Epitope in a Novel RNA-processing Enzyme," Cancer Res., Oct. 1, 2002, 62(19):5505-5509.
Topalian et al., "Safety, Activity, and Immune Correlates of Anti-PD-1 Antibody in Cancer," N Engl. J Med., 2012, 366(26):2443-2454.
Touloukian et al., "Expression of a "Self-"Antigen by Human Tumor Cells Enhances Tumor Antigen-specific CD4+ T-Cell Function," Cancer Res., Sep. 2002, 62(18):5144-5147.
Touloukian et al., "Identification of a MHC class II-restricted human gp100 epitope using DR4-IE transgenic mice," J Immunol., Apr. 1, 2000, 164(7):3535-3542.
Touloukian et al., "Normal Tissue Depresses While Tumor Tissue Enhances Human T Cell Responses In Vivo to a Novel Self/Tumor Melanoma Antigen, OA1," J. Immunol., Feb. 1, 2003, 170(3):1579-1585.
Traversari et al., "A nonapeptide encoded by human gene MAGE-1 is recognized on HLA-A1 by cytolytic T lymphocytes directed against tumor antigen MZ2-English," J Exp Med., Nov. 1, 1992, 176(5):1453-1457.
Tsai et al., "Identification of Subdominant CTL Epitopes of the GP100 Melanoma-Associated Tumor Antigen by Primary in Vitro Immunization with Peptide-Pulsed Dendritic Cells," J Immunol., Feb. 15, 1997, 158(4):1796-1802 (Abstract Only).
Tseng et al., "In Vivo Antitumor Activity of Sindbis Viral Vectors," J Natl Cancer Inst., Dec. 4, 2002, 94(23):1790-1802.
Tseng et al., "Systemic Tumor Targeting and Killing by Sindbis Viral Vectors," Nat Biotechnol., 2004, 22(1):70-77.
Tseng et al., "Using Sindbis Viral Vectors for Specific Detection and Suppression of Advanced Ovarian Cancer in Animal Models," Cancer Res., Sep. 15, 2004, 64(18):6684-6692.
Tsukahara et al., "Identification of Human Autologous Cytotoxic T-Lymphocyte-Defined Osteosarcoma Gene That Encodes a Transcriptional Regulator, Papillomavirus Binding Factor," Cancer Research, Aug. 1, 2004, 64(15):5442-5448.
Tumeh et al., "PD-1 Blockade Induces Responses by Inhibiting Adaptive Immune Resistance," Nature, 2014, 515(7528):568-571.
Underwood et al., "Ovarian Tumor Cells Express a Novel Multi-Domain Cell Surface Serine Protease," BBA Mol. Basis of Disease, 2000, 1502(3):337-350.
UniProt Accession No. P41273, "Tumor necrosis factor ligand superfamily member 9," dated Feb. 15, 2017, 3 pages.
UniProt Accession No. P01857, "Immunoglobulin heavy constant gamma 1," dated Feb. 15, 2017, 11 pages.
Valmori et al., "Expression of synovial sarcoma X (SSX) antigens in epithelial ovarian cancer and identification of SSX-4 epitopes recognized by CD4+ T cells," Clin Cancer Res. Jan. 15, 2006, 12(2):398-404.

Valmori et al., "Naturally Occuring Human Lymphocyte Antigen-A2 Restricted CD8+ T-Cell Response to the Cancer Testis Antigen NY-ESO-1 in Melanoma Patients," Cancer Res., Aug. 2000, 60(16):4499-4506.
Van Den Eynde et al., "A new antigen recognized by cytolytic T lymphocytes on a human kidney tumor results from reverse strand transcription," J. Exp. Med., Decemeber 20, 1999, 190(12): 1793-1800.
Van den Eynde et al., "A new family of genes coding for an antigen recognized by autologous cytolytic T lymphocytes on a human melanoma," J Exp Med., Sep. 1, 1995, 182(3):689-698.
Van der Bruggen et al., "A peptide encoded by human gene MAGE-3 and presented by HLA-A2 induces cytolytic T lymphocytes that recognize tumor cells expressing MAGE-3," Eur J Immunol., Decemeber 1994, 24(12):3038-3043.
Van der Bruggen et al., Autologous cytolytic T lymphocytes recognize a MAGE-1 nonapeptide on melanomas expressing HLA-Cw* 1601, Eur J Immunol. Sep. 1994, 24(9):2134-2140.
Vantomme et al., "A new tumor-specific antigenic peptide encoded by MAGE-6 is presented to cytolytic T lymphocytes by HLA-Cw16," Cancer Immun., Dec. 10, 2003, 3(17):1-8.
Vauchy et al., "CD20 alternative splicing isoform generates immunogenic CD4helper T epitopes," Int J Cancer, Jul. 1, 2015, 137(1):116-126.
Vigneron et al., "A peptide derived from melanocytic protein gp100 and presented by HLA-B35 is recognized by autologous cytolytic T lymphocytes on melanoma cells," Tissue Antigens, 2005, 65(2):156-162.
Vigneron et al., "Database of T cell-defined human tumor antigens: the 2013 update," Cancer Immun., Jul. 15, 2013, 13(15):1-6.
Vigneron et al., "Identification of a new peptide recognized by autologous cytolytic T lymphocytes on a human melanoma," Cancer Immunity, Jul. 2002, 2(9): 10 pages.
Vissers et al., "The Renal Cell Carcinoma-associated Antigen G250 Encodes a Human Leukocyte Antigen (HLA)-A2.1-restricted Epitope Recognized by Cytotoxic T Lymphocytes," Cancer Research, Nov. 1, 1999, 59(21):5554-5559.
Vonderheide et al., "The Telomerase Catalytic Subunit Is aWidely Expressed Tumor-Associated AntigenRecognized by Cytotoxic T Lymphocytes," Immunity, Jun. 1999, 10(6):673-679.
Wahl et al., "Molecular hybridization of immobilized nucleic acids: theoretical concepts and practical considerations," Methods Enzymol., 1987, 152:399-407.
Walton et al., "Spontaneous CD8 T cell responses against the melanocyte differentiation antigen RAB38/NY-MEL-1 in melanoma patients," J Immunol., Dec. 1, 2006, 177(11):8212-8218.
Wang et al., "A Breast and Melanoma-Shared Tumor Antigen: T Cell Responses to Antigenic Peptides Translated from Different Open Reading Frames," Journal of Immunology, Oct. 1, 1998, 161(7):3596-3606.
Wang et al. "Identification of TRP-2 as a Human Tumor Antigen Recognized by Cytotoxic T Lymphocytes, " Journal of Experimental Medicine, Dec. 1, 1996, 184(6):2207-2216.
Wang et al., "A systematic assessment of MHC class II peptide beinding predictions and evaluation of a consensus approach, " PLoS Comput. Biol., Apr. 2008, 4(4):e10000048, 10 pages.
Wang et al., "Calreticulin promotes tumor lymphocyte infiltration and enhances the antitumor effects of immunotherapy by up-regulating the endothelial expression of adhesion molecules," Int. J Cancer, Jul. 29, 2011, 130(12):2892-2902.
Wang et al., "Cloning genes encoding MHC class II-restricted antigens: mutated CDC27 as a tumor antigen," Science, May 21, 1999, 284(5418): 1351-1354.
Wang et al., "Identification of a Mutated Fibronectin as a Tumor Antigen Recognized by CD4 T Cells: Its Role in Extracellular Matrix Formation and Tumor Metastasis," Journal of Experimental Medicine, Jun. 3, 2002, 195(11):1397-1406.
Wang et al., "Identification of a novel major histocompatibility complex class II-restricted tumor antigen resulting from a chromosomal rearrangement recognized by CD4(+) T cells," J Exp Med., May 17, 1999, 189(10):1659-1668.
Wang et al., "Peptide binding predictions for HLA DR, DP and DQ molecules," BMC Bioinformatics, Nov. 2010, 11(568): 12 pages.

(56) References Cited

OTHER PUBLICATIONS

Wang et al., "Recognition of a New ARTC1 Peptide Ligand Uniquely Expressed in Tumor Cells by Antigen-Specific CD4 Regulatory T Cells," J Immunol., Apr. 2005, 174(5):2661-2670.

Wang et al., "Recognition of an antigenic peptide derived from tyrosinase-related protein-2 by CTL in the context of HLA-A31 and -A33," J. Immunol., Jan. 15, 1998, 160(2):890-897.

Wang et al., "Recognition of Breast Cancer Cells by CD8+ Cytotoxic T-Cell Clones Specific for NY-BR-1," Cancer Res., Jul. 1, 2006, 66(13):6826-6833.

Wang et al., "Selective identification of HLA-DP4 binding T cell epitopes encoded by the MAGE-A gene family," Cancer Immunol Immunother., 2007, 56(6):807-818.

Wang et al., "Tumor-Specific Human CD4+ Regulatory T Cells and Their Ligands: Implications for Immunotherapy," Immunity, Jan. 2004, 20(1):107-118.

Webb et al., "Tumor-infiltrating Lymphocytes Expressing the Tissue Resident Memory Marker CD103 Are Associated With Increased Survival in High-Grade Serous Ovarian Cancer," Clin Cancer Res., 20(2):434-444.

Wen et al., "Identification of promiscuous HLA-DR-restricted CD4+ T-cell epitopes on the cancer-testis antigen HCA587," Cancer Sci., Aug. 2011, 102(8):1455-1461.

Wick et al., "Surveillance of the Tumor Mutanome by T Cells During Progression From Primary to Recurrent Ovarian Cancer," Clin. Cancer Res., Mar. 1, 2014, 20(5):1125-1134.

Wilkinson et al., "Human kallikrein 4 signle peptide induces cytotoxis T cell responses in healthy donors and prostate cancer patients," Cancer Immunol., Immunother., 2012, 61(2):169-179.

Wolchok et al., "Overall Survival With Combined Nivolumab and Ipilimumab in Advanced Melanoma," N Engl J Med., 2017, 377(14):1345-1356.

Wolfel et al., "A p16INK4a-insensitive CDK4 mutant targeted by cytolytic T lymphocytes in a human melanoma," Science, Sep. 1, 1995, 269(5228):1281-1284.

Wolfel et al., "Two tyrosinase nonpeptides recognized on HLA-A2 melanomas by autologous cytolytic T lymphocytes," Eur. J. Immunol., 1994, 24(3):759-764.

Wolff et al., "Direct gene transfer into mouse muscle in vivo," Science, Mar. 23, 1990, 247(4949):1465-1468.

Woodland, "Jump-starting the immune system: prime-boosting comes of age," TRENDS in Immunology, Feb. 2004, 25(2):98-104.

Wu et al., "Receptor-mediated gene delivery and expression in vivo," Journal of Biological Chemistry, Oct. 15, 1989, 263(29):14621-14624.

Wu et al., "Targeting genes: delivery and persistent expression of a foreign gene driven by mammalian regulatory elements in vivo," Journal of Biological Chemistry, Oct. 15, 1989, 264(29):16985-16987.

Wülfing et al., "A receptor/cytoskeletal movement triggered by costimulation during T cell activation," Science, 1998, 282(5397):2266-2269.

Wurz et al., "Novel cancer antigens for personalized immunotherapies: latest evidence and clinical potential," Therapeutic Advances in Medical Oncology, Jan. 2016, 8(1):4-31.

Yang et al., "A novel mimovirus vaccine containing survivin epitope with adjuvant IL-15 induces long-lasting cellular immunity and high antitumor efficiency," Mol. Immunol., Mar. 2008, 45(6): 1674-1681.

Yang et al., "An introduction to epitope prediction methods and software," Rev. Med. Viral., Dec. 19, 2008, 19(2):77-96.

Yotnda et al., "Cytotoxic T Cell Response against the Chimeric ETV6-AML 1 Protein in Childhood Acute Lymphoblastic Leukemia," J. Clin. Invest. Jul. 1998, 102(2):455-462.

Yotnda et al., "Cytotoxic T Cell Response Against the Chimeric p210 BCR-ABL Protein in Patients with Chronic Myelogenous Leukemia," J. Clin. Invest., May 1998, 101(10):2290-2296.

Yun et al., "Augmentation of immune response by altered peptide ligands of the antigenic peptide in a human CD4+ T-cell clone reacting to TEL/AML1 fusion protein," Tissue Antigens, Aug. 1999, 54(2):153-161.

Zamarin et al., "Localized Oncolytic Virotherapy Overcomes Systemic Tumor Resistance to Immune Checkpoint Blockade Immunotherapy," Sci Transl. Med., Mar. 5, 2014, 6(226):226ra23, 12 pages.

Zarour et al., "NY-ESO-1 119-143 is a promiscuous major histocompatibility complex class II T-helper epitope recognized by Th1- and Th2-type tumor-reactive CD4+ T cells," Cancer Res., Jan. 1, 2002, 62(1):213-218.

Zarour et al., "NY-ESO-1 encodes DRB1*0401-restricted epitopes recognized by melanoma-reactive CD4+ T cells," Cancer Res., Sep. 1, 2000, 60(17):4946-4952.

Zeng et al., "CD4(+) T cell recognition of MHC class II-restricted epitopes from NY-ESO-1 presented by a prevalent HLA DP4 allele: association with NY-ESO-1 antibody production," Proceedings of the National Academy of Sciences of the United States of America, Mar. 27, 2001, 98(7):3964-3969.

Zeng et al., "Identification of CD4+ T Cell Epitopes from NY-ESO-1 Presented by HLA-DR Molecules," J Immunol., 165(2):1153-1159.

Zhang et al., "A MAGE-3 peptide presented by HLA-DR1 to CD4+ T cells that were isolated from a melanoma patient vaccinated with a MAGE-3 protein," J Immunol., Jul. 1, 2003, 171(1):219-225.

Zhang et al., "A MAGE-A4 peptide presented by HLA-B37 is recognized on human tumors by cytolytic T lymphocytes," Tissue Antigens., Nov. 2002, 60(5):365-371.

Zorn et al., "A MAGE-6-encoded peptide is recognized by expanded lymphocytes infiltrating a spontaneously regressing human primary melanoma lesion," Eur J Immunol., Feb. 1999, 29(2):602-607.

Zorn et al., "A natural cytotoxic T cell response in a spontaneously regressing human melanoma targets a neoantigen resulting from a somatic point mutation," Eur. J. Immunol., Feb. 1999, 29(2):592-601.

\* cited by examiner gccaccATGCAGATCCCACAGGCGCCCTGGCCAGTCGTCTGGGCGGTGCTACAACTGG
GCTGGCGGCCAGGATGGTTCTTAGACTCCCCAGACAGGCCCTGGAACCCCCCCACC
TTCTCCCCAGCCCTGCTCGTGGTGACCGAAGGGGACAACGCCACCTTCACCTGCAGC
TTCTCCAACACATCGGAGAGCTTCGTGCTAAACTGGTACCGCATGAGCCCCAGCAAC
CAGACGGACAAGCTGGCCGCCTTCCCCGAGGACCGCAGCCAGCCCGGCCAGGACT
GCCGCTTCCGTGTCACACAACTGCCCAACGGGCGTGACTTCCACATGAGCGTGGTCA
GGGCCCGGCGCAATGACAGCGGCACCTACCTCTGTGGGGCCATCTCCCTGGCCCCC
AAGGCGCAGATCAAAGAGAGCCTGCGGGCAGAGCTCAGGGTGACAGAGAGAAGGGC
AGAAGTGCCCACAGCCCACCCCAGCCCCTCACCCAGGCCAGCCGGCCAGTTCCAAA
CCCTGGTGGAGCCTAAGAGCTGCGACAAAACACACTTGCCCACCCTGC
GGAGGAGGCTCTAGCGGAGGAGGGTCTGGAGGCCAGCCAAGAGAGCCCCAGGTGT
ACACACTGCCTCCCTCTCGAGACGAGCTTACAAAGAACCAGGTGTCTCTGACCTGTCT
GGTTAAAGGCTTCTATCCTAGCGACATTGCTGTGGAGTGGGAAAGCAACGGCCAGCC
AGAGAATAACTACAAGACTACACCACCTGTGCTGGACTCTGATGGCAGCTTCTTTCTT
TACAGCAAACTGACAGTTGACAAGTCTAGGTGGCAGCAAGGCAACGTGTTCTCTTGC
AGCGTGATGCACAACCACTACACACAGAAGTCTCTTAGCCTGAGCCCTGGCAAATGA MQIPQAPWPVVWAVLQLGWRPGWFLDSPDRPWNPPTFSPALL
VVTEGDNATFTCSFSNTSESFVLNWYRMSPSNQTDKLAAFPED
RSQPGQDCRFRVTQLPNGRDFHMSVVRARRNDSGTYLCGAISL
APKAQIKESLRAELRVTERRAEVPTAHPSPRPAGQFQTLVE
PKSCDKTHTCPPCGGGSSGGGSGGQPREPQVYTLPPSRDELT
KNQVSLTCLVKGFYPSDIAVEWESNGQPENNYKTTPPVLDSDG
SFFLYSKLTVDKSRWQQGNVFSCSVMHNHYTQKSLSLSPGK
Stop

FIG. 1A

```
Mouse    MWVRQVPWSFTWAVLQLSWQSGWLLEVPNGPWRSLTFYPAWLTVSEGANATFTCSLSNWS
Human    MQIPQAPWPVVWAVLQLGWRPGWFLDSPDRPWNPPTFSPALLVVTEGDNATFTCSFSNTS
Monkey   MQIPQAPWPVVWAVLQLGWRPGWFLESPDRPWNPPTFSPALLLVTEGDNATFTCSFSNAS
         * : *.** ..******.*: **:*: *: **.  ** ** * *:** *******:** *

Mouse    EDLMLNWNRLSPSNQTEKQAAFCNGLSQPVQDARFQIIQLPNRHDFHMNILDTRRNDSGI
Human    ESFVLNWYRMSPSNQTDKLAAFPEDRSQPGQDCRFRVTQLPNGRDFHMSVVRARRNDSGT
Monkey   ESFVLNWYRMSPSNQTDKLAAFPEDRSQPGQDCRFRVTQLPNGRDFHMSVVRARRNDSGT
         *.::*** *:******:* *** .. *** **.**:: **** .****..:: :******

Mouse    YLCGAISLHPKAKIEESPGAELVVTERILETSTRYPSPSPKPEGRFQGMVIGIMSALVGI
Human    YLCGAISLAPKAQIKESLRAELRVTERRAEVPTAHPSPSPRPAGQFQTLVVGVVGGLLGS
Monkey   YLCGAISLAPKAQIKESLRAELRVTERRAEVPTAHPSPSPRPAGQFQALVVGVVGGLLGS
         ******** ***.*.** *** ****  *. * .*****.* *.** .*.*.*...*.*

Mouse    PVLLLLAWALAVFCSTSMSEARGAGSKDDTLKEEPSAAPVPSVAYEELDFQGREKTPELP
Human    --LVLLVWVLAVICSRAARGTIGARRTGQPLKEDPSAVPVFSVDYGELDFQWREKTPEPP
Monkey   --LVLLVWVLAVICSRAAQGTIEARRTGQPLKEDPSAVPVFSVDYGELDFQWREKTPEPP
           *:**.*.***:** :  :  * ..: ***:***.**.** * ***** ****** *

Mouse    TACV--HTEYATIVFTEGLGASAMGRRGSADGLQGPRPPRHEDGHCSWPL
Human    VPCVPEQTEYATIVFPSGMGTSSPARRGSADGPRSAQPLRPEDGHCSWPL
Monkey   APCVPEQTEYATIVFPSGLGTSSPARRGSADGPRSPRPLRPEDGHCSWPL
         . ** .:********.*:*:*:. ******* :. .:* * *********
```

Sequences aligned by Clustal Omega [ebi.ac.uk]

Percent Identity Matrix
Mouse [GenPept Mus Musculus CAA48113.1]          100.00   60.14   61.19
Human [GenPept Homo Sapiens NP_005009.2]          60.14  100.00   96.53
Monkey[GenPept Macaca nemestrina ABR15757.1]      61.19   96.53  100.00

*, amino acid identity; :high amino acid similarity; ., amino acid similarity

FIG. 1B

SEQUENCE LISTING

```
<160> NUMBER OF SEQ ID NOS: 28

<210> SEQ ID NO 1
<211> LENGTH: 11
<212> TYPE: PRT
```

-continued

```
<213> ORGANISM: Artificial Sequence
<220> FEATURE:
<223> OTHER INFORMATION: Description of Artificial Sequence: Synthetic
      peptide

<400> SEQUENCE: 1

Gly Gly Gly Ser Ser Gly Gly Gly Ser Gly Gly
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Gly Gly Ser Ser Gly Gly Gly Ser Gly Ser
1               5                   10

<210> SEQ ID NO 3
<211> LENGTH: 9
<212> TYPE: PRT
<213> ORGANISM: Homo sapiens

<400> SEQUENCE: 3

Leu Leu Met Trp Ile Thr Gln Cys Phe
1               5

<210> SEQ ID NO 4
<211> LENGTH: 9
<212> TYPE: PRT
<213> ORGANISM: Homo sapiens

<400> SEQUENCE: 4

Arg Gly Pro Glu Ser Arg Leu Leu Glu
1               5

<210> SEQ ID NO 5
<211> LENGTH: 9
<212> TYPE: PRT
<213> ORGANISM: Unknown
<220> FEATURE:
<223> OTHER INFORMATION: Description of Unknown:
      survivin sequence

<400> SEQUENCE: 5

Ala Phe Leu Thr Val Lys Lys Gln Met
1               5

<210> SEQ ID NO 6
<211> LENGTH: 180
<212> TYPE: PRT
<213> ORGANISM: Homo sapiens

<400> SEQUENCE: 6

Met Gln Ala Glu Gly Arg Gly Thr Gly Gly Ser Thr Gly Asp Ala Asp
1               5                   10                  15

Gly Pro Gly Gly Pro Gly Ile Pro Asp Gly Pro Gly Gly Asn Ala Gly
            20                  25                  30

Gly Pro Gly Glu Ala Gly Ala Thr Gly Arg Gly Pro Arg Gly Ala
        35                  40                  45

Gly Ala Ala Arg Ala Ser Gly Pro Gly Gly Ala Pro Arg Gly Pro
    50                  55                  60
```

His Gly Gly Ala Ala Ser Gly Leu Asn Gly Cys Cys Arg Cys Gly Ala
65                  70                  75                  80

Arg Gly Pro Glu Ser Arg Leu Leu Glu Phe Tyr Leu Ala Met Pro Phe
                85                  90                  95

Ala Thr Pro Met Glu Ala Glu Leu Ala Arg Arg Ser Leu Ala Gln Asp
            100                 105                 110

Ala Pro Pro Leu Pro Val Pro Gly Val Leu Leu Lys Glu Phe Thr Val
        115                 120                 125

Ser Gly Asn Ile Leu Thr Ile Arg Leu Thr Ala Ala Asp His Arg Gln
    130                 135                 140

Leu Gln Leu Ser Ile Ser Ser Cys Leu Gln Gln Leu Ser Leu Leu Met
145                 150                 155                 160

Trp Ile Thr Gln Cys Phe Leu Pro Val Phe Leu Ala Gln Pro Pro Ser
                165                 170                 175

Gly Gln Arg Arg
            180

<210> SEQ ID NO 7
<211> LENGTH: 752
<212> TYPE: DNA
<213> ORGANISM: Homo sapiens

<400> SEQUENCE: 7
atcctcgtgg gccctgacct tctctctgag agccgggcag aggctccgga gccatgcagg      60
ccgaaggccg gggcacaggg ggttcgacgg gcgatgctga tggcccagga ggccctggca     120
ttcctgatgg cccagggggc aatgctggcg gcccaggaga ggcgggtgcc acgggcggca     180
gaggtccccg gggcgcaggg gcagcaaggg cctcggggcc gggaggaggc gccccgcggg     240
gtccgcatgg cggcgcggct tcagggctga atggatgctg cagatgcggg gccagggggc     300
cggagagccg cctgcttgag ttctacctcg ccatgccttt cgcgacaccc atggaagcag     360
agctggcccg caggagcctg gcccaggatg cccaccgct tcccgtgcca ggggtgcttc     420
tgaaggagtt cactgtgtcc ggcaacatac tgactatccg actgactgct gcagaccacc     480
gccaactgca gctctccatc agctcctgtc tccagcagct ttccctgttg atgtggatca     540
cgcagtgctt tctgcccgtg tttttggctc agcctccctc agggcagagg cgctaagccc     600
agcctggcgc cccttcctag gtcatgcctc ctccccctagg gaatggtccc agcacgagtg     660
gccagttcat tgtgggggcc tgattgtttg tcgctggagg aggacggctt acatgtttgt     720
ttctgtagaa aataaaactg agctacgaaa aa                                    752

<210> SEQ ID NO 8
<211> LENGTH: 254
<212> TYPE: PRT
<213> ORGANISM: Homo sapiens

<400> SEQUENCE: 8

Met Glu Tyr Ala Ser Asp Ala Ser Leu Asp Pro Glu Ala Pro Trp Pro
1               5                   10                  15

Pro Ala Pro Arg Ala Arg Ala Cys Arg Val Leu Pro Trp Ala Leu Val
            20                  25                  30

Ala Gly Leu Leu Leu Leu Leu Leu Ala Ala Ala Cys Ala Val Phe
        35                  40                  45

Leu Ala Cys Pro Trp Ala Val Ser Gly Ala Arg Ala Ser Pro Gly Ser
    50                  55                  60

```
Ala Ala Ser Pro Arg Leu Arg Glu Gly Pro Glu Leu Ser Pro Asp Asp
 65                  70                  75                  80

Pro Ala Gly Leu Leu Asp Leu Arg Gln Gly Met Phe Ala Gln Leu Val
                 85                  90                  95

Ala Gln Asn Val Leu Leu Ile Asp Gly Pro Leu Ser Trp Tyr Ser Asp
            100                 105                 110

Pro Gly Leu Ala Gly Val Ser Leu Thr Gly Gly Leu Ser Tyr Lys Glu
        115                 120                 125

Asp Thr Lys Glu Leu Val Val Ala Lys Ala Gly Val Tyr Tyr Val Phe
    130                 135                 140

Phe Gln Leu Glu Leu Arg Arg Val Val Ala Gly Glu Gly Ser Gly Ser
145                 150                 155                 160

Val Ser Leu Ala Leu His Leu Gln Pro Leu Arg Ser Ala Ala Gly Ala
                165                 170                 175

Ala Ala Leu Ala Leu Thr Val Asp Leu Pro Pro Ala Ser Ser Glu Ala
            180                 185                 190

Arg Asn Ser Ala Phe Gly Phe Gln Gly Arg Leu Leu His Leu Ser Ala
        195                 200                 205

Gly Gln Arg Leu Gly Val His Leu His Thr Glu Ala Arg Ala Arg His
    210                 215                 220

Ala Trp Gln Leu Thr Gln Gly Ala Thr Val Leu Gly Leu Phe Arg Val
225                 230                 235                 240

Thr Pro Glu Ile Pro Ala Gly Leu Pro Ser Pro Arg Ser Glu
                245                 250

<210> SEQ ID NO 9
<211> LENGTH: 870
<212> TYPE: DNA
<213> ORGANISM: Homo sapiens

<400> SEQUENCE: 9
gcgctgtgtc ttcccgcagt ctctcgtcat ggaatacgcc tctgacgctt cactggaccc    60
cgaagccccg tggcctcccg cgccccgcgc tcgcgcctgc cgcgtactgc cttgggccct   120
ggtcgcgggg ctgctgctgc tgctgctgct cgctgccgcc tgcgccgtct tcctcgcctg   180
cccctgggcc gtgtccgggg ctcgcgcctc gcccggctcc gcggccagcc cgagactccg   240
cgagggtccc gagctttcgc ccgacgatcc cgccggcctc ttggacctgc ggcagggcat   300
gtttgcgcag ctggtggccc aaaatgttct gctgatcgat gggcccctga gctggtacag   360
tgacccaggc ctggcaggcg tgtccctgac gggggggctg agctacaaag aggacacgaa   420
ggagctggtg gtggccaagg ctggagtcta ctatgtcttc tttcaactag agctgcggcg   480
cgtggtggcc ggcgagggct caggctccgt ttcacttgcg ctgcacctgc agccactgcg   540
ctctgctgct ggggccgccg ccctggcttt gaccgtggac ctgccacccg cctcctccga   600
ggctcggaac tcggccttcg gtttccaggg ccgcttgctg cacctgagtg ccggccagcg   660
cctgggcgtc catcttcaca ctgaggccag ggcacgccat gcctggcagc ttacccaggg   720
cgccacagtc ttgggactct ccggggtgac ccccgaaatc ccagccggac tcccttcacc   780
gaggtcggaa taacgcccag cctggtgca gcccacctgg acagagtccg aatcctactc   840
catccttcat ggagacccct ggtgctgggt                                     870

<210> SEQ ID NO 10
<211> LENGTH: 309
<212> TYPE: PRT
<213> ORGANISM: Mus musculus
```

<400> SEQUENCE: 10

| | | | | | | | | | | | | | | | |
|---|---|---|---|---|---|---|---|---|---|---|---|---|---|---|---|
|Met|Asp|Gln|His|Thr|Leu|Asp|Val|Glu|Asp|Thr|Ala|Asp|Ala|Arg|His|
|1| | | |5| | | | |10| | | | |15| |
|Pro|Ala|Gly|Thr|Ser|Cys|Pro|Ser|Asp|Ala|Ala|Leu|Leu|Arg|Asp|Thr|
| | | |20| | | | |25| | | | |30| | |
|Gly|Leu|Leu|Ala|Asp|Ala|Ala|Leu|Leu|Ser|Asp|Thr|Val|Arg|Pro|Thr|
| | |35| | | | |40| | | | |45| | | |
|Asn|Ala|Ala|Leu|Pro|Thr|Asp|Ala|Ala|Tyr|Pro|Ala|Val|Asn|Val|Arg|
| |50| | | | |55| | | | |60| | | | |
|Asp|Arg|Glu|Ala|Ala|Trp|Pro|Pro|Ala|Leu|Asn|Phe|Cys|Ser|Arg|His|
|65| | | | |70| | | | |75| | | | |80|
|Pro|Lys|Leu|Tyr|Gly|Leu|Val|Ala|Leu|Val|Leu|Leu|Leu|Leu|Ile|Ala|
| | | | |85| | | | |90| | | | |95| |
|Ala|Cys|Val|Pro|Ile|Phe|Thr|Arg|Thr|Glu|Pro|Arg|Pro|Ala|Leu|Thr|
| | | |100| | | | |105| | | | |110| | |
|Ile|Thr|Thr|Ser|Pro|Asn|Leu|Gly|Thr|Arg|Glu|Asn|Asn|Ala|Asp|Gln|
| | |115| | | | |120| | | | |125| | | |
|Val|Thr|Pro|Val|Ser|His|Ile|Gly|Cys|Pro|Asn|Thr|Thr|Gln|Gln|Gly|
| |130| | | | |135| | | | |140| | | | |
|Ser|Pro|Val|Phe|Ala|Lys|Leu|Leu|Ala|Lys|Asn|Gln|Ala|Ser|Leu|Cys|
|145| | | | |150| | | | |155| | | | |160|
|Asn|Thr|Thr|Leu|Asn|Trp|His|Ser|Gln|Asp|Gly|Ala|Gly|Ser|Ser|Tyr|
| | | | |165| | | | |170| | | | |175| |
|Leu|Ser|Gln|Gly|Leu|Arg|Tyr|Glu|Glu|Asp|Lys|Lys|Glu|Leu|Val|Val|
| | | |180| | | | |185| | | | |190| | |
|Asp|Ser|Pro|Gly|Leu|Tyr|Tyr|Val|Phe|Leu|Glu|Leu|Lys|Leu|Ser|Pro|
| | |195| | | | |200| | | | |205| | | |
|Thr|Phe|Thr|Asn|Thr|Gly|His|Lys|Val|Gln|Gly|Trp|Val|Ser|Leu|Val|
| |210| | | | |215| | | | |220| | | | |
|Leu|Gln|Ala|Lys|Pro|Gln|Val|Asp|Asp|Phe|Asp|Asn|Leu|Ala|Leu|Thr|
|225| | | | |230| | | | |235| | | | |240|
|Val|Glu|Leu|Phe|Pro|Cys|Ser|Met|Glu|Asn|Lys|Leu|Val|Asp|Arg|Ser|
| | | | |245| | | | |250| | | | |255| |
|Trp|Ser|Gln|Leu|Leu|Leu|Lys|Ala|Gly|His|Arg|Leu|Ser|Val|Gly|
| | | |260| | | | |265| | | | |270| | |
|Leu|Arg|Ala|Tyr|Leu|His|Gly|Ala|Gln|Asp|Ala|Tyr|Arg|Asp|Trp|Glu|
| | |275| | | | |280| | | | |285| | | |
|Leu|Ser|Tyr|Pro|Asn|Thr|Thr|Ser|Phe|Gly|Leu|Phe|Leu|Val|Lys|Pro|
| |290| | | | |295| | | | |300| | | | |
|Asp|Asn|Pro|Trp|Glu| | | | | | | | | | | |
|305| | | | | | | | | | | | | | | |

<210> SEQ ID NO 11
<211> LENGTH: 1231
<212> TYPE: DNA
<213> ORGANISM: Mus musculus

<400> SEQUENCE: 11

```
gataaagcac gggcactggc gggagacgtg cactgaccga ccgtggtaat ggaccagcac      60
acacttgatg tggaggatac cgcggatgcc agacatccag caggtacttc gtgcccctcg     120
gatgcggcgc tcctcagaga tacggggctc ctcgcggacg ctgcgctcct ctcagatact     180
gtgcgcccca caaatgccgc gctccccacg gatgctgcct accctgcggt taatgttcgg     240
```

```
gatcgcgagg ccgcgtggcc gcctgcactg aacttctgtt cccgccaccc aaagctctat    300
ggcctagtcg ctttggtttt gctgcttctg atcgccgcct gtgttcctat cttcacccgc    360
accgagcctc ggccagcgct cacaatcacc acctcgccca acctgggtac ccgagagaat    420
aatgcagacc aggtcacccc tgtttcccac attggctgcc ccaacactac acaacagggc    480
tctcctgtgt cgccaagct actggctaaa accaagcat cgttgtgcaa tacaactctg      540
```

```
gatcgcgagg ccgcgtggcc gcctgcactg aacttctgtt cccgccaccc aaagctctat    300
ggcctagtcg ctttggtttt gctgcttctg atcgccgcct gtgttcctat cttcacccgc    360
accgagcctc ggccagcgct cacaatcacc acctcgccca acctgggtac ccgagagaat    420
aatgcagacc aggtcacccc tgtttcccac attggctgcc ccaacactac acaacagggc    480
tctcctgtgt cgccaagct actggctaaa accaagcat cgttgtgcaa tacaactctg      540
aactggcaca gccaagatgg agctgggagc tcataccatt ctcaaggtct gaggtacgaa    600
gaagacaaaa aggagttggt ggtagacagt cccgggctct actacgtatt tttggaactg    660
aagctcagtc caacattcac aaacacaggc cacaaggtgc agggctgggt ctctcttgtt    720
ttgcaagcaa agcctcaggt agatgacttt gacaacttgg ccctgacagt ggaactgttc    780
ccttgctcca tggagaacaa gttagtggac cgttcctgga gtcaactgtt gctcctgaag    840
gctggccacc gcctcagtgt gggtctgagg gcttatctgc atggagccca ggatgcatac    900
agagactggg agctgtctta tcccaacacc accagctttg gactctttct tgtgaaaccc    960
gacaacccat gggaatgaga actatccttc ttgtgactcc tagttgctaa gtcctcaagc   1020
tgctatgttt tatggggtct gagcagggt ccttccatg actttctctt gtctttaact   1080
ggacttggta tttattctga gcatagctca gacaagactt tatataattc actagatagc   1140
attagtaaac tgctgggcag ctgctagata aaaaaaatt tctaaatcaa gtttatatt    1200
tatattaata tataaaaata aatgtgtttg t                                  1231
```

<210> SEQ ID NO 12
<211> LENGTH: 183
<212> TYPE: PRT
<213> ORGANISM: Homo sapiens

<400> SEQUENCE: 12

Met Glu Arg Val Gln Pro Leu Glu Glu Asn Val Gly Asn Ala Ala Arg
1               5                   10                  15

Pro Arg Phe Glu Arg Asn Lys Leu Leu Leu Val Ala Ser Val Ile Gln
            20                  25                  30

Gly Leu Gly Leu Leu Leu Cys Phe Thr Tyr Ile Cys Leu His Phe Ser
        35                  40                  45

Ala Leu Gln Val Ser His Arg Tyr Pro Arg Ile Gln Ser Ile Lys Val
    50                  55                  60

Gln Phe Thr Glu Tyr Lys Lys Glu Lys Gly Phe Ile Leu Thr Ser Gln
65                  70                  75                  80

Lys Glu Asp Glu Ile Met Lys Val Gln Asn Asn Ser Val Ile Ile Asn
                85                  90                  95

Cys Asp Gly Phe Tyr Leu Ile Ser Leu Lys Gly Tyr Phe Ser Gln Glu
            100                 105                 110

Val Asn Ile Ser Leu His Tyr Gln Lys Asp Glu Glu Pro Leu Phe Gln
        115                 120                 125

Leu Lys Lys Val Arg Ser Val Asn Ser Leu Met Val Ala Ser Leu Thr
    130                 135                 140

Tyr Lys Asp Lys Val Tyr Leu Asn Val Thr Thr Asp Asn Thr Ser Leu
145                 150                 155                 160

Asp Asp Phe His Val Asn Gly Gly Glu Leu Ile Leu Ile His Gln Asn
                165                 170                 175

Pro Gly Glu Phe Cys Val Leu
            180

<210> SEQ ID NO 13
<211> LENGTH: 552
<212> TYPE: DNA
<213> ORGANISM: Homo sapiens

<400> SEQUENCE: 13

```
atggaaaggg tccaacccct ggaagagaat gtgggaaatg cagccaggcc aagattcgag      60
aggaacaagc tattgctggt ggcctctgta attcagggac tggggctgct cctgtgcttc     120
acctacatct gcctgcactt ctctgctctt caggtatcac atcggtatcc tcgaattcaa     180
agtatcaaag tacaatttac cgaatataag aaggagaaag gtttcatcct cacttcccaa     240
aaggaggatg aaatcatgaa ggtgcagaac aactcagtca tcatcaactg tgatgggttt     300
tatctcatct ccctgaaggg ctacttctcc caggaagtca acattagcct tcattaccag     360
aaggatgagg agcccctctt ccaactgaag aaggtcaggt ctgtcaactc cttgatggtg     420
gcctctctga cttacaaaga caaagtctac ttgaatgtga ccactgacaa tacctccctg     480
gatgacttcc atgtgaatgg cggagaactg attcttatcc atcaaaatcc tggtgaattc     540
tgtgtccttt ga                                                         552
```

<210> SEQ ID NO 14
<211> LENGTH: 288
<212> TYPE: PRT
<213> ORGANISM: Homo sapiens

<400> SEQUENCE: 14

```
Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240
```

Cys Val Pro Glu Gln Thr Glu Tyr Ala Thr Ile Val Phe Pro Ser Gly
              245                 250                 255

Met Gly Thr Ser Ser Pro Ala Arg Arg Gly Ser Ala Asp Gly Pro Arg
          260                 265                 270

Ser Ala Gln Pro Leu Arg Pro Glu Asp Gly His Cys Ser Trp Pro Leu
      275                 280                 285

<210> SEQ ID NO 15
<211> LENGTH: 2115
<212> TYPE: DNA
<213> ORGANISM: Homo sapiens

<400> SEQUENCE: 15

| | | | | | |
|---|---|---|---|---|---|
| agtttccctt | ccgctcacct | ccgcctgagc | agtggagaag | gcggcactct | ggtggggctg | 60 |
| ctccaggcat | gcagatccca | caggcgccct | ggccagtcgt | ctgggcggtg | ctacaactgg | 120 |
| gctggcggcc | aggatggttc | ttagactccc | cagacaggcc | ctggaacccc | ccacccttct | 180 |
| ccccagccct | gctcgtggtg | accgaagggg | acaacgccac | cttcacctgc | agcttctcca | 240 |
| acacatcgga | gagcttcgtg | ctaaactggt | accgcatgag | ccccagcaac | cagacggaca | 300 |
| agctggccgc | cttccccgag | gaccgcagcc | agcccggcca | ggactgccgc | ttccgtgtca | 360 |
| cacaactgcc | caacgggcgt | gacttccaca | tgagcgtggt | cagggcccgg | cgcaatgaca | 420 |
| gcggcaccta | cctctgtggg | gccatctccc | tggcccccaa | ggcgcagatc | aaagagagcc | 480 |
| tgcgggcaga | gctcagggtg | acagagagaa | gggcagaagt | gcccacagcc | acccccagcc | 540 |
| cctcacccag | gccagccggc | cagttccaaa | ccctggtggt | tggtgtcgtg | gcggcctgc | 600 |
| tgggcagcct | ggtgctgcta | gtctgggtcc | tggccgtcat | ctgctcccgg | gccgcacgag | 660 |
| ggacaatagg | agccaggcgc | accggccagc | ccctgaagga | ggaccnctca | gccgtgcctg | 720 |
| tgttctctgt | ggactatggg | gagctggatt | ccagtggcg | agagaagacc | ccggagcccc | 780 |
| ccgtgccctg | tgtccctgag | cagacggagt | atgccaccat | tgtctttcct | agcggaatgg | 840 |
| gcacctcatc | ccccgcccgc | aggggctcag | ctgacggccc | tcggagtgcc | agccactga | 900 |
| ggcctgagga | tggacactgc | tcttggcccc | tctgaccggc | ttccttggcc | accagtgttc | 960 |
| tgcagaccct | ccaccatgag | cccgggtcag | cgcatttcct | caggagaagc | aggcagggtg | 1020 |
| caggccattg | caggccgtcc | aggggctgag | ctgcctgggg | gcgaccgggg | ctccagcctg | 1080 |
| cacctgcacc | aggcacagcc | ccaccacagg | actcatgtct | caatgcccac | agtgagccca | 1140 |
| ggcagcaggt | gtcaccgtcc | cctacaggga | gggccagatg | cagtcactgc | ttcaggtcct | 1200 |
| gccagcacag | agctgcctgc | gtccagctcc | ctgaatctct | gctgctgctg | ctgctgctgc | 1260 |
| tgctgctgcc | tgcggcccgg | ggctgaaggc | gccgtggccc | tgcctgacgc | cccggagcct | 1320 |
| cctgcctgaa | cttgggggct | ggttggagat | ggccttggag | cagccaaggt | gcccctggca | 1380 |
| gtggcatccc | gaaacgccct | ggacgcaggg | cccaagactg | gcacaggag | tgggaggtac | 1440 |
| atggggctgg | ggactcccca | ggagttatct | gctccctgca | ggcctagaga | agtttcaggg | 1500 |
| aaggtcagaa | gagctcctgg | ctgtggtggg | caggcagga | aaccccctcca | cctttacaca | 1560 |
| tgcccaggca | gcacctcagg | cccttttgtgg | ggcaggaag | ctgaggcagt | aagcgggcag | 1620 |
| gcagagctgg | aggcctttca | ggcccagcca | gcactctggc | ctcctgccgc | cgcattccac | 1680 |
| cccagcccct | cacaccactc | gggagaggga | catcctacgg | tcccaaggtc | aggagggcag | 1740 |
| ggctggggtt | gactcaggcc | cctcccagct | gtggccacct | gggtgttggg | agggcagaag | 1800 |
| tgcaggcacc | tagggccccc | catgtgccca | ccctgggagc | tctccttgga | acccattcct | 1860 |

```
gaaattattt aaagggttg gccgggctcc caccagggcc tgggtgggaa ggtacaggcg    1920
ttccccgggg gcctagtacc cccgccgtgg cctatccact cctcacatcc acacactgca    1980 ccccactcc tggggcaggg ccaccagcat ccaggcggcc agcaggcacc tgagtggctg    2040
ggacaaggga tccccttcc ctgtggttct attatattat aattataatt aaatatgaga    2100
gcatgctaag gaaaa                                                      2115
```

```
<210> SEQ ID NO 16
<211> LENGTH: 900
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
gccaccatgc agatcccaca ggcgccctgg ccagtcgtct gggcggtgct acaactgggc     60
tggcggccag gatggttctt agactcccca gacaggcccg gaaccccccc cacctctcc    120 ccagccctgc tcgtggtgac cgaaggggac aacgccacct tcacctgcag cttctccaac    180
acatcggaga gcttcgtgct aaactggtac cgcatgagcc cagcaacca gacggacaag    240 ctggccgcct ccccgagga ccgcagccag cccggccagg actgccgctt ccgtgtcaca    300
caactgccca cgggcgtga cttccacatg agcgtggtca gggcccggcg caatgacagc    360
ggcacctacc tctgtggggc catctccctg gccccaagg cgcagatcaa agagagcctg    420
cgggcagagc tcagggtgac agagagaagg gcagaagtgc ccacagccca ccccagcccc    480
tcacccaggc cagccggcca gttccaaacc ctggtggagc taagagctg gacaaaaca    540 cacacttgcc caccctgcgg aggaggctct agcggaggag ggtctggagg ccagccaaga    600
gagccccagg tgtacacact gcctccctct cgagacgagc ttacaaagaa ccaggtgtct    660
ctgacctgtc tggttaaagg cttctatcct agcgacattg ctgtggagtg ggaaagcaac    720
ggccagccag agaataacta caagactaca ccacctgtgc tggactctga tggcagcttc    780
tttctttaca gcaaactgac agttgacaag tctaggtggc agcaaggcaa cgtgttctct    840
tgcagcgtga tgcacaacca ctacacacag aagtctctta gcctgagccc tggcaaatga    900
```

```
<210> SEQ ID NO 17
<211> LENGTH: 297
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
```

```
              85                  90                  95
Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
            115                 120                 125

Ala Pro Lys Ala Gln Ile Lys Glu Ser Leu Arg Ala Glu Leu Arg Val
            130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Glu Pro Lys Ser Cys Asp
                165                 170                 175

Lys Thr His Thr Cys Pro Pro Cys Gly Gly Ser Ser Gly Gly Gly
                180                 185                 190

Ser Gly Gly Gln Pro Arg Glu Pro Gln Val Tyr Thr Leu Pro Pro Ser
            195                 200                 205

Arg Asp Glu Leu Thr Lys Asn Gln Val Ser Leu Thr Cys Leu Val Lys
            210                 215                 220

Gly Phe Tyr Pro Ser Asp Ile Ala Val Glu Trp Glu Ser Asn Gly Gln
225                 230                 235                 240

Pro Glu Asn Asn Tyr Lys Thr Thr Pro Pro Val Leu Asp Ser Asp Gly
                245                 250                 255

Ser Phe Phe Leu Tyr Ser Lys Leu Thr Val Asp Lys Ser Arg Trp Gln
                260                 265                 270

Gln Gly Asn Val Phe Ser Cys Ser Val Met His Asn His Tyr Thr Gln
                275                 280                 285

Lys Ser Leu Ser Leu Ser Pro Gly Lys
            290                 295

<210> SEQ ID NO 18
<211> LENGTH: 288
<212> TYPE: PRT
<213> ORGANISM: Homo sapiens

<400> SEQUENCE: 18

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
            35                  40                  45

Asn Ala Thr Phe Thr Cys Ser Phe Ser Asn Thr Ser Glu Ser Phe Val
        50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
            115                 120                 125

Ala Pro Lys Ala Gln Ile Lys Glu Ser Leu Arg Ala Glu Leu Arg Val
            130                 135                 140

Thr Glu Arg Arg Ala Glu Val Pro Thr Ala His Pro Ser Pro Ser Pro
145                 150                 155                 160
```

```
Arg Pro Ala Gly Gln Phe Gln Thr Leu Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
            195                 200                 205

Leu Lys Glu Asp Pro Ser Ala Val Pro Val Phe Ser Val Asp Tyr Gly
            210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
                260                 265                 270

Ser Ala Gln Pro Leu Arg Pro Glu Asp Gly His Cys Ser Trp Pro Leu
            275                 280                 285

<210> SEQ ID NO 19
<211> LENGTH: 288
<212> TYPE: PRT
<213> ORGANISM: Mus musculus

<400> SEQUENCE: 19

Met Trp Val Arg Gln Val Pro Trp Ser Phe Thr Trp Ala Val Leu Gln
1               5                   10                  15

Leu Ser Trp Gln Ser Gly Trp Leu Leu Glu Val Pro Asn Gly Pro Trp
            20                  25                  30

Arg Ser Leu Thr Phe Tyr Pro Ala Trp Leu Thr Val Ser Glu Gly Ala
            35                  40                  45

Asn Ala Thr Phe Thr Cys Ser Leu Ser Asn Trp Ser Glu Asp Leu Met
        50                  55                  60

Leu Asn Trp Asn Arg Leu Ser Pro Ser Asn Gln Thr Glu Lys Gln Ala
65                  70                  75                  80

Ala Phe Cys Asn Gly Leu Ser Gln Pro Val Gln Asp Ala Arg Phe Gln
                85                  90                  95

Ile Ile Gln Leu Pro Asn Arg His Asp Phe His Met Asn Ile Leu Asp
                100                 105                 110

Thr Arg Arg Asn Asp Ser Gly Ile Tyr Leu Cys Gly Ala Ile Ser Leu
            115                 120                 125

His Pro Lys Ala Lys Ile Glu Glu Ser Pro Gly Ala Glu Leu Val Val
            130                 135                 140

Thr Glu Arg Ile Leu Glu Thr Ser Thr Arg Tyr Pro Ser Pro Ser Pro
145                 150                 155                 160

Lys Pro Glu Gly Arg Phe Gln Gly Met Val Ile Gly Ile Met Ser Ala
                165                 170                 175

Leu Val Gly Ile Pro Val Leu Leu Leu Leu Ala Trp Ala Leu Ala Val
            180                 185                 190

Phe Cys Ser Thr Ser Met Ser Glu Ala Arg Gly Ala Gly Ser Lys Asp
            195                 200                 205

Asp Thr Leu Lys Glu Glu Pro Ser Ala Ala Pro Val Pro Ser Val Ala
            210                 215                 220

Tyr Glu Glu Leu Asp Phe Gln Gly Arg Glu Lys Thr Pro Glu Leu Pro
225                 230                 235                 240

Thr Ala Cys Val His Thr Glu Tyr Ala Thr Ile Val Phe Thr Glu Gly
                245                 250                 255
```

```
Leu Gly Ala Ser Ala Met Gly Arg Arg Gly Ser Ala Asp Gly Leu Gln
            260                 265                 270

Gly Pro Arg Pro Pro Arg His Glu Asp Gly His Cys Ser Trp Pro Leu
        275                 280                 285

<210> SEQ ID NO 20
<211> LENGTH: 288
<212> TYPE: PRT
<213> ORGANISM: Macaca nemestrina

<400> SEQUENCE: 20

Met Gln Ile Pro Gln Ala Pro Trp Pro Val Val Trp Ala Val Leu Gln
1               5                   10                  15

Leu Gly Trp Arg Pro Gly Trp Phe Leu Glu Ser Pro Asp Arg Pro Trp
            20                  25                  30

Asn Pro Pro Thr Phe Ser Pro Ala Leu Leu Leu Val Thr Glu Gly Asp
        35                  40                  45

Asn Ala Thr Phe Thr Cys Ser Phe Ser Asn Ala Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Ala Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Gln Gly Thr Ile Glu Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Ala Pro
225                 230                 235                 240

Cys Val Pro Glu Gln Thr Glu Tyr Ala Thr Ile Val Phe Pro Ser Gly
                245                 250                 255

Leu Gly Thr Ser Ser Pro Ala Arg Arg Gly Ser Ala Asp Gly Pro Arg
            260                 265                 270

Ser Pro Arg Pro Leu Arg Pro Glu Asp Gly His Cys Ser Trp Pro Leu
        275                 280                 285

<210> SEQ ID NO 21
<211> LENGTH: 207
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21
```

```
Met Arg Thr Glu Pro Arg Pro Ala Leu Thr Ile Thr Ser Pro Asn
1               5                   10                  15

Leu Gly Thr Arg Glu Asn Asn Ala Asp Gln Val Thr Pro Val Ser His
            20                  25                  30

Ile Gly Cys Pro Asn Thr Thr Gln Gln Gly Ser Pro Val Phe Ala Lys
            35                  40                  45

Leu Leu Ala Lys Asn Gln Ala Ser Leu Cys Asn Thr Thr Leu Asn Trp
50                  55                  60

His Ser Gln Asp Gly Ala Gly Ser Ser Tyr Leu Ser Gln Gly Leu Arg
65                  70                  75                  80

Tyr Glu Glu Asp Lys Lys Glu Leu Val Val Asp Ser Pro Gly Leu Tyr
                85                  90                  95

Tyr Val Phe Leu Glu Leu Lys Leu Ser Pro Thr Phe Thr Asn Thr Gly
            100                 105                 110

His Lys Val Gln Gly Trp Val Ser Leu Val Leu Gln Ala Lys Pro Gln
            115                 120                 125

Val Asp Asp Phe Asp Asn Leu Ala Leu Thr Val Glu Leu Phe Pro Cys
130                 135                 140

Ser Met Glu Asn Lys Leu Val Asp Arg Ser Trp Ser Gln Leu Leu Leu
145                 150                 155                 160

Leu Lys Ala Gly His Arg Leu Ser Val Gly Leu Arg Ala Tyr Leu His
                165                 170                 175

Gly Ala Gln Asp Ala Tyr Arg Asp Trp Glu Leu Ser Tyr Pro Asn Thr
            180                 185                 190

Thr Ser Phe Gly Leu Phe Leu Val Lys Pro Asp Asn Pro Trp Glu
            195                 200                 205

<210> SEQ ID NO 22
<211> LENGTH: 630
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
gccaccatgc gcaccgagcc tcggccagcg ctcacaatca ccacctcgcc caacctgggt     60
acccgagaga taatgcaga ccaggtcacc cctgtttccc acattggctg ccccaacact    120
acacaacagg gctctcctgt gttcgccaag ctactggcta aaaccaagc atcgttgtgc    180 aatacaactc tgaactggca cagccaagat ggagctggga gctcatacct atctcaaggt    240
ctgaggtacg aagaagacaa aaaggagttg gtggtagaca gtcccgggct ctactacgta    300
tttttggaac tgaagctcag tccaacattc acaaacacag ccacaaggt gcagggctgg    360 gtctctcttg ttttgcaagc aaagcctcag gtagatgact tgacaacctt ggccctgaca    420
gtggaactgt tcccttgctc catggagaac aagttagtgg accgttcctg gagtcaactg    480
ttgctcctga aggctggcca ccgcctcagt gtgggtctga ggcttatct gcatggagcc    540 caggatgcat acagagactg ggagctgtct tatcccaaca ccaccagctt tggactcttt    600
cttgtgaaac ccgacaaccc atgggaatga                                    630

<210> SEQ ID NO 23
<211> LENGTH: 21
<212> TYPE: PRT
<213> ORGANISM: Mus musculus
```

-continued

```
<400> SEQUENCE: 23

Met Glu Thr Asp Thr Leu Leu Leu Trp Val Leu Leu Leu Trp Val Pro
1               5                   10                  15

Gly Ser Thr Gly Asp
            20

<210> SEQ ID NO 24
<211> LENGTH: 28
<212> TYPE: PRT
<213> ORGANISM: Unknown
<220> FEATURE:
<223> OTHER INFORMATION: Description of Unknown:
      GCN4 sequence

<400> SEQUENCE: 24

Ile Lys Gln Ile Glu Asp Lys Ile Glu Ile Leu Ser Lys Ile Tyr
1               5                   10                  15

His Ile Glu Asn Glu Ile Ala Arg Ile Lys Lys Leu
            20                  25

<210> SEQ ID NO 25
<211> LENGTH: 197
<212> TYPE: PRT
<213> ORGANISM: Mus musculus

<400> SEQUENCE: 25

Met Glu Gly Glu Gly Val Gln Pro Leu Asp Glu Asn Leu Glu Asn Gly
1               5                   10                  15

Ser Arg Pro Arg Phe Lys Trp Lys Lys Thr Leu Arg Leu Val Val Ser
                20                  25                  30

Gly Ile Lys Gly Ala Gly Met Leu Leu Cys Phe Ile Tyr Val Cys Leu
            35                  40                  45

Gln Leu Ser Ser Ser Pro Ala Lys Asp Pro Pro Ile Gln Arg Leu Arg
        50                  55                  60

Gly Ala Val Thr Arg Cys Glu Asp Gly Gln Leu Phe Ser Ser Tyr Lys
65                  70                  75                  80

Asn Glu Tyr Gln Thr Met Glu Val Gln Asn Asn Ser Val Val Ile Lys
                85                  90                  95

Cys Asp Gly Leu Tyr Ile Ile Tyr Leu Lys Gly Ser Phe Phe Gln Glu
            100                 105                 110

Val Lys Ile Asp Leu His Phe Arg Glu Asp His Asn Pro Ile Ser Ile
        115                 120                 125

Pro Met Leu Asn Asp Gly Arg Arg Ile Val Phe Thr Val Val Ala Ser
    130                 135                 140

Leu Ala Phe Lys Asp Lys Val Tyr Leu Thr Val Asn Ala Pro Asp Thr
145                 150                 155                 160

Leu Cys Glu His Leu Gln Ile Asn Asp Gly Glu Leu Ile Val Val Gln
                165                 170                 175

Leu Thr Pro Gly Tyr Cys Ala Pro Glu Gly Ser Tyr His Ser Thr Val
            180                 185                 190

Asn Gln Val Pro Leu
        195

<210> SEQ ID NO 26
<211> LENGTH: 597
<212> TYPE: DNA
<213> ORGANISM: Mus musculus

<400> SEQUENCE: 26
```

```
atggaagggg aagggttca accctggat gagaatctgg aaaacggatc aaggccaaga      60
ttcaagtgga agaagacgct aaggctggtg gtctctggga tcaagggagc agggatgctt    120
ctgtgcttca tctatgtctg cctgcaactc tcttcctctc cggcaaagga ccctccaatc    180
caaagactca gaggagcagt taccagatgt gaggatgggc aactattcat cagctcatac    240
aagaatgagt atcaaactat ggaggtgcag aacaattcgg ttgtcatcaa gtgcgatggg    300
ctttatatca tctacctgaa gggctccttt ttccaggagg tcaagattga ccttcatttc    360
cgggaggatc ataatcccat ctctattcca atgctgaacg atggtcgaag gattgtcttc    420
actgtggtgg cctcttttggc tttcaaagat aaagtttacc tgactgtaaa tgctcctgat    480
actctctgcg aacacctcca gataaatgat ggggagctga ttgttgtcca gctaacgcct    540
ggatactgtg ctcctgaagg atcttaccac agcactgtga accaagtacc actgtga       597

<210> SEQ ID NO 27
<211> LENGTH: 405
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Met Gly Trp Ser Trp Ile Phe Leu Phe Leu Leu Ser Gly Thr Ala Gly
1               5                   10                  15

Val His Pro Arg Gly Pro Thr Ile Lys Pro Cys Pro Pro Cys Lys Cys
            20                  25                  30

Pro Ala Pro Asn Leu Leu Gly Gly Pro Ser Val Phe Ile Phe Pro Pro
        35                  40                  45

Lys Ile Lys Asp Val Leu Met Ile Ser Leu Ser Pro Ile Val Thr Cys
    50                  55                  60

Val Val Val Asp Val Ser Glu Asp Asp Pro Asp Val Gln Ile Ser Trp
65                  70                  75                  80

Phe Val Asn Asn Val Glu Val His Thr Ala Gln Thr Gln Thr His Arg
                85                  90                  95

Glu Asp Tyr Asn Ser Thr Leu Arg Val Val Ser Ala Leu Pro Ile Gln
            100                 105                 110

His Gln Asp Trp Met Ser Gly Lys Glu Phe Lys Cys Lys Val Asn Asn
        115                 120                 125

Lys Asp Leu Pro Ala Pro Ile Glu Arg Thr Ile Ser Lys Pro Lys Gly
    130                 135                 140

Ser Val Arg Ala Pro Gln Val Tyr Val Leu Pro Pro Pro Glu Glu Glu
145                 150                 155                 160

Met Thr Lys Lys Gln Val Thr Leu Thr Cys Met Val Thr Asp Phe Met
                165                 170                 175

Pro Glu Asp Ile Tyr Val Glu Trp Thr Asn Asn Gly Lys Thr Glu Leu
            180                 185                 190

Asn Tyr Lys Asn Thr Glu Pro Val Leu Asp Ser Asp Gly Ser Tyr Phe
        195                 200                 205

Met Tyr Ser Lys Leu Arg Val Glu Lys Lys Asn Trp Val Glu Arg Asn
    210                 215                 220

Ser Tyr Ser Cys Ser Val Val His Glu Gly Leu His Asn His His Thr
225                 230                 235                 240

Thr Lys Ser Phe Ser Arg Thr Pro Gly Lys Gly Gly Ser Ser Gly
                245                 250                 255
```

Gly Gly Ser Gly Ser Pro Ala Lys Asp Pro Pro Ile Gln Arg Leu Arg
            260                 265                 270

Gly Ala Val Thr Arg Cys Glu Asp Gly Gln Leu Phe Ile Ser Ser Tyr
        275                 280                 285

Lys Asn Glu Tyr Gln Thr Met Glu Val Gln Asn Asn Ser Val Val Ile
    290                 295                 300

Lys Cys Asp Gly Leu Tyr Ile Ile Tyr Leu Lys Gly Ser Phe Phe Gln
305                 310                 315                 320

Glu Val Lys Ile Asp Leu His Phe Arg Glu Asp His Asn Pro Ile Ser
                325                 330                 335

Ile Pro Met Leu Asn Asp Gly Arg Arg Ile Val Phe Thr Val Val Ala
            340                 345                 350

Ser Leu Ala Phe Lys Asp Lys Val Tyr Leu Thr Val Asn Ala Pro Asp
        355                 360                 365

Thr Leu Cys Glu His Leu Gln Asn Asp Gly Glu Leu Ile Val Val Gln
    370                 375                 380

Leu Thr Pro Gly Tyr Cys Ala Pro Glu Gly Ser Tyr His Ser Thr Val
385                 390                 395                 400

Asn Gln Val Pro Leu
                405

<210> SEQ ID NO 28
<211> LENGTH: 1224
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
gccaccatgg gctggtcctg gatcttcctg ttcctgctgt ccggcaccgc cggcgtgcac        60
cctcggggac ccaccatcaa gccctgccct ccctgcaagt gtcccgctcc aacctgctg       120 ggcggcccct ccgtgttcat ctttccaccc aagatcaagg acgtgctgat gatctccctg      180
tctcccatcg tgacctgcgt ggtggtggac gtgtccgagg acgaccccga cgtgcagatc      240
tcctggttcg tgaacaacgt ggaggtgcac accgcccaga cccagaccca ccggaggac       300 tacaactcca ccctgcgggt ggtgtccgcc ctgcccatcc agcaccagga ctggatgtcc      360
ggcaaggagt tcaagtgcaa ggtgaacaac aaggacctgc cgcccccat cgagcggacc       420 atctccaagc ccaagggctc cgtgcgggct ccccaggtgt acgtgctgcc tcctcctgag      480
gaggagatga ccaagaagca ggtgaccctg acctgcatgg tgaccgactt catgcccgag      540
gacatctacg tggagtggac caacaacggc aagaccgagc tgaactacaa gaacaccgag      600
cccgtgctgg actccgacgg ctcctacttc atgtactcca agctgcgggt ggagaagaag      660
aactgggtgg agcggaactc ctactcctgc tccgtggtgc acgagggcct gcacaaccac      720
cacaccacca gtccttctc ccggaccct ggcaagggag gaggctctag cggaggaggg        780
tctggatccc ctgccaagga ccctccccatc agcggctgc ggggcgccgt gacccggtgc      840
gaggacggcc agctgttcat ctcctcctac aagaacgagt accagaccat ggaggtgcag      900
aacaactccg tggtgatcaa gtgcgacggc ctgtacatca tctacctgaa gggctccttc      960
ttccaggagg tgaagatcga cctgcacttc cgggaggacc acaaccccat ctccatcccc     1020

-continued

```
atgctgaacg acggccggcg gatcgtgttc accgtggtgg cctccctggc cttcaaggac   1080
aaggtgtacc tgaccgtgaa cgctcccgac accctgtgcg agcacctgca gaacgacggc   1140
gagctgatcg tggtgcagct gacacccggc tactgcgctc ccgagggctc ctaccactcc   1200
accgtgaacc aggtgcccct gtga                                          1224
```

INDUCTION AND ENHANCEMENT OF ANTITUMOR IMMUNITY INVOLVING SINDBIS VIRUS VECTORS EXPRESSING IMMUNE CHECKPOINT PROTEINS

BACKGROUND OF THE INVENTION

Despite available cancer treatments, which may include aggressive surgical approaches and combination chemotherapeutic regimens, implemented over the past two decades, a variety of cancers routinely evade detection and destruction by cells of the immune system and offer a grim prognosis for patients afflicted with such cancers. Anticancer immunity, including protective immunity, is thought to be based both on the magnitude of the immune response and on the phenotype of the memory immune responses, including T central memory cells (Tcm) and T effector memory cells (Tem). Tcm are characterized by a $CD62L^+$ $CD127^+$ phenotype, whereas Tem are defined by a $CD62L^-$ $CD127^+$ phenotype. Tem traffic through non-lymphoid tissues and exert immediate effector functions in the periphery, while Tcm localize to the secondary lymphoid organs, where they constitute a secondary line of defense by massively expanding upon encounter with antigens presented by dendritic cells. Induction of T cell memory immune responses is dependent on a variety of factors, such as cytokine milieu, length of antigen stimulation, and dose of antigen. $CD8^+$ T cell memory inflation is characterized by the accumulation of high-frequency, functional Ag-specific $CD8^+$ T cell pools with an effector-memory phenotype and enrichment in peripheral organs. This type of response is more vigorous and desirable, for an effective immune response against cancer growth and recurrence.

Sindbis virus (SV) is an oncolytic *Alphavirus* with a positive-stranded RNA genome that can travel systemically through the circulation and kill tumor cells through apoptosis. To date, cancer treatment approaches using oncolytic viruses have not generally led to complete cancer or tumor remission. Moreover, some tumor cells may not be efficiently targeted by viruses used in cancer treatments to date, thus underscoring the need to develop new therapies and additional ways to enhance anticancer treatment.

Immune checkpoint inhibitors, including antibodies against CTLA-4 and PD-1, have been used to block immune inhibitory receptors on activated T-cells, thereby amplifying the immune response. Unfortunately, many patients treated with checkpoint inhibitors ultimately develop resistance to the inhibitors and suffer from disease progression. Given the many hurdles that currently exist in the treatment and prevention of many types of cancers, there exists a profound need for new and improved anti-cancer therapeutic agents, especially those that elicit an immune response directed against tumor and cancer cells, as well as methods for administering such agents to augment the immune response in the treatment and eradication of tumors and cancers in mammals.

SUMMARY OF THE INVENTION

The present invention features a polynucleotide that encodes an *Alphavirus*, lentivirus, or retrovirus protein or a fragment thereof, and an immune checkpoint molecule, such as, without limitation, PD-1, PD-L1, CTLA-4, 4-1BB ligand (4-1BBL), or OX40 ligand (OX40L), or a cognate ligand binding portion or fragment thereof. In an embodiment, the polynucleotide encodes an *Alphavirus* (e.g., Sindbis virus protein or a fragment thereof) and an immune checkpoint molecule or a cognate ligand binding portion or fragment thereof. In an embodiment, the *Alphavirus* is Sindbis virus, a Sindbis virus vector, or viral particle. In an embodiment, the virus is a Sindbis virus vector which contains a polynucleotide that encodes one or more immune checkpoint proteins, or a fragment or portion of the immune checkpoint protein that binds to its cognate ligand, for example and without limitation, the PD-1 immune checkpoint protein or a fragment or portion of PD-1 that binds to its cognate ligand PD-L1. In other embodiments, the virus is a Sindbis virus vector which contains a polynucleotide that encodes one or more immune checkpoint proteins, or a fragment or portion of the immune checkpoint protein that binds to its cognate ligand, for example and without limitation, 4-1BB ligand (4-1BBL), or OX40 ligand (OX40L).

Another feature provided herein is an *Alphavirus* vector, e.g., a Sindbis virus vector, containing a polynucleotide that encodes an immune checkpoint protein, or a fragment or portion of the immune checkpoint protein that binds to its cognate ligand. In an embodiment, the immune checkpoint protein comprises all, or a portion, e.g., the extracellular domain, of a checkpoint protein (also called a "checkpoint molecule" herein). In an embodiment, the checkpoint protein is in the form of a fusion protein, also called a "minibody" herein, in which checkpoint protein or a ligand binding portion of the checkpoint protein, e.g., the extracellular domain, is fused to an immunoglobulin (Ig) hinge region, and an Ig heavy chain constant region domain, such as the CH1, CH2, or CH3 domain of an Ig heavy chain. In an embodiment, the Sindbis virus vector is a component of a therapeutic composition.

In an aspect, a therapeutic composition is provided which comprises a Sindbis virus encoding a fusion polypeptide comprising a secretory signal sequence linked to an immunoglobulin heavy chain constant domain, which is linked to an immune checkpoint protein, or an extracellular domain thereof; wherein the fusion protein comprises one or more linker sequences. In embodiments of the foregoing, the Ig is of the IgG (e.g., IgG1, IgG2a, IgG2b, IgG4 subtypes), IgM, IgA, IgD, or IgE type. In a specific embodiment, the immunoglobulin chain is the IgG1 heavy chain or the IgG2a heavy chain. In an embodiment, the Ig constant region domain is the CH3 domain. In an embodiment, a glycine-rich spacer (or linker) sequence is inserted between the hinge region and the Ig heavy chain CH domain for flexibility. In an embodiment, the spacer (or linker) sequence is or comprises the sequence GGGSSGGGSGG (SEQ ID NO: 1) or GGGSSGGGSGS (SEQ ID NO: 2).

In an embodiment, the *Alphavirus* vector, e.g., Sindbis virus vector or viral particles, encoding an immune checkpoint protein, or a binding portion thereof, is administered to a subject in need, e.g., a subject having a cancer or tumor, e.g., a solid tumor, according to the methods described herein. In an embodiment, the Sindbis virus vector encoding an immune checkpoint protein, or a binding portion thereof, is in a pharmaceutical composition or formulation. In an embodiment, the pharmaceutical composition or formulation comprising the Sindbis virus vector encoding an immune checkpoint protein, or a binding portion thereof, is administered to a subject in need, e.g., a subject having a cancer or tumor, according to the methods described herein. In an embodiment, the Sindbis virus vector encoding an immune checkpoint molecule, or a binding portion thereof, or a pharmaceutical composition comprising the Sindbis virus vector encoding an immune checkpoint molecule, or a binding portion thereof, is administered to a subject in conjunction with another anti-cancer, anti-tumor or chemotherapeutic agent.

In an embodiment, the *Alphavirus* vector, e.g. a Sindbis virus vector, encoding an immune checkpoint molecule, or a binding portion thereof, is administered to a subject in conjunction with one or more checkpoint inhibitor molecules. The one or more checkpoint inhibitor molecules may be administered at the same time as (simultaneously), or at different times from, the administration of the polynucleotides, viral vectors, or viral particles, or pharmaceutical compositions thereof, as described herein. In an embodiment, a checkpoint inhibitor molecule, such as an antibody specifically directed against an immune checkpoint protein, or a fragment thereof that specifically binds to the immune checkpoint protein, is co-administered to a subject in conjunction with the polynucleotides, viral vectors, viral particles, or compositions thereof, particularly, in the methods described herein.

In another embodiment, the *Alphavirus* vector, e.g., Sindbis virus vector, comprises a polynucleotide encoding one or more tumor associated antigens (TAAs) and an immune checkpoint molecule (e.g., PD-1, PD-L1, CTLA-4, OX40, OX40L, 4-1BBL) or a binding portion thereof.

In an embodiment, the Sindbis virus vector or virus particle comprises a polynucleotide that encodes one or multiple (e.g., two or more) epitopes of one or more tumor associated antigens (TAA), wherein each epitope is separated by an enzyme cleavage site. In an embodiment, the viral vector is an *Alphavirus* vector or a pseudotyped *Alphavirus* vector. In a particular embodiment, the viral vector is a Sindbis viral vector. In other embodiments, the viral vector is a retrovirus or lentivirus pseudotyped with one or more *Alphavirus* envelope proteins, e.g., E1, E2, or E3. In other embodiments, the viral vector is a retrovirus or lentivirus pseudotyped with Sindbis virus envelope proteins, such as E1-E3 or ZZ E2. In an embodiment, the epitopes of the tumor associated antigen comprise 5-50 amino acids. In other embodiments, the epitopes of the tumor associated antigen comprise 5-30 amino acids, 5-25 amino acids, 5-20 amino acids, 7-25 amino acids, 7-20, or 7-14 amino acids. In an embodiment, the enzyme cleavage sites comprise sequences that are recognized by an enzyme as described infra.

In an embodiment, the one or more tumor associated antigens (TAAs) are expressed on the surface of a cancer or tumor cell (e.g., extracellularly) or are expressed intracellularly inside a cancer or tumor cell.

In embodiments, TAA epitopes of one or more of the following tumor associated antigens may be encoded by the polynucleotides, viral vectors, or viral particles described herein: kallikrein 4, papillomavirus binding factor (PBF), preferentially expressed antigen of melanoma (PRAME), Wilms' tumor-1 (WT1), Hydroxysteroid Dehydrogenase Like 1 (HSDL1), mesothelin, cancer testis antigen (NY-ESO-1), carcinoembryonic antigen (CEA), p53, human epidermal growth factor receptor 2/neuro receptor tyrosine kinase (Her2/Neu), carcinoma-associated epithelial cell adhesion molecule (EpCAM), ovarian and uterine carcinoma antigen (CA125), folate receptor α, sperm protein 17, tumor-associated differentially expressed gene-12 (TADG-12), mucin-16 (MUC-16), L1 cell adhesion molecule (L1CAM), mannan-MUC-1, Human endogenous retrovirus K (HERV-K-MEL), Kita-kyushu lung cancer antigen-1 (KK-LC-1), human cancer/testis antigen (KM-HN-1), cancer testis antigen (LAGE-1), melanoma antigen-A1 (MAGE-A1), Sperm surface zona pellucida binding protein (Sp17), Synovial Sarcoma, X Breakpoint 4 (SSX-4), Transient axonal glycoprotein-1 (TAG-1), Transient axonal glycoprotein-2 (TAG-2), Enabled Homolog (ENAH), mammoglobin-A, NY-BR-1, Breast Cancer Antigen, (BAGE-1), B melanoma antigen, melanoma antigen-A1 (MAGE-A1), melanoma antigen-A2 (MAGE-A2), mucin k, synovial sarcoma, X breakpoint 2 (SSX-2), Taxol-resistance-associated gene-3 (TRAG-3), Avian Myelocytomatosis Viral Oncogene (c-myc), cyclin B1, mucin 1 (MUC1), p62, survivin, lymphocyte common antigen (CD45), Dickkopf WNT Signaling Pathway Inhibitor 1 (DKK1), telomerase, Kirsten rat sarcoma viral oncogene homolog (K-ras), G250, intestinal carboxyl esterase, alpha-fetoprotein, Macrophage Colony-Stimulating Factor (M-CSF), Prostate-specific membrane antigen (PSMA), caspase 5 (CASP-5), Cytochrome C Oxidase Assembly Factor 1 Homolog (COA-1), O-linked β-N-acetylglucosamine transferase (OGT), Osteosarcoma Amplified 9, Endoplasmic Reticulum Lectin (OS-9), Transforming Growth Factor Beta Receptor 2 (TGF-betaRII), murine leukemia glycoprotein 70 (gp70), Calcitonin Related Polypeptide Alpha (CALCA), Programmed cell death 1 ligand 1 (CD274), Mouse Double Minute 2Homolog (mdm-2), alpha-actinin-4, elongation factor 2, Malic Enzyme 1 (ME1), Nuclear Transcription Factor Y Subunit C (NFYC), G Antigen 1,3 (GAGE-1,3), melanoma antigen-A6 (MAGE-A6), cancer testis antigen XAGE-1b, six transmembrane epithelial antigen of the prostate 1 (STEAP1), PAP, prostate specific antigen (PSA), Fibroblast Growth Factor 5 (FGF5), heat shock protein hsp70-2, melanoma antigen-A9 (MAGE-A9), Arg-specific ADP-ribosyltransferase family C (ARTC1), B-Raf Proto-Oncogene (B-RAF), Serine/Threonine Kinase, beta-catenin, Cell Division Cycle 27 homolog (Cdc27), cyclin dependent kinase 4 (CDK4), cyclin dependent kinase 12 (CDK12), Cyclin Dependent Kinase Inhibitor 2A (CDKN2A), Casein Kinase 1 Alpha 1 (CSNK1A1), Fibronectin 1 (FN1), Growth Arrest Specific 7 (GAS7), Glycoprotein nonmetastatic melanoma protein B (GPNMB), HAUS Augmin Like Complex Subunit 3 (HAUS3), LDLR-fucosyltransferase, Melanoma Antigen Recognized By T-Cells 2 (MART2), myostatin (MSTN), Melanoma Associated Antigen (Mutated) 1 (MUM-1-2-3), Poly(A) polymerase gamma (neo-PAP), myosin class I, Protein phosphatase 1 regulatory subunit 3B (PPP1R3B), Peroxiredoxin-5 (PRDXS), Receptor-type tyrosine-protein phosphatase kappa (PTPRK), Transforming protein N-Ras (N-ras), retinoblastoma-associated factor 600 (RBAF600), sirtuin-2 (SIRT2), SNRPD1, triosephosphate isomerase, Ocular Albinism Type 1 Protein (OA1), member RAS oncogene family (RAB38), Tyrosinase related protein 1-2 (TRP-1-2), Melanoma Antigen Gp75 (gp75), tyrosinase, Melan-A (MART-1), Glycoprotein 100 melanoma antigen (gp100), N-acetylglucosaminyltransferase V gene (GnTVf), Lymphocyte Antigen 6 Complex Locus K (LY6K), melanoma antigen-A10 (MAGE-A10), melanoma antigen-A12 (MAGE-A12), melanoma antigen-C2 (MAGE-C2), melanoma antigen NA88-A, Taxol-resistant-associated protein 3 (TRAG-3), PDZ binding kinase (pbk), caspase 8 (CASP-8), sarcoma antigen 1 (SAGE), Breakpoint Cluster Region-Abelson oncogene (BCR-ABL), fusion protein in leukemia, dek-can, Elongation Factor Tu GTP Binding Domain Containing 2 (EFTUD2), ETS Variant gene 6/acute myeloid leukemia fusion protein (ETV6-AML1), FMS-like tyrosine kinase-3 internal tandem duplications (FLT3-ITD), cyclin-A1, Fibronectin Type III Domain Containing 3B (FDNC3B,) promyelocytic leukemia/retinoic acid receptor alpha fusion protein (pml-RARalpha), melanoma antigen-C1 (MAGE-C1), membrane protein alternative spliced isoform (D393-CD20), melanoma antigen-A4 (MAGE-A4), or melanoma antigen-A3 (MAGE-A3).

In some embodiments, the virus vector contains a polynucleotide which encodes the TAA NY-ESO-1, the tumor associated antigen MAGE-A3 and/or the tumor associated antigen pbk, or epitopes thereof. In a particular embodiment, the virus vector contains a polynucleotide that encodes an epitope from the tumor associated antigen NY-ESO-1 comprising the amino acid sequence LLMWITQCF (SEQ ID NO: 3). In an embodiment, the virus vector contains a polynucleotide that encodes the tumor associated antigen survivin or an epitope thereof. In a particular embodiment, the virus vector contains a polynucleotide that encodes an epitope from the tumor associated antigen NY-ESO-1 comprising the amino acid sequence RGPESRLLE (SEQ ID NO: 4). In another embodiment, the virus vector contains a polynucleotide that encodes the tumor associated antigen survivin comprising the amino acid sequence AFLTVKKQM (SEQ ID NO: 5).

In embodiments, the virus vector contains a polynucleotide that encodes a checkpoint protein that binds to a cognate ligand (a receptor protein) that is expressed on the surface of a cancer or tumor cell, or in the cytosol of a cancer or tumor cell, of a/an ovarian cancer, breast cancer, testicular cancer, pancreatic cancer, liver cancer, colon cancer, colorectal cancer, thyroid cancer, lung cancer, prostate cancer, kidney cancer, melanoma, squamous cell carcinoma, chronic myeloid leukemia, acute lymphoblastic leukemia, acute myelogenous leukemia, chronic lymphocytic leukemia, promyelocytic leukemia, multiple myeloma, B-cell lymphoma, bladder carcinoma, head and neck cancer, esophageal cancer, brain cancer, pharynx cancer, tongue cancer, synovial cell carcinoma, neuroblastoma, uterine cancer, fibrosarcoma, myxosarcoma, liposarcoma, chondrosarcoma, osteogenic sarcoma, chordoma, angiosarcoma, endotheliosarcoma. lymphangiosarcoma, synovioma, mesothelioma, Ewing's tumor, leiomyosarcoma, rhabdomyosarcoma, basal cell carcinoma, epidermoid carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms'•tumor, cervical cancer, small cell lung carcinoma, epithelial carcinoma, glioma, astrocytoma, medulloblastoma, craniopharyngioma, ependymoma, pinealoma, hemangioblastoma, acoustic neuroma, oligodendroglioma, meningioma, neuroglioma, or retinoblastoma.

In an embodiment, the polynucleotide encodes one or more immunostimulatory or immunomodulatory proteins. By way of example, such proteins include, without limitation, one or more of IL-1, IL-2, IL-3, IL-4, IL-5, IL-6 IL-7, IL-8, IL-9, IL-10, IL-11, IL-12, IL-13, IL-14, IL-15, IL-16, IL-17, IL-18, IL-19, IL-20 through IL-36, chemokine CCL1 through CCL27, CC chemokine CXCL1 through CXCL13, a CXC chemokine, a C chemokine, a CX3C chemokine, a cytokine or chemokine receptor, a soluble receptor, Transforming Growth Factor-beta (TGF-β), or Tumor Necrosis Factor-alpha (TNFα).

In another of its aspects, the present invention is directed to a viral vector comprising the polynucleotide as described supra and infra. In embodiments, the viral vector is selected from an *Alphavirus*, a lentivirus, or a retrovirus. In an embodiment, the viral vector is pseudotyped with one or more *Alphavirus* virus envelope proteins. In an embodiment, the viral vector is pseudotyped with *Alphavirus* E1 protein, E2 protein, both the E1 and the E2 proteins, or a fragment thereof. In a particular embodiment, the viral vector is a Sindbis viral vector or is derived from Sindbis virus. In an embodiment, the viral vector is pseudotyped with one or more Sindbis virus envelope proteins. In an embodiment, the viral vector is pseudotyped with Sindbis-ZZ E2 protein or a fragment thereof. In a particular embodiment, the viral vector is a lentivirus pseudotyped with one or more Sindbis virus envelope proteins, which may include the Sindbis-ZZ E2 protein. In a particular embodiment, the viral vector is a retrovirus pseudotyped with one or more Sindbis virus envelope proteins, which may include the Sindbis-ZZ E2 protein. In an embodiment, the viral vector is a replication-defective viral vector. In an embodiment, the viral vector is a replication-competent viral vector. In an embodiment, the viral vector is a non-integrating viral vector.

In a particular aspect, a Sindbis viral vector is provided which comprises a polynucleotide encoding an immune checkpoint molecule or a cognate ligand binding portion thereof. In an embodiment, the virus vector comprises a polynucleotide encoding a tumor associated antigen (TAA), or one or more epitopes comprising 5-30 amino acids of a tumor associated antigen (TAA), wherein each epitope is separated by a furin enzyme cleavage site. In another particular aspect, the viral vector is pseudotyped with one or more Sindbis virus envelope proteins.

In an embodiment, the viral vector, e.g., the Sindbis virus vector, encoding a checkpoint protein, or a cognate ligand binding portion thereof, elicits an immune response against a tumor or cancer following administration to a subject, preferably a human subject or patient who has a cancer or tumor. In an embodiment, the administration of the viral vector, e.g., the Sindbis virus vector, encoding a checkpoint protein, or a cognate ligand binding portion thereof, increases the survivability of the subject having cancer or a tumor. In an embodiment, the Sindbis viral vector or the pseudotyped viral vector contains the polynucleotide described supra and infra. In an embodiment, the Sindbis viral vector or the pseudotyped viral vector contains a polynucleotide sequence encoding a minibody which comprises a checkpoint protein fusion molecule, or a ligand binding portion thereof, as described herein, whose encoded products are expressed in cells and secreted by cells following contact of the viral vector with cells in vitro and in vivo.

Provided as another aspect of the invention is a lentiviral vector pseudotyped with one or more genetically engineered Sindbis virus envelope proteins, in which the lentiviral vector comprises the polynucleotide as described supra and infra. Also provided by the invention is a lentiviral vector pseudotyped with one or more genetically engineered Sindbis virus envelope proteins, said lentiviral vector comprising the polynucleotide as described supra and infra, wherein the polynucleotide encodes a checkpoint protein or a ligand binding portion thereof.

In another aspect, the invention provides a viral particle comprising the viral vector, such as the Sindbis viral vector or the pseudotyped viral vector as described supra and infra. In another aspect, the invention provides a viral particle comprising an *Alphavirus* vector, a lentiviral vector, a retroviral vector, or a pseudotyped vector thereof as described supra and infra.

In another aspect, the invention provides a cell comprising a polynucleotide as described supra and infra. In other aspects, the invention further provides a cell comprising a viral vector or a lentiviral vector as described supra and infra. In an aspect, the invention provides a cell comprising a viral particle as described supra and infra.

In yet another aspect, pharmaceutical compositions are provided which comprise a polynucleotide, viral particle, and/or viral vector as described supra and infra, and a pharmaceutically acceptable vehicle, carrier, or diluent. In an embodiment, the pharmaceutical composition is in liquid dosage form.

In another aspect, a method of inducing an immune response against a cancer or tumor cell, e.g., a cancer or tumor cell that expresses one or more tumor associated antigens or epitopes thereof, is provided in which the method involves contacting the cancer or tumor cell with an effective amount of a polynucleotide, viral particle, viral vector, and/or pharmaceutical composition as described supra and infra, such as a Sindbis viral vector containing a polynucleotide that encodes a checkpoint protein or a ligand binding fragment thereof, or a checkpoint protein minibody as described herein, to induce an immune response against the cancer or tumor cell. In an embodiment, the immune response involves the generation of activated cytotoxic T cells that specifically kill the cancer or tumor cells that express the cognate ligand (e.g., protein receptor) that interacts with the vector-encoded checkpoint protein. Nonlimiting examples of immune checkpoint proteins include PD-1, PD-L1, OX40, OX40 ligand (OX40-L), CTLA-4, 4-1BB, 4-1BB ligand (4-1BBL), KIR, LAG-3, IDO1, TIM-3, A2AR, B7-H3, B7-H4, B7-1/B7-2, BTLA, VISTA, or a cognate ligand binding portion thereof. In a specific embodiment, the immune checkpoint proteins include PD-1, PD-L1, OX40 and CTLA-4. In another aspect, a method of treating cancer or a tumor in a subject who has, or is at risk or having, cancer or tumorigenesis is provided, in which the method involves administering to the subject a therapeutically effective amount of a polynucleotide, viral particle, viral vector, and/or pharmaceutical composition as described supra and infra to treat the cancer or tumor in the subject. In an embodiment of the foregoing methods, the subject is preferably a human patient having or at risk of having a cancer or tumor selected from one or more of a/an ovarian cancer, cervical cancer, uterine cancer, breast cancer, testicular cancer, pancreatic cancer, liver cancer, colorectal cancer, colon cancer, thyroid cancer, lung cancer, prostate cancer, kidney cancer, melanoma, squamous cell carcinoma, chronic myeloid leukemia, acute lymphoblastic leukemia, acute myelogenous leukemia, chronic lymphocytic leukemia, promyelocytic leukemia, multiple myeloma, B-cell lymphoma, bladder carcinoma, head and neck cancer, esophageal cancer, brain cancer, pharynx cancer, tongue cancer, synovial cell carcinoma, neuroblastoma, fibrosarcoma, myxosarcoma, liposarcoma, chondrosarcoma, osteogenic sarcoma, chordoma, angiosarcoma, endotheliosarcoma. lymphangiosarcoma, synovioma, mesothelioma, Ewing's tumor, leiomyosarcoma, rhabdomyosarcoma, basal cell carcinoma, epidermoid carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms'•tumor, small cell lung carcinoma, epithelial carcinoma, glioma, astrocytoma, medulloblastoma, craniopharyngioma, ependymoma, pinealoma, hemangioblastoma, acoustic neuroma, oligodendroglioma, meningioma, neuroglioma, or retinoblastoma. In a particular embodiment of the methods, the subject's cancer is colon cancer. In an embodiment of the methods, the polynucleotide, viral particle, viral vector, or pharmaceutical composition is administered parenterally (e.g., intravenously or intraperitoneally) or as a prophylactic. In embodiments of the methods, the subject is further treated with an anti-cancer or tumor agent, chemotherapy, or radiation.

A particular aspect of the invention provides a non-integrating *Alphavirus* vector (e.g., a Sindbis viral vector) molecularly engineered to contain a polynucleotide which encodes at least one immune checkpoint protein, or a cognate ligand binding portion thereof, or a checkpoint protein-Ig fusion protein (called a minibody) as described and exemplified herein. In an embodiment, the vector also contains a polynucleotide which encodes a tumor associated antigen (TAA) or one or more epitopes thereof. By way of example, the TAA epitope may comprise 5-50 amino acids or 5-30 amino acids. In an embodiment, if more than one tumor associated antigen or epitope thereof is encoded by the vector, each epitope sequence may be separated by a processing site, such as an enzyme cleavage site, e.g., a furin enzyme cleavage site, for reproducibility in intracellular processing of the tumor associated antigen epitope polypeptide and peptide products. In some embodiments, the viral vector also contains one or more nucleic acid sequences which encode one or more neo-antigens, cytokines, chemokines, antibodies, mutated oncogenes, or overexpressed oncogenes, for enhancing and improving the immune response against the tumor associated antigen epitopes that is elicited by the viral vectors and viral particles described herein, as well as the therapeutic and/or prophylactic uses thereof.

In an aspect, because the Sindbis viral vectors as described herein elicit strong T cell responses, including CD8+ T cell responses, a checkpoint protein-encoding sequence may be combined with TAA epitope-encoding sequences in the described polynucleotides and *Alphavirus* and Sindbis virus vectors. This may augment anti-tumor efficacy for T cells in an immune response resulting from treatment with the viral vectors as described and exemplified herein.

In another aspect, the *Alphavirus* protein or a fragment thereof, or envelope protein or fragment thereof, of the polynucleotides, viral vectors, or viral particles as described herein is derived from one or more of Barmah Forest virus, Barmah Forest virus complex, Eastern equine encephalitis virus (EEEV), Eastern equine encephalitis virus complex, Middelburg virus, Middelburg virus complex, Ndumu virus, Ndumu virus complex, Semliki Forest virus, Semliki Forest virus complex, Bebaru virus, Chikungunya virus, Mayaro virus, Subtype Una virus, O'Nyong Nyong virus, Subtype Igbo-Ora virus, Ross River virus, Subtype Getah virus, Subtype Bebaru virus, Subtype Sagiyama virus, Subtype Me Tri virus, Venezuelan equine encephalitis virus (VEEV), VEEV complex, Cabassou virus, Everglades virus, Mosso das Pedras virus, Mucambo virus, Paramana virus, Pixuna virus, Western equine encephalitis virus (WEEV), Rio Negro virus, Trocara virus, Subtype Bijou Bridge virus, Western equine encephalitis virus complex, Aura virus, Babanki virus, Kyzylagach virus, Sindbis virus, Ockelbo virus, Whataroa virus, Buggy Creek virus, Fort Morgan virus, Highlands J virus, Eilat virus, Salmon pancreatic disease virus (SPDV), Southern elephant seal virus (SESV), Tai Forest virus, or Tonate virus.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "NY-ESO-1 protein" is meant a polypeptide having at least 85% amino acid sequence identity to UniProtKB-P78358 (CTG1B_Human) or a fragment thereof. An exemplary NY-ESO-1 amino acid sequence is provided below:

```
                                            (SEQ ID NO: 6)
MQAEGRGTGG STGDADGPGG PGIPDGPGGN AGGPGEAGAT

GGRGPRGAGA ARASGPGGGA PRGPHGGAAS GLNGCCRCGA

RGPESRLLEF YLAMPFATPM EAELARRSLA QDAPPLPVPG

VLLKEFTVSG NILTIRLTAA DHRQLQLSIS SCLQQLSLLM

WITQCFLPVF LAQPPSGQRR
```

By "NY-ESO-1 polynucleotide" is meant a nucleic acid molecule encoding an NY-ESO-1 protein. An exemplary NY-ESO-1 polynucleotide sequence is provided below:

```
                                             (SEQ ID NO: 7)
  1  atcctcgtgg gccctgacct tctctctgag agccgggcag aggctccgga gccatgcagg 61  ccgaaggccg gggcacaggg ggttcgacgg gcgatgctga tggcccagga ggccctggca 121  ttcctgatgg cccagggggc aatgctggcg gcccaggaga ggcgggtgcc acggcggca 181  gaggtccccg gggcgcaggg gcagcaaggg cctcggggcc gggaggaggc gccccgcggg 241  gtccgcatgg cggcgcggct tcagggctga atggatgctg cagatgcggg gccaggggc 301  cggagagccg cctgcttgag ttctacctcg ccatgccttt cgcgacaccc atggaagcag 361  agctggcccg caggagcctg gcccaggatg ccccaccgct tcccgtgcca ggggtgcttc 421  tgaaggagtt cactgtgtcc ggcaacatac tgactatccg actgactgct gcagaccacc 481  gccaactgca gctctccatc agctcctgtc tccagcagct ttccctgttg atgtggatca 541  cgcagtgctt tctgccgtg ttttggctc agcctccctc agggcagagg cgctaagccc
```

601  agcctggcgc cccttcctag gtcatgcctc ctccctagg gaatggtccc agcacgagtg 661  gccagttcat tgtgggggcc tgattgtttg tcgctggagg aggacggctt acatgtttgt 721  ttctgtagaa aataaaactg agctacgaaa aa By "agent" is meant a peptide, polypeptide, nucleic acid molecule, or small molecule chemical compound, antibody, or a fragment thereof. In one embodiment, the agent is a Sindbis virus, is a checkpoint inhibitor (e.g., an anti-PD1 antibody or anti-CTLA4 antibody), or is a therapeutic composition comprising a Sindbis virus (e.g., a Sindbis virus encoding a tumor associated antigen or fragment thereof (e.g., epitope) and a checkpoint inhibitor.

By "alteration" is meant a change (increase or decrease) in an analyte. In one embodiment an alteration is in the expression levels or activity of a gene or polypeptide as detected by standard art known methods such as those described herein. As used herein, an alteration includes a 10% change in expression levels, a 25% change, a 40% change, or a 50% or greater change in expression levels.

By "ameliorate" and "amelioration" is meant decrease, suppress, attenuate, diminish, arrest, or stabilize the development or progression of a disease.

By "analog" or "derivative" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

As used herein, the term "antigen" refers to a substance capable of eliciting a humoral or cell-mediated immune response. An antigen may be capable, e.g., of inducing the generation of antibodies or stimulating T-cell activity through activation of a T-cell receptor. Antigens are typically proteins or polysaccharides, and may be components of bacteria, viruses, and other microorganisms (e.g., coats, capsules, cell walls, capsids, flagella, and toxins). The term as used herein encompasses all substances that can be recognized by the adaptive and innate immune system and by an antibody or antibody fragment in vitro or in vivo.

The term "antibody" refers to a polypeptide encoded by an immunoglobulin gene or fragments thereof that specifically bind a cognate antigen. Immunoglobulin genes typically include variable region genes of the light and heavy chains; the kappa and lambda light chain constant region genes, and the alpha, gamma, delta, epsilon, and mu heavy chain constant region genes, which correspond to the immunoglobulin classes, IgA, IgG, IgD, IgE and IgM, respectively. An exemplary immunoglobulin (antibody) structural unit comprises a tetramer. Each tetramer is composed of two identical pairs of polypeptide chains, each pair having one "light" (about 2 kDa) and one "heavy" chain (up to about 70 kDa). Antibodies exist, for example, as intact immunoglobulins or as a number of well-characterized fragments produced by digestion with various peptidases. While various antibody fragments are defined in terms of the digestion of an intact antibody, one of skill in the art will appreciate that such fragments may be synthesized de novo chemically or via recombinant DNA methodologies. Thus, the term antibody, as used herein, also includes antibody fragments produced by the modification of whole antibodies, those synthesized de novo using recombinant DNA methodologies (for example, single chain Fv), monoclonal antibodies or humanized antibodies, and those identified using phage display libraries (see, for example, McCafferty et al., *Nature,* 348:2-4, 1990), for example. For preparation of antibodies, e.g., recombinant or monoclonal antibodies, any technique known in the art can be used, for example, Kohler & Milstein, *Nature,* 256 (5517):495-497, 1975; Kozbor et al., *Immunology Today,* 4:72, 1983; Cole et al., pp. 77-96 in *Monoclonal Antibodies and Cancer Therapy,* Alan R. Liss, Inc., 1998). In addition, techniques for the production of single chain antibodies (See, U.S. Pat. No. 4,946,778) can be adapted to produce antibodies to proteins and polypeptides, such as immune checkpoint proteins. Transgenic mice, or other organisms, for example, other mammals, can be used to express humanized antibodies. Phage display technology also can be used to identify antibodies and heteromeric Fab fragments that specifically bind to selected proteins, e.g., checkpoint inhibitor proteins (see, e.g., McCafferty et al., 1990, *Nature,* 348:2-4; Marks et al., 1992, *Biotechnology,* 10 (7):779-783; and Knappik et al., 2000, *J. Mol. Biol.,* 296: 57-86.

As used herein, the term "at risk" as it applies to a cell proliferation disease, such as cancer (e.g., a cancer described herein), refers to patients who have undergone tumor debulking surgery or individuals who have a family history of cancer and/or have been diagnosed as having genetic risk factor genes.

As used herein, the term "carrier" refers to a diluent, adjuvant, excipient, or vehicle with which a composition or pharmaceutical composition, e.g., comprising a polynucleotide, viral vector, or viral particle) can be administered. Pharmaceutical and pharmaceutically acceptable carriers include sterile liquids, such as water and oils, including those of petroleum, animal, vegetable or synthetic origin, such as peanut oil, soybean oil, mineral oil, sesame oil, and the like. Water or aqueous saline solutions and aqueous dextrose and glycerol solutions may be employed as carriers, particularly for injectable solutions. Carriers may also include solid dosage forms, including, but not limited to, one or more of a binder (for compressed pills), a glidant, an encapsulating agent, a flavorant, and a colorant. Suitable pharmaceutical carriers are described in "Remington's Pharmaceutical Sciences" by E. W. Martin.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

As will be appreciated by one skilled in the art, "derived from" refers to obtaining from, originating from, or producing from, all or a portion of, (typically a functional or active portion of), a polynucleotide, a polypeptide, or a peptide from a source, e.g., a virus, bacterium, microorganism, or a biological source.

By "immune checkpoint protein" or "immune checkpoint molecule," or simply, "checkpoint protein or molecule" is meant a protein or molecule that can either induce or hinder activation of T cells, or a particular process in a cellular or immune system pathway, e.g., to prevent errors or an abnormal or pathological activity or condition. In an immune response, the crucial interaction between antigen presenting cells (APCs) and T-cells is tightly regulated by a 'three signal model:' (1) display of a surface complex consisting of an antigen bound on a major histocompatibility complex (MHC) protein class I or II (MHC I or II) molecule to a T-cell receptor (TCR) on a T-cell (CD8+ or CD4+); (2) costimulation by immune checkpoint proteins and (3) cytokines. Immune checkpoint proteins comprise costimulatory and inhibitory proteins that can either induce or inhibit activation of T-cells. Naive T-cells that only receive signal 1 without costimulatory signal 2 become anergic or die through apoptosis. The engagement of costimulatory ligand/receptor pairs triggers an accumulation of receptors and protein complexes at the center of the immunological synapse, which then amplifies and enhances the duration of TCR signaling (Wulfing, C. and Davis, M. M., 1998, *Science,* 282:2266-2269). The cytokine environment, signal 3, then induces naïve CD4+ T-cells to differentiate into various T-cell subsets, such as T helper (Th)1 cells, Th2 cells, Th17 cells and regulatory T-cells (Tregs), each of which produce and release a distinct set of cytokines upon activation. (Foks, A. C. and Kuiper, J., 2017, *Br. J. Pharmacol.,* 174:3940-3955).

The immune system provides a large variety of stimulatory and inhibitory immune checkpoint proteins (signal 2), and each pathway has its own unique effect on the fate of individual immune cells. Signaling through stimulatory immune checkpoint proteins can promote cell survival, cell cycle progression and differentiation to effector and memory cells, while inhibitory immune checkpoint protein signaling can terminate these processes directly or indirectly by the induction of Tregs. Costimulation can be provided in cis, i.e., both signals 1 and 2 are provided by the same APC, or in trans, i.e., signal 2 is provided by a different or 'bystander' APC than signal 1 (Roska, A. K. and Lipsky, P. E., 1985, *J. Immunol.,* 135:2953-2961; Liu, Y. and Janeway, C. A., Jr., 1992, *Proc. Natl. Acad. Sci. USA,* 89:3845-3849; Ding, L. and Shevach, E. M., 1994, *Eur. J. Immunol.,* 24:859-866).

Checkpoint proteins are regulators of the immune system and frequently bound by or interact with ligands (cognate ligands), which may cause a given effect, e.g., cell stimulation, anergy, or apoptosis. Nonlimiting examples of checkpoint proteins expressed on T cells include, PD-1, CD28, CTLA4, ICOS, TMIGD2, 4-1BB, 4-1BB ligand (4-1BBL), BTLA, CD160, LIGHT, LAG3, OX40, OX40 ligand (OX40L), CD27, CD40 ligand (CD40L), GITR, DNAM-1, TIGIT, CD96, 2B4, TIM-3, Adenosine A2a receptor (AA2R), CEACAM1, SIRP alpha, DC-SIGN, CD200R and DR3. Nonlimiting examples of checkpoint proteins expressed on tumor cells include PD-L1, PD-L2, CD80 (B7-1), CD86 (B7-2), ICOS Ligand, B7-H3, B7-H4, VISTA, B7-H7 (HHLA2), 4-1BBL, HVEM, MHC class I and II, OX40L, CD70, CD40, GITRL, CD155, CD48, Galectin-9, Adenosine, IDO, TDO, CEACAM1, CD47, BTN2A1, CD200 and TL1A. Checkpoint proteins bind to their cognate ligands, which may be receptor proteins expressed on a cell. Checkpoint protein and ligand binding molecule interactions include the following interacting binding protein pairs or combinations, without limitation, PD-1/PD-L1 or PD-L2; CD28/CD80 (B7-1) or CD86 (B7-2); CTLA4/CD80 (B7-1) or CD86 (B7-2); ICOS/ICOS Ligand; TMIGD2/B7-H7 (HHLA2); 4-1BB/4-1BBL; BTLA/HVEM; CD160/HVEM; LIGHT/HVEM; LAG3/MHC class I or II; OX40/OX40L; CD27/CD70; CD40L/CD40; GITR/

GITRL; DNAM-1/CD155; TIGIT/CD155; CD96/CD155; 2B4/CD48; TIM-3/Galactin-9; Adenosine A2a receptor/Adenosine; CEACAM1/CEACAM1; SIRP alpha/CD47; DC-SIGN/BTN2A1; CD200R/CD200; and DR3/TL1A. In a specific embodiment, the immune checkpoint proteins include PD-1, PD-L1, OX40, OX40L, 4-1BBL and CTLA-4.

Checkpoint molecules, such as, without limitation, CD28, OX40, GITR, CD137, CD27, or HVEM, may be categorized as activating costimulatory molecules or receptors expressed on T cells. Binding of activating costimulatory molecules or receptors by antibodies ("agonistic antibodies") stimulates the activity of T cells, thereby promoting an immune response or an anti-tumor response. In addition, checkpoint molecules, such as, without limitation, CTLA-4, PD-1, TIM-3, BTLA, VISTA, or LAG-3, may be categorized as negative costimulatory molecules or inhibitory receptors expressed on T cells. Binding of negative costimulatory molecules or inhibitory receptors by antibodies ("blocking or antagonistic antibodies") blocks the inhibition of activity of T cells, thereby promoting an immune response, such as an anti-tumor response.

By "4-1BB ligand (4-1BBL)" (also called TNFSF9 ligand) is meant a polypeptide having at least 85% amino acid sequence identity, or at least 90% amino acid sequence, or at least 95% amino acid sequence identity, or at least 98% amino acid sequence identity to the human amino acid sequence (Accession No. P41273), or a fragment thereof, shown below:

(SEQ ID NO: 8)
MEYASDASLDPEAPWPPAPRARACRVLPWALVAGLLLLLLLAAACAVFLA

CPWAVSGARASPGSAASPRLREGPELSPDDPAGLLDLRQGMFAQLVAQNV

LLIDGPLSWYSDPGLAGVSLTGGLSYKEDTKELVVAKAGVYYVFFQLELR

RVVAGEGSGSVSLALHLQPLRSAAGAAALALTVDLPPASSEARNSAFGFQ

GRLLHLSAGQRLGVHLHTEARARHAWQLTQGATVLGLFRVTPEIPAGLPS

PRSE.

By "4-1BBL polynucleotide" is meant a nucleic acid molecule encoding a human 4-1BBL protein. By way of example, a full-length, human 4-1BBL polynucleotide sequence (cDNA), (Accession No. BC104807.1), is provided below:

(SEQ ID NO: 9)
GCGCTGTGTCTTCCCGCAGTCTCTCGTCATGGAATACGCCTCTGACGCTT

CACTGGACCCCGAAGCCCCGTGGCCTCCCGCGCCCCGCGCTCGCGCCTGC

CGCGTACTGCCTTGGGCCCTGGTCGCGGGGCTGCTGCTGCTGCTGCTGCT

CGCTGCCGCCTGCGCCGTCTTCCTCGCCTGCCCCTGGGCCGTGTCCGGGG

CTCGCGCCTCGCCCGGCTCCGCGGCCAGCCCGAGACTCCGCGAGGGTCCC

GAGCTTTCGCCCGACGATCCCGCCGGCCTCTTGGACCTGCGGCAGGGCAT

GTTTGCGCAGCTGGTGGCCCAAAATGTTCTGCTGATCGATGGGCCCCTGA

GCTGGTACAGTGACCCAGGCCTGGCAGGCGTGTCCCTGACGGGGGGCCTG

AGCTACAAAGAGGACACGAAGGAGCTGGTGGTGGCCAAGGCTGGAGTCTA

CTATGTCTTCTTTCAACTAGAGCTGCGGCGCGTGGTGGCCGGCGAGGGCT

CAGGCTCCGTTTCACTTGCGCTGCACCTGCAGCCACTGCGCTCTGCTGCT

GGGGCCGCCGCCCTGGCTTTGACCGTGGACCTGCCACCCGCCTCCTCCGA

GGCTCGGAACTCGGCCTTCGGTTTCCAGGGCCGCTTGCTGCACCTGAGTG

CCGGCCAGCGCCTGGGCGTCCATCTTCACACTGAGGCCAGGGCACGCCAT

GCCTGGCAGCTTACCCAGGGCGCCACAGTCTTGGGACTCTTCCGGGTGAC

CCCCGAAATCCCAGCCGGACTCCCTTCACCGAGGTCGGAATAACGCCCAG

CCTGGGTGCAGCCCACCTGGACAGAGTCCGAATCCTACTCCATCCTTCAT

GGAGACCCCTGGTGCTGGGT.

In addition, an exemplary murine 4-1BBL amino acid sequence (NCBI NP_033430.1), (mouse ortholog) is provided below:

(SEQ ID NO: 10)
MDQHTLDVEDTADARHPAGTSCPSDAALLRDTGLLADAALLSDTVRPTNA

ALPTDAAYPAVNVRDREAAWPPALNFCSRHPKLYGLVALVLLLLIAACVP

IFTRTEPRPALTITTSPNLGTRENNADQVTPVSHIGCPNTTQQGSPVFAK

LLAKNQASLCNTTLNWHSQDGAGSSYLSQGLRYEEDKKELVVDSPGLYYV

FLELKLSPTFTNTGHKVQGWVSLVLQAKPQVDDFDNLALTVELFPCSMEN

KLVDRSWSQLLLLKAGHRLSVGLRAYLHGAQDAYRDWELSYPNTTSFGLF

LVKPDNPWE.

A nucleic acid molecule encoding a full-length, murine 4-1BBL polynucleotide sequence (cDNA), NCBI Accession No. NCBI AK155610.1, is provided below:

(SEQ ID NO: 11)
gataaagcacgggcactggcgggagacgtgcactgaccgaccgtggtaat ggaccagcacacacttgatgtggaggataccgcggatgccagacatccag caggtacttcgtgcccctcggatgcggcgctcctcagagataccgggctc ctcgcggacgctgcgctcctctcagatactgtgcgcccacaaatgccgc gctccccacggatgctgcctaccctgcggttaatgttcgggatcgcgagg ccgcgtggccgcctgcactgaacttctgttcccgccacccaaagctctat ggcctagtcgctttggttttgctgcttctgatcgccgcctgtgttcctat cttcacccgcaccgagcctcggccagcgctcacaatcaccacctcgccca acctgggtacccgagagaataatgcagaccaggtcacccctgtttcccac attggctgccccaacactacacaacagggctctcctgtgttcgccaagct actggctaaaaaccaagcatcgttgtgcaatacaactctgaactggcaca gccaagatggagctgggagctcatacctatctcaaggtctgaggtacgaa gaagacaaaaaggagttggtggtagacagtcccgggctctactacgtatt tttggaactgaagctcagtccaacattcacaaacacaggccacaaggtgc agggctgggtctctcttgttttgcaagcaaagcctcaggtagatgactttt gacaacttggccctgacagtggaactgttcccttgctccatggagaacaa gttagtggaccgttcctggagtcaactgttgctcctgaaggctggccacc gcctcagtgtgggtctgagggcttatctgcatggagcccaggatgcatac agagactgggagctgtcttatcccaacaccaccagctttggactctttct tgtgaaacccgacaacccatgggaatgagaactatccttcttgtgactcc tagttgctaagtcctcaagctgctatgttttatggggtctgagcagggt cccttccatgactttctcttgtctttaactggacttggtatttattctga gcatagctcagacaagactttatataattcactagatagcattagtaaac tgctgggcagctgctagataaaaaaaaatttctaaatcaaagtttatatt tatattaatatataaaaataaatgtgtttgt.

By "OX40 ligand (OX40L)" (also called TNFL4) is meant a polypeptide having at least 85% amino acid sequence identity, or at least 90% amino acid sequence, or at least 95% amino acid sequence identity, or at least 98% amino acid sequence identity to the human amino acid sequence (Accession No. P23510), or a fragment thereof, shown below:

(SEQ ID NO: 12)
MERVQPLEENVGNAARPRFERNKLLLVASVIQGLGLLLCFTYICLHFSAL

QVSHRYPRIQSIKVQFTEYKKEKGFILTSQKEDEIMKVQNNSVIINCDGF

YLISLKGYFSQEVNISLHYQKDEEPLFQLKKVRSVNSLMVASLTYKDKVY

LNVTTDNTSLDDFHVNGGELILIHQNPGEFCVL.

By "OX40L polynucleotide" is meant a nucleic acid molecule encoding a human OX40L protein. By way of example, a full-length, human OX40L polynucleotide sequence (Accession No. NCBI: CCDS1306.1), is provided below:

(SEQ ID NO: 13)
atggaaagggtccaacccctggaagagaatgtgggaaatgcagccaggcc aagattcgagaggaacaagctattgctggtggcctctgtaattcaggac tggggctgctcctgtgcttcacctacatctgcctgcacttctctgctctt caggtatcacatcggtatcctcgaattcaaagtatcaaagtacaatttac cgaatataagaaggagaaaggtttcatcctcacttcccaaaaggaggatg aaatcatgaaggtgcagaacaactcagtcatcatcaactgtgatgggttt tatctcatctccctgaagggctacttctcccaggaagtcaacattagcct tcattaccagaaggatgaggagcccctcttccaactgaagaaggtcaggt ctgtcaactccttgatggtggcctctctgacttacaaagacaaagtctac ttgaatgtgaccactgacaatacctccctggatgacttccatgtgaatgg cggagaactgattcttatccatcaaaatcctggtgaattctgtgtcctt ga.

By "Programmed Cell Death Protein 1 (PD-1)" is meant a polypeptide having at least 85% amino acid sequence identity, or at least 90% amino acid sequence, or at least 95% amino acid sequence identity, or at least 98% amino acid sequence identity to the human amino acid sequence (NCBI Accession No. NP_005009.2), or a fragment thereof, shown below:

(SEQ ID NO: 14)
MQIPQAPWPVVWAVLQLGWRPGWFLDSPDRPWNPPTFSPALLVVTEGDNA

TFTCSFSNTSESFVLNWYRMSPSNQTDKLAAFPEDRSQPGQDCRFRVTQL

PNGRDFHMSVVRARRNDSGTYLCGAISLAPKAQIKESLRAELRVTERRAE

VPTAHPSPSPRPAGQFQTLVVGVVGGLLGSLVLLVWVLAVICSRAARGTI

GARRTGQPLKEDPSAVPVFSVDYGELDFQWREKTPEPPVPCVPEQTEYAT

IVFPSGMGTSSPARRGSADGPRSAQPLRPEDGHCSWPL.

By "PD-1" is meant a nucleic acid molecule encoding a human PD-1 protein. By way of example, a full-length, human PD-1 polynucleotide sequence (NCBI Accession No. NM_005018.2) is provided below:

(SEQ ID NO: 15)
  1 agtttccctt ccgctcacct ccgcctgagc agtggagaag
    gcggcactct ggtggggctg
 61 ctccaggcat gcagatccca caggcgccct ggccagtcgt
    ctgggcggtg ctacaactgg
121 gctggcggcc aggatggttc ttagactccc cagacaggcc
    ctggaacccc ccaccttct
181 ccccagccct gctcgtggtg accgaagggg acaacgccac
    cttcacctgc agcttctcca
241 acacatcgga gagcttcgtg ctaaactggt accgcatgag
    ccccagcaac cagacggaca
301 agctggccgc cttccccgag gaccgcagcc agcccggcca
    ggactgccgc ttccgtgtca
361 cacaactgcc caacgggcgt gacttccaca tgagcgtggt
    cagggcccgg cgcaatgaca
421 gcggcaccta cctctgtggg gccatctccc tggccccaa
    ggcgcagatc aaagagagcc
481 tgcgggcaga gctcagggtg acagagagaa gggcagaagt
    gcccacagcc cacccccagcc
541 cctcacccag gccagccggc cagttccaaa ccctggtggt
    tggtgtcgtg ggcggcctgc
601 tgggcagcct ggtgctgcta gtctgggtcc tggccgtcat
    ctgctcccgg gccgcacgag
661 ggacaatagg agccaggcgc accggccagc ccctgaagga
    ggaccccctca gccgtgcctg
721 tgttctctgt ggactatggg gagctggatt tccagtggcg
    agagaagacc ccggagcccc
781 ccgtgccctg tgtccctgag cagacggagt atgccaccat
    tgtctttcct agcggaatgg
841 gcacctcatc ccccgcccgc aggggctcag ctgacggccc
    tcggagtgcc cagccactga
901 ggcctgagga tggacactgc tcttggcccc tctgaccggc
    ttccttggcc accagtgttc

```
-continued
 961 tgcagaccct ccaccatgag cccgggtcag cgcatttcct
     caggagaagc aggcagggtg
1021 caggccattg caggccgtcc aggggctgag ctgcctgggg
     gcgaccgggg ctccagcctg
1081 cacctgcacc aggcacagcc ccaccacagg actcatgtct
     caatgcccac agtgagccca
1141 ggcagcaggt gtcaccgtcc cctacaggga gggccagatg
     cagtcactgc ttcaggtcct
1201 gccagcacag agctgcctgc gtccagctcc ctgaatctct
     gctgctgctg ctgctgctgc
1261 tgctgctgcc tgcggccgg ggctgaaggc gccgtggccc
     tgcctgacgc cccggagcct
1321 cctgcctgaa cttgggggct ggttggagat ggccttggag
     cagccaaggt gccctggca
1381 gtggcatccc gaaacgccct ggacgcaggg cccaagactg
     ggcacaggag tgggaggtac
1441 atggggctgg ggactcccca ggagttatct gctccctgca
     ggcctagaga agtttcaggg
1501 aaggtcagaa gagctcctgg ctgtggtggg cagggcagga
     aaccctcca cctttacaca
1561 tgcccaggca gcacctcagg ccctttgtgg ggcagggaag
     ctgaggcagt aagcgggcag
1621 gcagagctgg aggcctttca ggcccagcca gcactctggc
     ctcctgccgc cgcattccac
1681 cccagcccct cacaccactc gggagaggga catcctacgg
     tcccaaggtc aggagggcag
1741 ggctggggtt gactcaggcc cctcccagct gtggccacct
     gggtgttggg agggcagaag
1801 tgcaggcacc tagggccccc catgtgccca ccctgggagc
     tctccttgga acccattcct
1861 gaaattattt aaaggggttg gccgggctcc caccagggcc
     tgggtgggaa ggtacaggcg
1921 ttccccgggg gcctagtacc cccgccgtgg cctatccact
     cctcacatcc acacactgca
1981 cccccactcc tggggcaggg ccaccagcat ccaggcggcc
     agcaggcacc tgagtggctg
2041 ggacaaggga tccccttcc ctgtggttct attatattat
     aattataatt aaatatgaga
2101 gcatgctaag gaaaa
```

The term "cognate ligand" refers to the specific binding partner, binding member, or ligand with which a checkpoint protein specifically interacts or with which it specifically binds. For example, a specific ligand to which a receptor protein binds or with which it interacts is a "cognate ligand" for that receptor protein. Similarly, the receptor protein is a cognate ligand for a specific ligand molecule or protein.

By "checkpoint inhibitor" is meant an agent that enhances an anti-cancer immune response by blocking, reducing or disrupting the activity of a checkpoint protein. Examples of checkpoint proteins found on T cells or cancer cells include PD-1/PD-L1 and CTLA-4/B7-1/B7-2. Exemplary checkpoint inhibitors include agents (e.g., antibodies) that bind to such proteins. Checkpoint protein inhibitors (also called "immune checkpoint protein inhibitors") are typically proteins or small molecules, e.g., druggable proteins or small molecules, that block or interrupt the interaction of certain proteins expressed by some types of immune cells in the body (e.g., T cells) with cognate proteins expressed by some cancer cells. In a particular embodiment, checkpoint protein inhibitors include antibodies and fragments of the antibodies that retain binding to checkpoint protein molecules, which prevent certain checkpoint proteins expressed on cells, particularly immune cells (e.g. T cells), from becoming inactive or anergic such that they do not attack and kill foreign or "non-self" cells in the body. Such inactivation of T-cells can occur when tumor cells that express ligands, such as PD-L1, bind to the cognate checkpoint proteins on T cells, e.g., PD-1. In embodiments, a checkpoint protein inhibitor is an antibody, such as a monoclonal antibody, a humanized antibody, a human antibody, a single chain antibody, etc., or a fragment thereof that binds to a checkpoint protein (cognate ligand). As noted above, checkpoint protein inhibitors target certain immune checkpoint proteins. Without limitation, PD-1, programmed cell-death protein 1, is a checkpoint protein targeted by checkpoint inhibitors (for example, nivoumab (Optivo, Bristol-Myers Squibb); pembrolizumab (Keytruda, Merck & Co.); Pidilizumab (CT-011, CureTech); MEDI0680 (AMP-514)); PD-L1, programmed cell-death ligand 1, is a checkpoint protein targeted by checkpoint inhibitors, (for example, MEDI4736 (AstraZeneca); MPDL3280A, Roche/Genentech; Tecentriq, Genentech); MSB-0010718C (Merck KGaA)). Other checkpoint proteins and their targeting checkpoint inhibitors include CTLA-4 (cytotoxic T-lymphocyte protein 4, also called CD152) checkpoint inhibitors, (for example, Tremelimumab (AstraZeneca); LAG-3, lymphocyte activation gene 3 protein, checkpoint inhibitors (for example, BNS-986016, Bristol-Myers Squibb); KIR, killer cell immunoglobulin-like receptor, checkpoint inhibitors, (for example, Lirilumab (BMS-986015), Bristol-Myers Squibb); IDO1, indoleamine 2,3-dioxygenase 1, checkpoint inhibitors (for example, Indoximod (NLG-9189, NewLink Genetics); NLG-919 (NewLink Genetics); INCB024360 (Incyte)); 4-1BB, a tumor necrosis factor receptor superfamily member 9 (TN-FRS9), (also known as CD137) checkpoint inhibitors, (for example, PF-05082566 (Pfizer); Urelumab (BMS-663513), Bristol-Myers Squibb); TIM-3, "T-cell immunoglobulin domain and mucin domain," checkpoint inhibitors; OX40, tumor necrosis factor receptor superfamily member 4, (also known as CD134) checkpoint inhibitors, (for example, MEDI6469 (AztraZeneca)); A2aR, adenosine A2A receptor, checkpoint inhibitors, B7-H3 (also called CD276) checkpoint inhibitors, B7-H4 (also called VTCN1) checkpoint inhibitors, B7-1/B7-2 checkpoint inhibitors, BTLA (also called CD272) checkpoint inhibitors, VISTA, "V-domain Ig suppressor of T cell activation," checkpoint inhibitors, and the like.

"Costimulatory molecules" are proteins on the surfaces of lymphocytes (B cells and T cells) whose engagement by specific ligand is considered necessary for a complete activation response following antigen binding to an antigen receptor. Signaling through costimulatory molecules can affect antigen receptor signaling in very important ways. Costimulatory molecules play a critical role in augmenting the interaction between antigen presenting cells and CD4+ T-lymphocytes. The interaction between B7 and CD28 may determine whether a Th2 type cell response develops, and studies have shown that B7-2 (CD86) skews toward a Th2 response. Costimulatory molecules play a central role during the initiation of T-cell immune responses. CD28 and CTLA-4 represent the costimulatory receptors on T cells, and B7 molecules represent their corresponding ligands on APCs. Several studies carried out in murine models demonstrated that the signal mediated via CD28 is required for TCR-mediated T-cell activation, while CTLA-4 has an antagonistic role in T-cell activation. The cognate ligands for CD28 and CTLA-4 expressed on APCs are B7-1 (CD80) and B7-2 (CD86) of the B7 family. These two molecules show comparable affinity to CD28 molecules and differentially activate Th1 or Th2 immune responses. Costimulatory molecules may also be immune checkpoint proteins.

Costimulatory molecules (i.e., cognate binding molecules, e.g., receptor ligand) CD80/CD28, tumor necrosis factor (TNF)/TNFR, and T-cell immunoglobulin mucin (TIM) superfamilies have revealed the variety of possible ligand-receptor interactions that has elaborated the understanding of regulatory mechanisms of the immune responses mediated by APCs and T cells. For example, a positive regulator like CD40L (on T cells) when interacting or associated with CD40 (on APCs), not only activates T cells but also results in the activation of dendritic cells (DCs); a process that is popularly called "T-cell licensing." Similarly, the ligation of CD28 with cognate ligands CD80 and CD86 is known to induce the secretion of interleukin-6 (IL-6) and interferon-γ (IFN-γ) by DCs, as well as the activation, proliferation, and differentiation of B cells. In addition, 4-1BBL expressed on DCs, binds to 4-1 BB on T cells, to bolster the activity of DCs in helping T cells. Many studies have reported the inhibitory roles of cytotoxic T lymphocyte-associated antigen (CTLA-4; CD152) and programmed death (PD)-1 (expressed on T cells) with ligands CD80/CD86 and PDL-1/PDL-2 (on APCs), respectively. These studies clearly suggest that costimulation not only amplifies the magnitude of the activation of T cells and APCs, but also finetunes the immune response as well, thereby controlling hyper activation of the immune response. T-cell interaction with APC involving TCR and costimulatory molecules activates several downstream signaling molecules, leading, for example, to the induction of the expression of CD40L, PD-1, and CD28.

A lack of costimulation can lead to T-cell anergy. Peptide epitopes presented by APCs expressing MHC Class I molecules (non-professional APCs) may fail to activate T cells if a first signal (antigen presentation) is delivered in the absence of a second signal (costimulation), and instead may lead to anergy of the T cells. Because of the role played by costimulatory molecules in the initiation of T-cell responses, they can be manipulated to either stimulate the immune system to treat (or prevent) cancers, tumors, or infection, or to inhibit the immune system for immunotherapy, e.g., against allergies and autoimmune diseases.

"Detect" refers to identifying the presence, absence or amount of a molecule, compound, or agent to be detected.

By "detectable label" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

By "disease" is meant any condition or disorder that adversely affects, damages or interferes with the normal function of a cell, tissue, organ, or part of the body, such as cancer or tumorigenesis.

By "effective amount" is meant the amount of a required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount. In one embodiment, an effective amount is the amount of an agent of the invention required to reduce or stabilize the rate of proliferation of a cancer cell. In another embodiment, an effective amount is the amount of an agent of the invention required to reduce the survival of a cancer cell. In another embodiment, an effective amount is the amount of an agent of the invention required to induce the death of a cancer cell.

As used herein, the term "endogenous" describes a molecule (e.g., a polypeptide, peptide, nucleic acid, or cofactor) that is found naturally in a particular organism (e.g., a human) or in a particular location within an organism (e.g., an organ, a tissue, or a cell, such as a human cell).

As used herein, the term "epitope" or "antigenic determinant" refers to a site, e.g., an amino acid sequence, on an antigen (e.g., a tumor-associated antigen) to which a ligand, an antibody, or T-cell receptor is capable of binding (e.g., during the induction of an immune response) that can be formed from either contiguous amino acids or discontinuous amino acids that are rendered spatially proximal by the tertiary folding of a protein. Other epitopes are formed by quaternary structures, e.g., by the assembly of several polypeptides. Epitopes formed from contiguous amino acids are typically retained on exposure to denaturing solvents, while epitopes formed by tertiary or quaternary folding are typically lost on treatment with denaturing solvents. An epitope may include, e.g., from 3-30 amino acid residues, or from 5 to 30 or from 5 to 25 amino acid residues, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid residues, which may be in a distinct spatial conformation. Methods of determining spatial conformation of epitopes are known in the art and include, e.g., x-ray crystallography and 2-dimensional nuclear magnetic resonance (NMR). Such methods are described in detail, e.g., in Morris, *Epitope Mapping Protocols in Methods in Molecular Biology*, Vol. 66, (1996).

The term "epitope spreading" (also called "antigen spreading") refers to the diversification of epitope specificity from an initial focused, epitope-specific immune response (e.g., by cytotoxic T cells) directed against a self or foreign antigen or protein, to subdominant and/or cryptic, or mutated epitopes on the protein (intramolecular spreading) or on other proteins (intermolecular spreading). Epitope spreading may enable a patient's immune system to mount an immune response against additional epitopes not initially recognized by cells (e.g., cytotoxic T cells) of the immune system while reducing the possibility of escape variants in the tumor population, and may thus attenuate progression of disease (cancer). In one embodiment, after vaccination with a vector described herein, T cells are generated that respond to tumor associated antigens that were not in the original vaccine formulation, indicating that a secondary round of T cell priming has occurred with antigens derived from tumor cells.

As used herein, the term "exogenous" refers to a molecule (e.g., a polypeptide, peptide nucleic acid, or cofactor) that is not found naturally or endogenously in a particular organism (e.g., a human) or in a particular location within an organism (e.g., an organ, a tissue, or a cell, such as a human cell). Exogenous materials include those that are provided from an external source to an organism or to cultured matter extracted therefrom.

By "fragment" or "portion" is meant a portion of a polypeptide or nucleic acid molecule. This portion contains at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

As used herein, the term "immune response" refers to a subject's immune system response or reaction to one or more antigens, (e.g., an immunogenic protein or peptide), and/or the epitopes of the antigens, recognized by the immune system as foreign or heterologous. Immune responses include both cell-mediated immune responses (i.e., responses mediated by effector T cells, such as antigen-specific or non-specific T-cells, such as CD8+ T-cells, Th1 cells, Th2 cells, and Th17 cells) as well as humoral immune responses (i.e., responses characterized by B-cell activation and the production of antigen-specific antibodies). The term "immune response" encompasses both the innate immune responses to an antigen or immunogen (e.g., a tumor-associated antigen and/or its associated epitopes) as well as memory responses that are a result of acquired immunity and can involve either B cells or T cells, or both.

The terms "isolated," "purified," or "biologically pure" refer to material that is free to varying degrees from components which normally accompany or are associated with it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid, protein, or peptide gives rise to essentially one band in an electrophoretic gel. For a protein that can be subjected to modifications, for example, phosphorylation or glycosylation, different modifications may give rise to different isolated proteins, which can be separately purified.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide that has been separated from components that naturally accompany it. Typically, a polypeptide is isolated when it is at least 60%, by weight, free from the proteins and naturally-occurring organic molecules with which it is naturally associated. Preferably, the preparation is at least 75%, or at least 85%, or at least 90%, or at least 99%, by weight, a desired polypeptide. An isolated polypeptide may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "marker" is meant any protein or polynucleotide having an alteration in expression level or activity that is associated with a disease or disorder.

A "neo-epitope" as referred to herein is a newly formed (or neo) epitope (e.g., antigenic determinant) that has not been previously recognized by the immune system. Neo-epitopes encompass epitopes on a neoantigen, which is a newly formed antigen, Neoantigens, which are often associated with tumor antigens, are found in oncogenic cells. Within the described viral vectors, large quantities of proteins with the mutated neo-epitope can be generated and secreted into the cytoplasm of antigen-presenting cells of the immune system, where they are processed and used to activate tumor-specific T cells, which can then target the cancer cells and destroy them.

As used herein, "obtaining" as in "obtaining an agent" includes synthesizing, purchasing, or otherwise acquiring the agent.

By "polynucleotide" is meant a nucleic acid molecule, e.g., a double-stranded (ds) DNA polynucleotide, a single-stranded (ss) DNA polynucleotide, a dsRNA polynucleotide, or a ssRNA polynucleotide, that encodes one or more polypeptides. The term encompasses positive-sense (i.e., protein-coding) DNA polynucleotides, which are capable of being transcribed to form an RNA transcript, which can be subsequently translated to produce a polypeptide following one or more optional RNA processing events (e.g., intron excision by RNA splicing, or ligation of a 5' cap or a 3' polyadenyl tail). The term additionally encompasses positive-sense RNA polynucleotides, capable of being directly translated to produce a polypeptide following one or more optional RNA processing events. As used herein, a polynucleotide may be contained within a viral vector, such as a Sindbis viral vector.

A "minigene" when used herein refers to a molecularly engineered polynucleotide, e.g., a multigene construct containing sequences encoding different components. In an embodiment, the polynucleotide is designed to encode at least one epitope of an antigen, such as a tumor associated antigen (TAA). A minigene polynucleotide may further comprise nucleic acid sequences in addition to TAA or TAA epitope-encoding sequences, including, without limitation, framework or motif sequences (e.g., one or more enzyme cleavage sites) and processing sequences, such as a ribosome binding site, a signal sequence (e.g., an endoplasmic reticulum signal sequence), a 5' flanking region and a 3' stop codon sequence. The polynucleotide may also contain nucleic acid sequences that encode other antigens, e.g., cell receptors, or immunostimulatory or immunomodulatory molecules, such as cytokines, chemokines, cell signaling molecules, and the like. Some or all of the foregoing sequences may be included in the polynucleotide. A minigene may be a polynucleotide, such as a negative-sense DNA or RNA polynucleotide, which serves as a template for the production of a positive-sense polynucleotide.

As used herein, the phrase "pharmaceutically acceptable" refers to molecular entities, biological products and compositions that are physiologically tolerable and do not typically produce an allergic reactopm or other adverse reaction, such as gastric upset, dizziness and the like, when administered to a patient (e.g., a human patient).

As used herein, the terms "prevent," "preventing," "prevention," "prophylactic treatment" and the like refer to reducing the probability of developing a disorder or condition in a subject, who does not have, but who is at risk of or susceptible to developing a disorder or condition.

As used herein, the term "pseudotyped" refers to a viral vector that contains one or more foreign viral structural proteins, e.g., envelope glycoproteins. A pseudotyped virus may be one in which the envelope glycoproteins of an enveloped virus or the capsid proteins of a non-enveloped virus originate from a virus that differs from the source of the original virus genome and the genome replication apparatus. (D. A. Sanders, 2002, *Curr. Opin. Biotechnol.,* 13:437-442). The foreign viral envelope proteins of a pseudotyped virus can be utilized to alter host tropism or to increase or decrease the stability of the virus particles. Examples of pseudotyped viral vectors include a retrovirus or lentivirus that contains one or more envelope glycoproteins that do not naturally occur on the exterior of the wild-type retrovirus or lentivirus, such as one or more proteins derived from an *Alphavirus* (e.g., Sindbis virus, such as Sindbis-ZZ E2 protein (Morizono, K. et al., 2010, *J. Virol.,* 84 (14):6923-6934), or Sindbis E1, E2 and/or E3 proteins). Pseudotyped viral vectors can infect cells and express and produce proteins encoded by polynucleotides, e.g., "minigenes", contained within the viral vectors.

By "reduces" is meant a negative alteration of at least 5%, 10%, 25%, 50%, 75%, or 100%.

By "reference" is meant a standard or control condition. In one embodiment, a standard of comparison is an untreated control cell (e.g., cancer cell) or an untreated subject having cancer.

By "specifically binds" is meant a compound or antibody that recognizes and binds a polypeptide of the invention, but which does not substantially recognize and bind other molecules in a sample, for example, a biological sample, which naturally includes a polypeptide of the invention.

By "subject" is meant a mammal, including, but not limited to, a human or non-human mammal, such as a non-human primate, bovine, equine, canine, ovine, or feline mammal. A subject is typically a patient, such as a human patient, who receives treatment for a particular disease or condition as described herein (e.g., a cell proliferation disease, such as cancer or tumor). Examples of subjects and patients include mammals, such as humans, receiving treatment for such diseases or conditions or who are at risk of having such diseases or conditions.

As used herein, the term "suicide gene" refers to a gene encoding a polypeptide capable of inducing cell death, e.g., by apoptosis. Suicide genes may function by encoding a protein or peptide capable of converting a prodrug into a cytotoxic molecule. Exemplary suicide genes include, without limitation, Herpes simplex virus thymidine kinase (HSV-TK), cytosine deaminase, nitroreductase, carboxylesterase, cytochrome P450, and purine nucleoside phosphorylase (PNP), among others.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the term "therapeutically effective amount" refers to a quantity of a therapeutic agent that is sufficient to treat, diagnose, prevent, and/or delay the onset of one or more symptoms of a disease, disorder, and/or condition upon administration to a patient in need of treatment. In some cases, a therapeutically effective amount may also refer to a quantity of a therapeutic agent that is administered prophylactically (e.g., in advance of the development of full-blown disease) to a subject who is at risk of developing a disease or the symptoms thereof, such as cancer or a tumor.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated. "Treat" or "treatment" may refer to therapeutic treatment, in which the object is to prevent or slow down (lessen or reduce) an undesired physiological change or disorder, such as the progression of a cell proliferation disorder, such as cancer. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. Those in need of treatment include those already with the condition or disorder, as well as those prone to have the condition or disorder or those in whom the condition or disorder is to be prevented.

As used herein, the term "tumor-associated antigen" or "TAA" refers to a protein, polypeptide, or peptide that is expressed by cancer cell, such as a cell within a solid tumor. Tumor-associated antigens include protein or peptide antigens that are expressed on the surface of a cancer cell or that are overexpressed relative to a non-cancerous cell, as well as proteins that arise from mutations of wild-type proteins. Proteins that arise from mutations of wild-type cellular proteins embrace neo-epitopes and neo-antigens that occur in cancer or tumor cells, e.g., mutated k-Ras proteins. Tumor associated antigens thus embrace cell surface receptor proteins, e.g., membrane bound proteins, that are expressed on the surface of a cancer or tumor cell. Tumor associated antigens also embrace intracellular, e.g., cytoplasmic, nuclear, or membrane-bound proteins that are expressed within a cancer or tumor cell. A tumor-associated antigen may be tumor-specific, in which case the expression of the antigen is restricted to a particular type of cancer cell. Alternatively, a tumor-associated antigen may be common to several cancers and thus expressed on the surface of a variety of cancer cell types.

As used herein, the term "vector" refers to a nucleic acid (e.g., a DNA vector, such as a plasmid), a RNA vector, virus or other suitable replicon (e.g., viral vector). A variety of vectors have been developed for the delivery of polynucleotides encoding exogenous proteins into a prokaryotic or eukaryotic cell. A vector may contain a polynucleotide sequence that includes gene of interest (e.g., a gene encoding a tumor-associated antigen and/or an epitope thereof) as well as, for example, additional sequence elements capable of regulating transcription, translation, and/or the integration of these polynucleotide sequences into the genome of a cell. A vector may contain regulatory sequences, such as a promoter, e.g., a subgenomic promoter, region and an enhancer region, which direct gene transcription. A vector may contain polynucleotide sequences that enhance the rate of translation of these genes or improve the stability or nuclear export of the mRNA that results from gene transcription. These sequence elements may include, e.g., 5' and 3' untranslated regions, an internal ribosomal entry site (IRES), and/or a polyadenylation signal site in order to direct efficient transcription of a gene carried on the expression vector.

As used herein, the term "vehicle" refers to a solvent, diluent, or carrier component of a pharmaceutical composition.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, preferably at least 70%, more preferably 80% or 85%, and most preferably 90%, 95% or even 99% identical at the amino acid level or nucleic acid to the sequence used for comparison, for example, over a specified comparison window. Optimal alignment may be conducted using the homology alignment algorithm of Needleman and Wunsch, 1970, *J. Mol. Biol.*, 48:443. An indication that two peptide or polypeptide sequences are substantially identical is that one peptide or polypeptide is immunologically reactive with specific antibodies raised against the second peptide or polypeptide, although such cross-reactivity is not required for two polypeptides to be deemed substantially identical. Thus, a peptide or polypeptide is substantially identical to a second peptide or polypeptide, for example, where the two differ only by a conservative substitution. Peptides or polypeptides that are "substantially similar" share sequences as noted above except that residue positions which are not identical may differ by conservative amino acid changes. Conservative substitutions typically include, but are not limited to, substitutions within the following groups: glycine and alanine; valine, isoleucine, and leucine; aspartic acid and glutamic acid; asparagine and glutamine; serine and threonine; lysine and arginine; and phenylalanine and tyrosine, and others as known to the skilled person in the art.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

Polynucleotides and viral nucleic acid molecules useful in the methods of the invention include any nucleic acid molecule that encodes the components of viral vectors described herein and the polypeptide products encoded by the viral vectors, such as *Alphavirus* vectors, Sindbis viral vectors and the like, as well as peptides or fragments thereof. Such nucleic acid molecules need not be 100% identical with the viral vector nucleic acid sequence, but will typically exhibit substantial identity. Polynucleotides having substantial identity to the viral vector sequences are typically capable of hybridizing with at least one strand of the viral vector nucleic acid molecule. Nucleic acid molecules useful in the methods of the invention include any nucleic acid molecule that encodes a polypeptide of the invention or a fragment thereof. Polynucleotides having "substantial identity" to an endogenous sequence are typically capable of hybridizing with at least one strand of a double-stranded nucleic acid molecule. By "hybridize" is meant the pair of nucleic acid molecules to form a double-stranded molecule between complementary polynucleotide sequences (e.g., a gene or nucleic acid sequence described herein), or portions thereof, under various conditions of stringency. (See, e.g., Wahl, G. M. and S. L. Berger (1987) Methods Enzymol. 152:399; Kimmel, A. R. (1987) Methods Enzymol. 152: 507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1%

SDS. In a more preferred embodiment, wash steps will occur at 42 C in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

Nucleic acids that do not hybridize to each other under stringent conditions are still substantially identical if the polypeptides that they encode are substantially identical. This occurs, for example, when a copy of a nucleic acid is created using the maximum codon degeneracy permitted by the genetic code. In such cases, the nucleic acids typically hybridize under moderately stringent hybridization conditions. Nonlimiting examples of "moderately stringent hybridization conditions" include a hybridization in a buffer of 40% formamide, 1 M NaCl, 1% SDS at 37 C, and a wash in 1×SSC at 45 C. A positive hybridization is at least twice background. Those of ordinary skill will readily recognize that alternative hybridization and wash conditions can be utilized to provide conditions of similar stringency.

By "ortholog" is meant any polypeptide or nucleic acid molecule of an organism that is highly related to a reference protein or nucleic acid sequence from another organism. The degree of relatedness may be expressed as the probability that a reference protein would identify a sequence, for example, in a blast search. The probability that a reference sequence would identify a random sequence as an ortholog is extremely low, less than $e^{-10}$, $e^{-20}$, $e^{-30}$, $e^{-40}$, $e^{-50}$, $e^{-75}$, $e^{-100}$. The skilled artisan understands that an ortholog is likely to be functionally related to the reference protein or nucleic acid sequence. In other words, the ortholog and its reference molecule would be expected to fulfill similar, if not equivalent, functional roles in their respective organisms, e.g., mouse and human orthologs.

It is not required that an ortholog, when aligned with a reference sequence, have a particular degree of amino acid sequence identity to the reference sequence. A protein ortholog might share significant amino acid sequence identity over the entire length of the protein, for example, or, alternatively, might share significant amino acid sequence identity over only a single functionally important domain of the protein. Such functionally important domains may be defined by genetic mutations or by structure-function assays. Orthologs may be identified using methods practiced in the art. The functional role of an ortholog may be assayed using methods well known to the skilled artisan. For example, function might be assayed in vivo or in vitro using a biochemical, immunological, or enzymatic assay; or transformation rescue. Alternatively, bioassays may be carried out in tissue culture; function may also be assayed by gene inactivation (e.g., by RNAi, siRNA, or gene knockout), or gene over-expression, as well as by other methods.

Unless specifically stated or obvious from context, as used herein, the term "or" is understood to be inclusive. Unless specifically stated or obvious from context, as used herein, the terms "a", "an", and "the" are understood to be singular or plural.

As used herein, the term "about" or "approximately" means within an acceptable error range for the type of value described and the method used to measure the value. For example, these terms can signify within 20%, more preferably within 10%, and most preferably still within 5% of a given value or range. More specifically, "about" can be understood as within 20%, 10%, 9%, 8%, 7%, 6%, 5%, 4%, 3%, 2%, 1%, 0.5%, 0.1%, 0.05%, or 0.01% of the stated value or range. Alternatively, especially in biological systems, the term "about" means within one log unit (i.e., one order of magnitude), preferably within a factor of two of a given value. Unless specifically stated or obvious from context, as used herein, the term "about" is understood as within a range of normal tolerance in the art, for example within 2 standard deviations of the mean. Unless otherwise clear from context, all numerical values provided herein are modified by the term about.

Any compositions or methods provided herein can be combined with one or more of any of the other compositions, or components thereof, and methods provided herein.

BRIEF DESCRIPTION OF THE DRAWINGS

FIGS. 1A and 1B present polynucleotide sequences and amino acid sequences related to the PD-1 checkpoint protein. FIG. 1A presents the polynucleotide sequence (top, SEQ ID NO: 16) and the encoded amino acid (aa) sequence (bottom, SEQ ID NO: 17) of PD-1 (Programmed cell death protein 1) precursor [Homo sapiens]. The PD-1 polynucleotide sequence was cloned into the T7StuI-R vector (Accession No. NP_005009 VERSION NP_005009.2). The elements delineated in the sequences and depicted from the 5' end of the sequences are as follows: The soluble PD-1 amino acid (aa) sequence (1-169 aa) is shown in gray; the hingeregion is shown by double underlining; the Linker sequence is shown in Italics; and the Ig CH3 domain is shown by single underlining. The CH3 and hinge domains are from human IgG1 (Accession No.: P01857.1). The Linker is synthetically produced. FIG. 1B shows an amino acid sequence comparison (alignment) of the human WT-PD-1 amino acid sequence (SEQ ID NO: 18) to PD-1 amino acid sequences of other species, namely, mouse (SEQ ID NO: 19) and monkey (SEQ ID NO: 20).

In FIG. 9A, four animal treatment groups are shown: (1) control untreated animals; (2) animals treated with a Sindbis virus (SV) vector encoding the tumor-associated antigen (TAA) NY-ESO-1. The designation of this SV vector is SV-NYESO1; (3) animals treated with an anti-OX40L antibody (commercially available from Bio-X-Cell, West Lebanon, NH; InVivoMAb anti-mouse OX40L (CD134L), Clone RM134L, Catalog #BE0033-1); and (4) animals treated with a combination of SV-NYESO1 and the anti-OX40L antibody. In FIG. 9B, four groups of treated animals are shown: (1) control untreated animals; (2) animals treated with SV-NYESO1; (3) animals treated with a Sindbis virus (SV) vector encoding OX40L. The designation of this SV vector is SV-OX40L; and (4) animals treated with a combination of SV-OX40L and SV-NYESO1. Comparing FIG. 9B with FIG. 9A, it can be seen that treatment with SV-OX40L is more efficacious than treatment with anti-OX40L antibody in promoting survival of the treated animals and that the combination of SV-NYESO-1 and SV-OX40L confers 100% survival of the treated animals, which is superior to the combination treatment of SV-NYESO1 and anti-OX40L antibody. The results suggest that "armed" Sindbis virus vectors (e.g., Sindbis virus vectors encoding a checkpoint inhibitor protein or a TAA as described herein) can provide tumor treatment that is superior to antibody-mediated therapy.

DETAILED DESCRIPTION OF THE INVENTION

Figure 2:
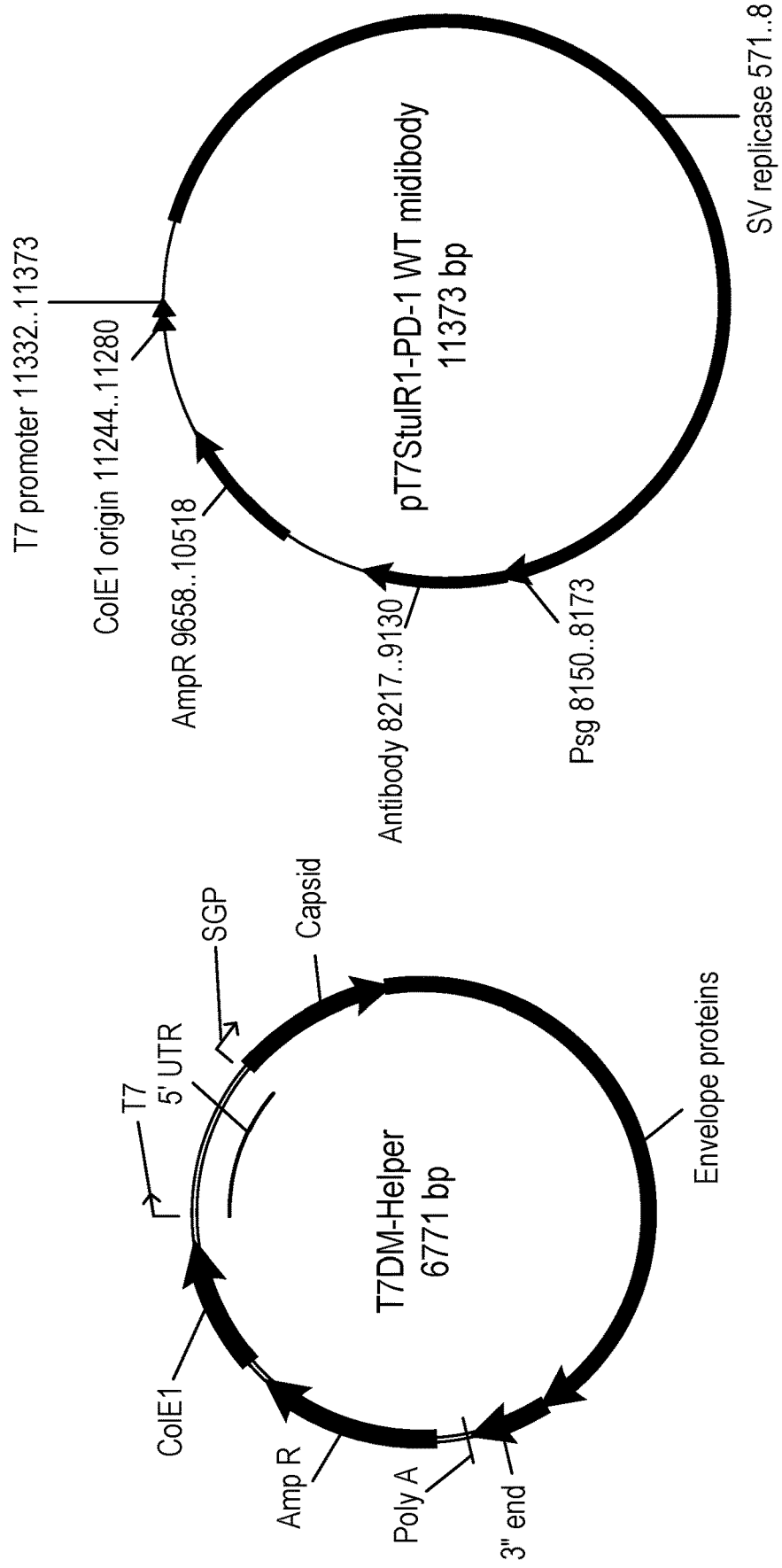
FIG. 2 presents Helper and Replicon DNA plasmids used to make the SV-PD-1WT vector for in vivo experiments as described herein.

Provided by the present invention are polynucleotides and viral vectors, particularly, *Alphavirus* vectors, that encode an immune checkpoint protein, a costimulatory molecule, or a portion thereof that binds to the cognate ligand of the checkpoint protein or to the cognate ligand of the costimulatory molecule, which induce a potent immune response in a subject against the subject's cancer or tumor. An immune checkpoint molecule may also be referred to herein as a costimulatory molecule.

The present invention provides a polynucleotide that encodes an *Alphavirus*, lentivirus, or retrovirus protein or a fragment thereof, and an immune checkpoint molecule, or a cognate ligand binding portion or fragment thereof. In embodiments, the immune checkpoint molecule is, without limitation, PD-1, PD-L1, OX40, 4-1BB, OX40 ligand (OX40L), 4-1BB ligand (4-1BBL), or CTLA-4. In a particular embodiment, the immune checkpoint protein molecule is PD-1 or the extracellular domain of PD-1. In other particular embodiments, the immune checkpoint protein molecule is OX40L or 4-1BBL, or the extracellular domains thereof.

In an embodiment of the foregoing aspects, the polynucleotide encodes an *Alphavirus* (e.g., Sindbis virus protein or a fragment thereof) and an immune checkpoint molecule or a cognate ligand binding portion or fragment thereof. In an embodiment, the *Alphavirus* is Sindbis virus, a Sindbis virus vector, or Sindbis viral particle. In particular embodiments, the Sindbis virus vector contains a polynucleotide that encodes one or more immune checkpoint proteins, or a fragment or portion of the immune checkpoint protein that binds to its cognate ligand, for example and without limitation, the PD-1 immune checkpoint protein or a fragment or portion of PD-1 that binds to its cognate ligand PD-L1; the OX40L or a fragment or portion of OX40L that binds to its cognate receptor; or the 4-1BBL or a fragment or portion of 4-1BBL that binds to its cognate receptor. In a particular embodiment, the Sindbis virus vector contains a polynucleotide that encodes the PD-1 immune checkpoint protein, or an extracellular domain of PD-1, that binds to its cognate ligand PD-L1. In a particular embodiment, the Sindbis virus vector contains a polynucleotide that encodes the OX40L immune checkpoint protein, or an extracellular domain of OX40L, that binds to its cognate receptor. In a particular embodiment, the Sindbis virus vector contains a polynucleotide that encodes the 4-1BBL immune checkpoint protein, or an extracellular domain of 4-1BBL, that binds to its cognate receptor. In an embodiment, the checkpoint protein is a soluble form of the protein.

In an embodiment, the checkpoint protein encoded by the Sindbis virus vector is in the form of a "minibody," as described herein, in which checkpoint protein or a portion of the checkpoint protein, e.g., the extracellular domain, is fused to portions of an immunoglobulin (Ig) molecule, thereby forming a fusion protein. In particular, checkpoint protein or a ligand binding portion of the checkpoint protein, e.g., the extracellular domain, is fused to an Ig hinge region, and an Ig heavy chain constant region domain, such as the CH1, CH2, or CH3 domain of an Ig heavy chain. In an embodiment, a spacer (or linker) sequence is inserted between the hinge region and the Ig heavy chain CH domain for flexibility. In an embodiment, the spacer (or linker) sequence is glycine-rich and is or comprises the amino acid sequence GGGSSGGGSGG (SEQ ID NO: 1) or the amino acid sequence GGGSSGGGSGS (SEQ ID NO: 2). In embodiments, the Ig is of the IgG (e.g., IgG1, IgG2a, IgG2b, IgG4 subtypes), IgM, IgA, IgD, or IgE type. In a specific embodiment, the Ig chain is the IgG1 heavy chain and the Ig constant region domain is the CH3 domain. In an embodiment, a glycine-rich spacer (or linker) sequence is inserted between the hinge region and the Ig heavy chain CH domain for flexibility. In an embodiment, the spacer (or linker) sequence is or comprises the sequence GGGSSGGGSGG (SEQ ID NO: 1).

In embodiments of the foregoing, the checkpoint protein is, without limitation, PD-1, PD-L1, OX40, OX40L, CTLA-4, 4-1BB, 4-1BBL, KIR, LAG-3, IDO1, TIM-3, A2AR, B7-H3, B7-H4, B7-1/B7-2, BTLA and VISTA, a cognate ligand binding portion thereof, or extracellular domain thereof. As will be appreciated by the skilled practitioner in the art, the following table categorizes checkpoint molecules (i.e., costimulatory molecules or receptors) as either activating molecules or receptors, which, upon being targeted and bound by agonistic antibodies, may enhance T cell stimulation to promote an immune response such as tumor destruction, or as blocking inhibitory molecules or receptors, which, upon being targeted and bound by blocking or inhibitory antibodies, may enhance T cell stimulation to promote an immune response such as tumor destruction. The molecules presented in the below table are illustrative and are not intended to be limiting.

Representative Checkpoint Molecules/Costimulatory Molecules/Receptors that may be Targeted and Bound by Antibodies

| Activating molecule/costimulatory molecule/receptor | Inhibitory molecule/costimulatory molecule/receptor |
| --- | --- |
| CD28 | CTLA-4 |
| OX40 | PD-1 |
| GITR | TIM-3 |
| CD137 | BTLA |
| CD37 | VISTA |
| HVEM | LAG-3 |

(adapted from I. Mellman et al., 2011, *Nature*, 480(7378):480-489, which is incorporated herein by reference)

In a specific embodiment, the immune checkpoint proteins include PD-1, PD-L1, OX40, OX40L, 4-1BB, 4-1BBL, and CTLA-4. In an embodiment of the foregoing, the checkpoint protein is the extracellular domain of the protein. In a particular embodiment of the foregoing, the checkpoint protein is PD-1 or the extracellular domain of PD-1. In other particular embodiments of the foregoing, the checkpoint protein is OX40L, 4-1BBL or the extracellular domain thereof.

Figure 9A:
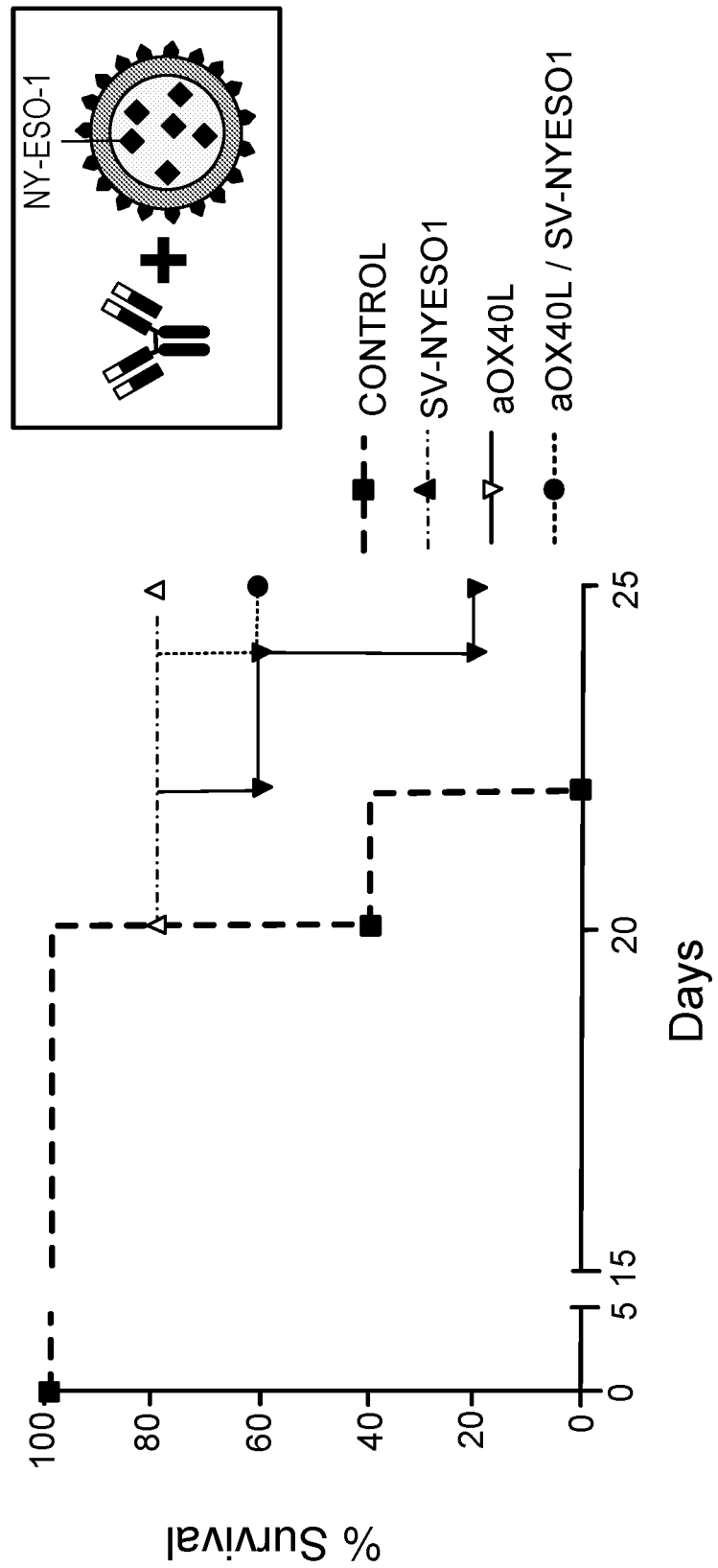
FIGS. 9A and 9B present Kaplan-Meir survival plots of untreated control animals (n=5) and treated animal groups (n=5 per group).
Figure 9B:
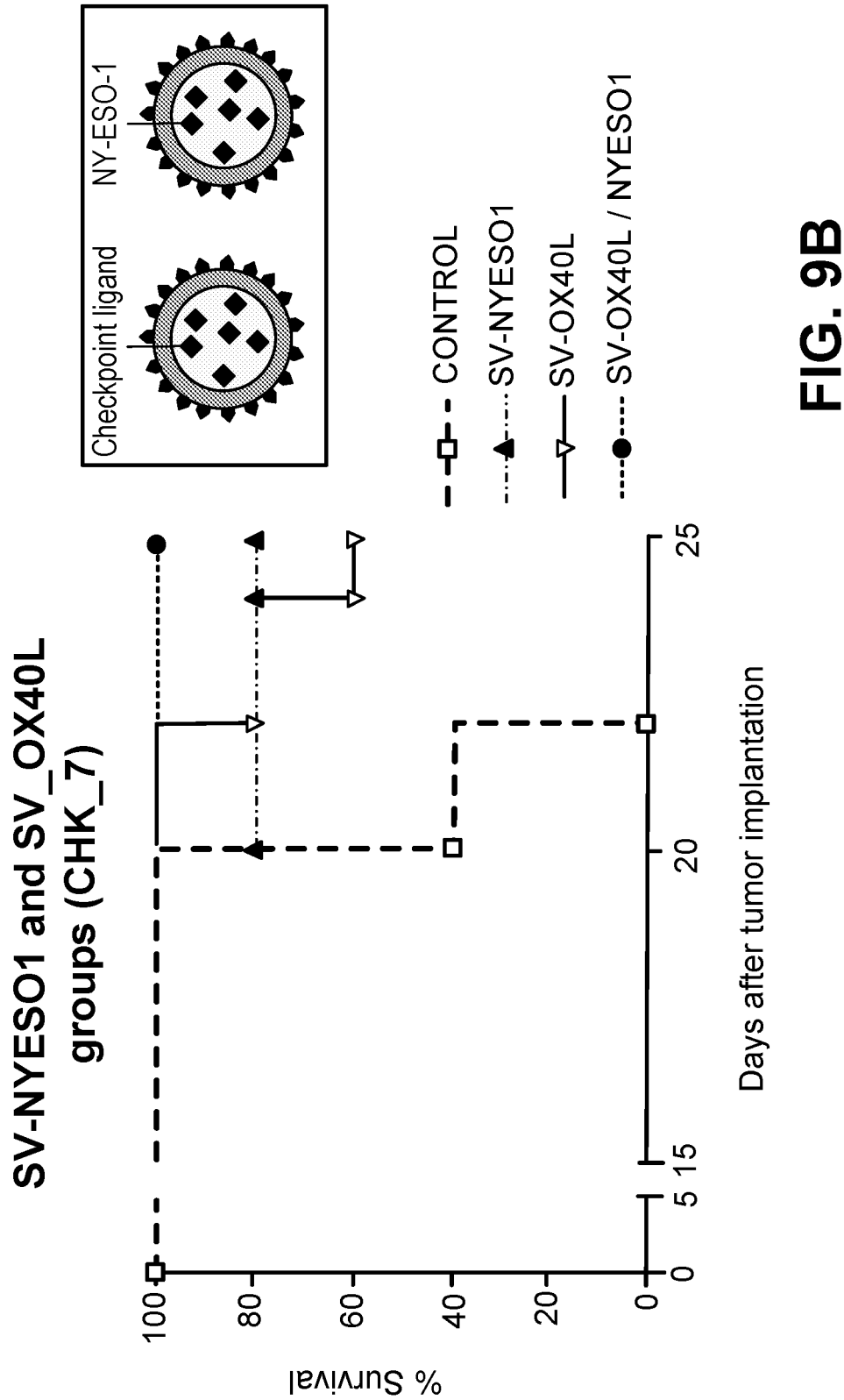

The invention is based, at least in part, on the discovery that a Sindbis virus vector encoding an immune checkpoint protein, such as the extracellular domain of a checkpoint protein, e.g., PD-1, OX40L, or 4-1BBL, resulted in a significant decrease in tumor growth and the long-term survival of tumor-bearing mice following treatment of the animals with a Sindbis virus vector encoding the checkpoint protein or a ligand binding portion thereof. In particular, treatment of animals with a Sindbis virus vector encoding the extracellular portion of wild-type PD-1 checkpoint protein or encoding OX40L, or 4-1BBL significantly reduced tumor growth in tumored animals relative to control animals, for example, for over 2 weeks, e.g., at least 20 days in the case of PD-1 or at least 18 days in the case of 4-1BBL. Treatment of tumored animals with this vector encoding PD-1 also resulted in a greater survival of animals following implantation of tumors. For example, by day 40 after tumor implantation, percent survival of tumored animals was approximately 3-times greater for animals that had been treated with the Sindbis virus vector encoding the PD-1 checkpoint protein compared with control animals. Treatment of tumored animals with an SV vector encoding OX40L (SV-OX40L) also resulted in a greater survival of animals following implantation of tumors compared with control animals (FIG. 9B). In addition, treatment of tumored animals with an SV vector encoding 4-1BBL (SV-4-1BB) resulted in a decrease in tumor growth in animals following implantation of tumors compared with control animals (FIG. 9A).

Surprisingly and unexpectedly, treatment of tumored animals with the Sindbis virus vector encoding the checkpoint protein (e.g., WT PD-1), as exemplified herein, resulted in a significant reduction in tumor growth compared with tumored animals that had been treated with an anti-PD-1 antibody, e.g., a more conventional checkpoint protein inhibitor treatment, and also compared with untreated control animals. In addition, and surprisingly, a significantly higher percentage of tumored animals survived following treatment with the Sindbis virus vector encoding the checkpoint protein (e.g., WT PD-1) compared with tumored animals that were treated with checkpoint inhibitor treatment with anti-PD-1 antibody.

Without wishing or intending to be bound by theory, following the administration of a Sindbis virus vector encoding an immune checkpoint protein, such as, e.g., PD-1, to a subject, large quantities of the checkpoint protein are expressed by the virus vector and soluble checkpoint protein is secreted systemically. Such large quantities of the checkpoint protein then circulate in a treated subject and are available to bind the cognate ligand, such as PD-L1, on tumor cells. The large amount of the checkpoint protein produced following administration of the Sindbis viral vector may thus directly compete with the binding of tumor cell-expressed cognate ligand (e.g., PD-L1) to T-cell expressed checkpoint protein (e.g., PD-1), thereby effectively blocking the binding of T-cell-expressed checkpoint protein to the tumor cell-expressed, interacting ligand. In such a system, the checkpoint protein encoded by the Sindbis virus vector, expressed in and produced from infected cells, may "flood" the tumor environment with soluble checkpoint protein that binds to the interacting ligand on tumor cells. Because of the occupation of the tumor-cell expressed ligand (e.g., cognate receptor protein, such as PD-L1) by the circulating checkpoint protein (e.g., PD-1), the tumor cell is unable to bind to cytotoxic T cell-expressed checkpoint protein. Consequently, cytotoxic T cells expressing checkpoint protein (e.g., PD-1) are not bound to and do not interact with cognate ligand on tumor cells (e.g., PD-L1), and the T cell cytotoxic activity is maintained and directed against the tumor cells, which are killed. Administration regimens for the checkpoint protein encoding viral vectors as described herein can be determined by a medical practitioner or clinician having skill in the art.

PD-1, the Programmed Death 1 (PD-1) protein, is a key immune checkpoint protein (receptor protein) that is expressed by activated T cells and mediates immunosuppression. PD-1 functions mainly in peripheral tissues where T cells may encounter the immunosuppressive PD-1 ligands PD-L1 (B7-H1) and PD-L2 that are expressed by tumor cells, stromal cells, or both. PD-1 produced in significant quantity by the Sindbis virus vector described herein serves to bind large quantities of PD-L1 on tumor cells, thus effectively inhibiting the normal interaction between cell-expressed PD-1 and PD-L1. Consequently, T-cell responses could be enhanced in vitro and could also mediate antitumor activity. Blockade of inhibitory receptors such as PD-L1 on tumors by the relatively large-scale, in vivo availability of Sindbis virus vector-produced, soluble checkpoint protein molecules encoded and expressed by the polynucleotides, Sindbis virus vectors and virus particles described herein offer a beneficial approach to prevent the inhibition of an anti-tumor immune response by T-cells and to augment the anti-tumor activity of T-cells whose inhibitory receptors are not blocked by binding to cognate ligand/receptors on tumor cells. The soluble checkpoint proteins expressed by the viral vectors as described herein may further act as decoys that bind ligand/receptors on tumor cells and block binding of the tumor cell ligand/receptor to the same checkpoint proteins that are expressed on the surfaces of effector T cells, such as cytotoxic T cells (CD8+ T cells). Such binding of the Sindbis virus vector-expressed checkpoint protein (or ligand binding portion thereof) to the cognate receptor protein expressed on tumor cells prevents a tumor cell from binding to the cytotoxic T cell that expresses the checkpoint protein, thereby preventing T cell anergy, which allows the cytotoxic T cell to kill the tumor.

Figure 8:
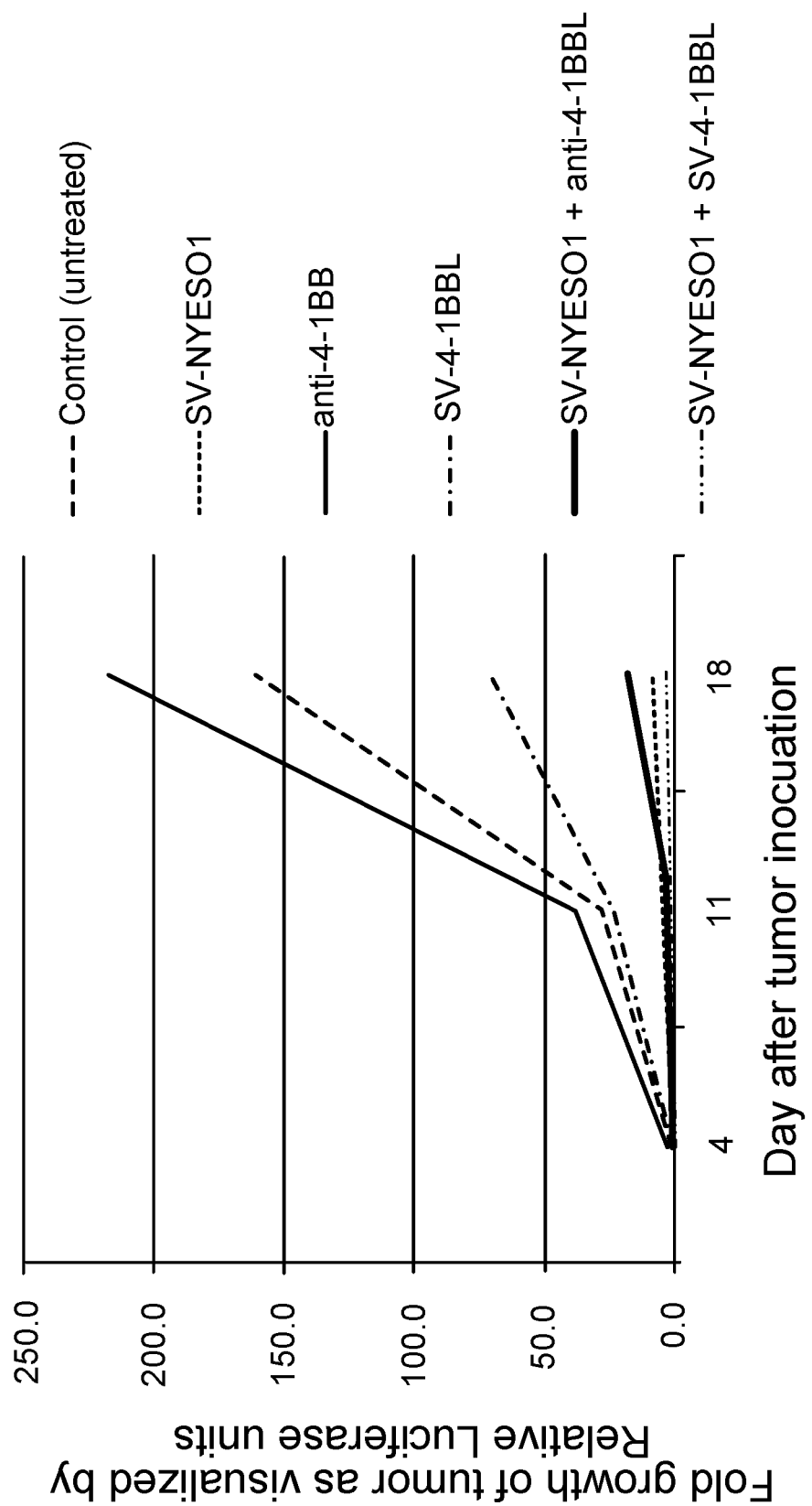
FIG. 8 presents a graph showing tumor growth curves over time (days) of treated and untreated (control) mice (n=5 for each group) as described in Example 5. Tumor growth curves are shown as fold changes relative to the bioluminescence on the first image taken of the same mouse before start of treatment.

In another embodiment, the treatment of tumored animals with the Sindbis virus vector encoding 4-1BBL, as exemplified herein, surprisingly resulted in a significant reduction in tumor growth compared with tumored animals that had been treated with an anti-4-1BB antibody, e.g., a more conventional checkpoint protein inhibitor treatment, compared with untreated control animals. (FIG. 8). In addition, and surprisingly, a significantly higher percentage of tumored animals survived following treatment with the Sindbis virus vector encoding the checkpoint protein OX40L compared with tumored animals that were treated with checkpoint inhibitor treatment with anti-OX40 antibody. (FIGS. 9A and 9B). Of note, combination treatment of tumored animals involving the administration of a Sindbis virus vector encoding the TAA, NY-ESO-1, plus a Sindbis virus vector encoding either 4-1BBL (SV4-1BBL) or OX40L (SV-OX40L) to the animals resulted in a significant reduction in tumor growth and a significantly higher percentage of survival of tumored animals, respectively, compared with antibodies directed against the respective checkpoint protein and with untreated controls.

In an embodiment, the immune response involves the activity of cytotoxic T cells which express checkpoint proteins on their surface, but are not made anergic by binding to cognate ligand expressed by tumor cells. In this embodiment, the checkpoint protein produced following administration of the Sindbis virus vector encoding the checkpoint protein binds to tumor cell-expressed ligand and prevents the tumor ligand from binding to and inactivating the anti-tumor activity that specifically kills the cancer or tumor cells. In an embodiment, the SV-encoded checkpoint protein-Ig fusion proteins as described and exemplified herein e.g., SV_PD-1, may facilitate binding to cells through the CH3 portion of the fusion protein, as well as trigger antibody dependent cell cytotoxicity (ADCC). Such checkpoint protein-Ig fusion proteins as described and exemplified herein may also be more stably expressed and have a longer half-life in vivo due to the Ig region components in the fusion protein.

The molecularly engineered viral vectors described herein provide an efficient and effective delivery system designed to harbor the genetic information of one or more checkpoint protein molecules and to promote a specific immune response, which ultimately allows cytotoxic T cells (e.g., effector CD8+ T cells) to remain activated to specifically kill the cancer or tumor.

The invention generally features virus vector-based compositions and methods that are useful for treating cancer and tumorigenesis and/or the symptoms thereof in a subject in need thereof, such as a patient having cancer. Methods utilizing viral vectors, which are designed to harbor polynucleotides encoding a checkpoint protein or a cognate binding portion thereof as described herein, involve administering a therapeutically effective amount of the viral vector, a viral particle, or a pharmaceutical composition comprising the viral vector or particle to a subject (e.g., a mammal such as a human), in particular, to elicit a T-cell-mediated immune response to the subject's cancer or tumor.

In an embodiment, particularly for the treatment and therapy of cancers, the polynucleotides, viral vectors and viral particles described herein may encode one or more checkpoint protein molecules, which following expression, bind to ligands with which they specifically interact.

In an embodiment, a wild-type (non-mutated) checkpoint protein is encoded by the Sindbis virus vector. In an embodiment, the wild-type checkpoint protein may bind more effectively to its cognate ligand than a checkpoint protein that has been genetically mutated or altered. In a particular embodiment, a wild-type PD-1 checkpoint protein is encoded by the Sindbis virus vector.

Tumor Associated Antigens (TAAs)

In some embodiments, the tumor associated antigens from which the epitopes that may be expressed by polynucleotides and viral vectors described herein are derived may be associated with, or expressed by, e.g., either extracellularly or intracellularly, a cancer or tumor, such as, without limitation, a/an ovarian cancer, breast cancer, testicular cancer, pancreatic cancer, liver cancer, colorectal cancer, thyroid cancer, lung cancer, prostate cancer, kidney cancer, melanoma, squamous cell carcinoma, chronic myeloid leukemia, acute lymphoblastic leukemia, acute myelogenous leukemia, chronic lymphocytic leukemia, promyelocytic leukemia, multiple myeloma, B-cell lymphoma, bladder carcinoma, head and neck cancer, esophageal cancer, brain cancer, pharynx cancer, tongue cancer, synovial cell carcinoma, neuroblastoma, uterine cancer, fibrosarcoma, myxosarcoma, liposarcoma, chondrosarcoma, osteogenic sarcoma, chordoma, angiosarcoma, endotheliosarcoma. lymphangiosarcoma, synovioma, mesothelioma, Ewing's tumor, leiomyosarcoma, rhabdomyosarcoma, basal cell carcinoma, epidermoid carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms'tumor, cervical cancer, small cell lung carcinoma, epithelial carcinoma, glioma, astrocytoma, medulloblastoma, craniopharyngioma, ependymoma, pinealoma. Hemangioblastoma, acoustic neuroma, oligodendroglioma, meningioma, neuroglioma, and retinoblastoma.

Additional examples of TAAs are known in the art and are described, for example, in Reuschenbach et al., *Cancer Immunol. Immunother.* 58:1535-1544 (2009); Parmiani et al., J. Nat. Cancer Inst. 94:805-818 (2002); Zarour et al., *Cancer Medicine.* (2003); Bright et al., Hum. *Vaccin. Immunother.* 10:3297-3305 (2014); Wurz et al., Ther. Adv. Med. Oncol. 8:4-31 (2016); Criscitiello, Breast Care 7:262-266 (2012); Chester et al., *J. Immunother. Cancer* 3:7 (2015); Li et al., *Mol. Med. Report* 1:589-594 (2008); Liu et al., *J. Hematol. Oncol.* 3:7 (2010); Bertino et al., *Biomed. Res. Int.* 731469 (2015); and Suri et al., *World J. Gastrointest. Oncol.* 7:492-502 (2015).

Any tumor associated antigen (TAA) having epitopes and expressed by a cancer cell or solid tumor can be utilized in conjunction with the compositions and methods described herein. However, it is expected that variability may exist in the efficacy of different TAAs and their associated epitopes to induce or increase an immune response in a subject, because some TAAs and/or their epitopes may potentially induce more robust responses (i.e., immunodominant TAAs). Relevant reports, e.g., preclinical and clinical study reports, can be used to guide the choice of TAAs or epitopes thereof to be incorporated into a polynucleotide (minigene), viral vector, viral particle, or pharmaceutical composition of the invention. In some embodiments, coding sequences of TAAs or the epitopes thereof that are capable of inducing a robust immune response, that bind MHC class I proteins with high affinity, or that bind MHC class II proteins with high affinity are incorporated into the polynucleotide, viral vector, viral particle, or pharmaceutical composition of the invention. By way of example, NY-ESO-1, the cancer-testis antigen, is desirable for use as a tumor associated antigen for cancer immunotherapy, because it is expressed in several different cancer and tumor types, e.g., breast cancer, lung cancer, melanoma, as well as in the testis and placenta; however, it is not expressed in other normal adult tissues.

Ways in which TAAs may be selected for inclusion in virus vectors are described in co-pending PCT Application No. PCT/US18/20985, the contents of which are incorporated by reference herein.

Sindbis Virus Vectors (T7Sindbis Vectors) Expressing Checkpoint Molecules/T-cell Costimulatory Molecules Sindbis vectors were designed to express molecules that enhance the antitumor immune response. Optimal activation of T cells requires a strong T cell receptor-peptide antigen-MHC interaction, in addition to the ligation of co-receptors, on the surface of T cells, with cognate checkpoint molecules or costimulatory molecules expressed on antigen-presenting cells (APCs). Co-signaling molecules have been shown to control T-cell activation by regulating T-cell proliferation, cytokine production, cytotoxicity, T-cell apoptosis, and survival.

The co-signaling molecules can be grouped into two superfamilies based on their structure: the immunoglobulin (Ig) superfamily and the tumor necrosis factor (TNF)/TNF receptor (TNFR) superfamily. The Ig superfamily includes the costimulatory molecule, CD28 and ICOSL. The tumor necrosis factor (TNF) superfamily contains multiple receptor/ligands that play pivotal roles in the immune response. Members of the TNF superfamily all share a TNF homology domain that can form non-covalent homotrimers. While the TNF ligands are typically expressed as cell surface molecules, the extracellular domain can be proteolytically shed from the membrane. Representative and nonlimiting members of the TNF family of costimulatory molecules include 4-1BB/4-1BBL and OX40/OX40L.

As described herein the Sindbis virus vector platform can advantageously incorporate multiple checkpoint protein/immunomodulatory molecules and/or tumor associated antigens (TAAs) to achieve optimal anti-tumor immune responses in tumored subjects.

Viruses and Viral Vectors

Alphavirus, Sindbis Virus and Sindbis Virus Vectors

Alphaviruses belong to the group IV Togaviridae family of viruses that are small, spherical, enveloped, positive-sense, single-stranded RNA viruses. Most alphaviruses infect and replicate in vertebrate hosts and in hematophagous arthropods, such as mosquitoes. Alphavirus virions are spherical with an iscoahedral nucleocapsid enclosed in a lipid-protein envelope. Alphavirus RNA is a single 42S strand of approximately $4 \times 10^6$ daltons that is capped and polyadenylated. The *Alphavirus* envelope comprises a lipid bilayer derived from the host cell plasma membrane and contains two viral glycoproteins, E1 (48,000 daltons) and E2 (52,000 daltons). A third, small E3 protein (10,000-12,000 daltons) is released from the virus as a soluble protein in alphaviruses other than Semliki Forest virus, where the E3 protein remains virus-associated.

As described herein, polynucleotides encoding an *Alphavirus* protein, or a fragment thereof, and a checkpoint protein or a ligand binding fragment thereof are embraced by the invention. In addition, the present invention encompasses viral vectors and particles that are pseudotyped with proteins, e.g., envelope proteins, from other virus types. The polynucleotides, viral vectors and viral particles described herein encompass nucleic acid sequences and polypeptide sequences of members of the *Alphavirus* genus, including various strains, antigenic complexes, species and subtypes. Encompassed by the invention are alphaviruses, phylogenetically related alphaviruses, *Alphavirus* complexes, and their structural components, such as envelope proteins, e.g., E1, as described, for example, in Powers, A. M. et al., 2011, *J. Virol.*, 75 (21):10118-10131. Nonlimiting examples of alphaviruses, and polynucleotides and proteins thereof, as well as fragments of their polynucleotides and proteins, that may be used in the polynucleotides, viral vectors and viral particles as described herein include Barmah Forest virus, Barmah Forest virus complex, Eastern equine encephalitis virus (EEEV), Eastern equine encephalitis virus complex, Middelburg virus, Middelburg virus complex, Ndumu virus, Ndumu virus complex, Semliki Forest virus, Semliki Forest virus complex, Bebaru virus, Chikungunya virus, Mayaro virus, Subtype Una virus, O'Nyong Nyong virus, Subtype Igbo-Ora virus, Ross River virus, Subtype Getah virus, Subtype Bebaru virus, Subtype Sagiyama virus, Subtype Me Tri virus, Venezuelan equine encephalitis virus (VEEV), VEEV complex, Cabassou virus, Everglades virus, Mosso das Pedras virus, Mucambo virus, Paramana virus, Pixuna virus, Western equine encephalitis virus (WEEV), Rio Negro virus, Trocara virus, Subtype Bijou Bridge virus, Western equine encephalitis virus complex, Aura virus, Babanki virus, Kyzylagach virus, Sindbis virus, Ockelbo virus, Whataroa virus, Buggy Creek virus, Fort Morgan virus, Highlands J virus, Eilat virus, Salmon pancreatic disease virus (SPDV), Southern elephant seal virus (SESV), Tai Forest virus and Tonate virus.

As an *Alphavirus*, Sindbis virus is a small, enveloped, positive-sense, single strand RNA virus. Other members of the *Alphavirus* genus include, without limitation, Semliki Forest virus (SFV), Venezuelan equine encephalitis virus (VEEV) and Ross River Virus (RRV). Alphaviruses, including Sindbis virus, form spherical particles of 60-70 nm in diameter; the icosahedral structures of many alphaviruses have been defined to very high resolutions by cryo-electron microscopy (cryo-EM) and crystallographic studies, revealing details of the interactions between the structural proteins (Jose, J. et al., 2009, *Future Microbiol.*, 4:837-856). The genome is composed of a single strand of positive-sense RNA that is approximately 11 to 12 kb in length and encodes four nonstructural proteins (nsP1-nsP4) involved in virus replication and pathogenesis, and five structural proteins that compose the virion particle, i.e., the nucleocapsid protein C and the envelope proteins, P62 (proteolytically cleaved into the mature envelope proteins E2 and E3) and the E1 protein. Alphaviruses exhibit efficient replication and have broad range of susceptible and permissive hosts; therefore, these viruses are highly suitable for heterologous gene expression and as gene therapy delivery vectors. Alphavirus vectors are suitable for use in encoding the polynucleotides (minigenes) for delivering the multi-epitopes of tumor associated antigens as described herein.

Any Sindbis viral vector is suitable for use in conjunction with the polynucleotides, virus vectors, compositions and methods of the present invention, including replication-competent vectors (see, e.g., U.S. Pat. No. 8,282,916) and replication-defective vectors (see, e.g., U.S. Pat. Nos. 7,303, 898, 7,306,792, and 8,093,021). Replication-defective vectors are preferred for use in the present invention, as they offer another layer of protection against infection of healthy tissues. Sindbis vectors can also be constructed to contain more than one subgenomic promoter to express more than one gene using methods known in the art.

By way of example, to produce the pT7StuI-R/epitope vector, the replicon plasmid encoding the Sindbis replicase genes (nsP1-nsP4) and a helper plasmid, encoding the viral structural genes (capsid protein C, E1, E2, E3, and 6K), were transcribed in vitro. To limit viral replication in vivo, the replicon genes have been separated from the structural genes, which additionally contain a mutated packaging signal to prevent incorporation into virus particles (Bredenbeek, P. J. et al., 1993, *J Virol* 67: 6439-6446). Virus particles were produced by transient transfection of baby hamster kidney (BHK) cells with in vitro synthesized Sindbis replicon RNA and helper RNA transcripts. Within the cell, genomic RNA was replicated by the Sindbis replicase and expressed from the capped replicon RNA transcript. Structural proteins were expressed from the helper RNA transcript. Only the replicon RNA was packaged into the capsid to form the nucleocapsid, which then associates with the viral glycoproteins E1 and E2 and buds out of the cell. The resulting virion contained the capped SV single-stranded RNA message for nsP1-nsP4 genes, which encode the viral replicase, a subgenomic promoter (Psg) from which the replicase can transcribe an inserted gene of interest and a poly A tail. Example 2 herein describes methods to produce a Sindbis viral vector encoding a checkpoint protein or a ligand binding portion thereof.

Lentivirus

Lentiviral vectors are particularly useful for long-term expression of genes, as they have the ability to infect both dividing and non-dividing cells. Third generation lentiviral systems are preferred for increased safety (Breckpot, K., et al., 2007, *Gene Ther,* 14: 847-862). These include, e.g., a transfer plasmid into which nucleic acid sequences encoding two or more epitopes of a tumor associated antigen is inserted, a packaging plasmid for gag and pol genes and another packaging plasmid for the rev gene. For optimal expression, the transfer expression vectors contain a splice donor, a packaging signal (psi), a Rev-responsive element (RRE), splice acceptor, central poly-purine tract (cPPT), and Wood chuck hepatitis virus transcriptional response element (WPRE) (Shaw and Cornetta, 2014, Biomedicines, 2:14-35). Transfer vector constructs may also contain a promoter for expression in mammalian cells. Constitutive promoters, such as the cytomegalovirus (CMV), mammalian beta-actin, or ubiquitin promoters may be incorporated into a composition of the invention. In some embodiments, tissue-specific promoters are utilized, such as CD4+T cell-specific promoters.

Plasmids for generating lentiviral vectors can be obtained from Addgene (Cambridge, MA, a non-profit plasmid repository) and modified, as necessary, using standard techniques in the art. Standard $3^{rd}$ generation packaging plasmids can be used. Suitable transfer vectors include, for example, pLX301, pFUGW, and pWPXL. These vectors contain all of the requisite characteristics mentioned above. To increase safety, the lentivirus transfer vectors can be mutated to decrease integration and increase episomal replication in infected cells. For instance, using standard techniques known in the field, the following modifications can be performed: a deletion within the U3 region of the 3' LTR to create a self-inactivating LTR (SIN-LTR) is made; LTR att sites within the U3 and U5 LTR regions are deleted or mutated; the 3' LTR-proximal polypurine tract (PPT) are deleted or modified (Shaw and Cornetta, 2014).

Pseudotyped viral vectors and virions are also suitable for use in connection with the polynucleotides and compositions of the invention. Such virions contain a viral particle and one or more foreign virus envelope proteins. (D. A. Sanders, 2002, *Curr. Opin. Biotechnol.,* 13:437-442). In some embodiments, a viral vector of the invention may be a lentivirus containing an *Alphavirus* protein or a fragment thereof, e.g., an envelope protein or a functional fragment thereof. In some embodiments, a viral vector of the invention may be a lentivirus containing a Sindbis virus envelope glycoprotein, or certain Sindbis virus envelope glycoproteins. By way of example, to produce a construct (e.g., a pseudotyped viral vector) comprising a lentivirus backbone pseudotyped with one or more Sindbis envelope proteins, a Sindbis envelope plasmid, e.g., T7 DM helper #101 (U.S. Pat. No. 8,093,021) is transfected into BHK or 293 cells along with the lentiviral plasmids resulting in pseudotyped virions.

Retrovirus

Retroviral vectors are also suitable for use according to the invention. In some embodiments, the retroviral vector is Moloney murine leukemia virus (Mo-MuLV) pseudotyped with Sindbis envelope proteins. Pseudotyping can be performed using methods known in the art (see, e.g., Sharkey et al., 2001, *J. Virology,* 75 (6):2653-2659). In some embodiments, the Mo-MuLV-based retrovirus particles are engineered to include and express the glycoproteins of the *Alphavirus* Ross River virus (RRV) using methods known and practiced in the art.

Sindbis Virus Envelope Pseudotyped Vectors

The Sindbis virus (SV) envelope is advantageous for use as a gene or polynucleotide delivery vector. SV is a blood-borne virus with a relatively long half-life. Stable virus is easily produced and can be concentrated for administration. Modification of the Sindbis E2 envelope protein, which binds to cell surface molecules, does not affect the E1 fusogenic envelope protein that is required for cell entry, thus allowing for engineered targeting of the virus. Sindbis virus specifically targets tumors by interacting with the high-affinity laminin receptor (LAMR) (U.S. Pat. No. 7,306, 792), which is found in the 40S ribosome and is overexpressed by many tumors (e.g., breast, thyroid, colon, prostate, stomach, pancreas, ovary, melanocytes, lung, liver, uterus), but does not infect normal tissues. As a blood-borne virus, Sindbis virus is capable of contacting disseminated metastatic tumor cells via the bloodstream.

Sindbis viral envelope structural proteins can pseudotype other viral vectors, such as lentivirus, retrovirus and Vesicular Stomatitis virus (VSV) to improve their targeting capabilities and increase virion stability. In particular, the Sindbis-ZZ protein, designed to contain the Fc binding domain of *S. aureus* protein A inserted into the E2 envelope protein (U.S. Pat. No. 6,432,699), is useful in conjunction with cell surface specific antibodies for redirecting the targeting of SV and other vectors.

In certain embodiments in which long-term, stable expression of encoded protein is desired, retroviral or lentiviral vectors pseudotyped with wild type or engineered Sindbis virus envelope proteins are employed. Lentiviral vectors are advantageous for infection of both dividing and non-dividing cells. Like the Sindbis virus genome, the lentivirus genome can be split into two or three vectors, and genes can be modified or deleted to improve safety. A retrovirus subtype lentivirus naturally integrates into the host genome. However, vectors containing either long terminal repeats (LTR) or integrase enzyme mutations can exist as stable, non-integrating episomes in the cell nucleus (Breckpot, K., et al., 2007, Gene Ther., 14:847-862).

In particular embodiments, a therapeutic composition of the invention comprises a replication defective Sindbis virus described in U.S. Pat. Nos. 7,303,898, 9,423,401; 8,530,232; or 8,093,021.

Pharmaceutical Compositions

The present invention includes pharmaceutical compositions or formulations for treating subjects who are afflicted with cancer or a tumor, or who are at risk of developing cancer or a tumor. In an embodiment, the pharmaceutical composition includes viral vector, e.g., a Sindbis virus vector containing a polynucleotide encoding a checkpoint protein or a checkpoint protein minibody as described herein, or a cognate ligand binding portion thereof, and a pharmaceutically acceptable carrier, excipient, or diluent. In an embodiment, the pharmaceutical composition includes a Sindbis viral vector or a pseudotyped viral vector as described herein and a pharmaceutically acceptable carrier, excipient, or diluent. When formulated in a pharmaceutical composition, a therapeutic compound or product of the present invention can be admixed with a pharmaceutically acceptable carrier, diluent, or excipient.

The administration of a composition comprising the therapeutic Sindbis vectors described herein for the treatment of a cancer or tumor may be by any suitable means that results in a concentration of the therapeutic that, combined with other components, is effective in ameliorating, reducing, or stabilizing a cancer in a subject. The composition may be administered systemically, for example, formulated in a pharmaceutically-acceptable buffer such as physiological saline. Routes of administration include, for example, subcutaneous (s.c.), intravenous (i.v.), intraperitoneal (i.p.), intramuscular (i.m.), or intradermal administration, e.g., by injection, that optimally provide continuous, sustained levels of the agent in the patient. The amount of the therapeutic agent to be administered varies depending upon the manner of administration, the age, physical condition and body weight of the patient, and with the clinical symptoms of the cancer or tumor. Generally, amounts will be in the range of those used for other viral vector-based agents employed in the treatment of a cancer or tumor, although in certain instances lower amounts will be needed if the agent exhibits increased specificity. A composition is administered at a dosage that shows a therapeutic effect, such as increasing immune cell (e.g., effector T cell; CD8+ T cell) levels, or that decreases cancer cell proliferation or reduces tumor size, as determined by methods known to one skilled in the art.

The therapeutic agent(s) may be contained in any appropriate amount in any suitable carrier substance, and is/are generally present in an amount of 1-95% by weight of the total weight of the composition. The composition may be provided in a dosage form that is suitable for a parenteral (e.g., subcutaneous, intravenous, intramuscular, or intraperitoneal) administration route, such that the agent, such as a viral vector described herein, is systemically delivered. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Pharmaceutical compositions according to the invention may be formulated to release the active agent substantially immediately upon administration or at any predetermined time or time period after administration. The latter types of compositions are generally known as controlled release formulations, which include (i) formulations that create a substantially constant concentration of the agent within the body over an extended period of time; (ii) formulations that after a predetermined lag time create a substantially constant concentration of the drug within the body over an extended period of time; (iii) formulations that sustain action during a predetermined time period by maintaining a relatively, constant, effective level in the body with concomitant minimization of undesirable side effects associated with fluctuations in the plasma level of the active substance (sawtooth kinetic pattern); (iv) formulations that localize action by, e.g., spatial placement of a controlled release composition adjacent to or in contact with a tumor; (v) formulations that allow for convenient dosing, such that doses are administered, for example, once every one or two weeks; and (vi) formulations that target a cancer using carriers or chemical derivatives to deliver the therapeutic agent to a particular cell type (e.g., cancer or tumor cell). For some applications, controlled release formulations obviate the need for frequent dosing during the day to sustain the plasma level of the administered agent at a therapeutic level.

Methods by which to obtain controlled release in which the rate of release outweighs the rate of metabolism of the agent in question are not meant to be limiting. By way of example, controlled release is obtained by appropriate selection of various formulation parameters and ingredients, including, e.g., various types of controlled release compositions and coatings. Thus, the therapeutic agent is formulated with appropriate excipients into a pharmaceutical composition that, upon administration, releases the agent in a controlled manner. Examples include single or multiple unit tablet or capsule compositions, oil solutions, suspensions, emulsions, microcapsules, microspheres, molecular complexes, nanoparticles, patches, and liposomes.

The pharmaceutical composition may be administered parenterally by injection, infusion or implantation (subcutaneous, intravenous, intramuscular, intraperitoneal, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation, and can be found, for example, in Remington: The Science and Practice of Pharmacy, supra.

Compositions for parenteral delivery and administration may be provided in unit dosage forms (e.g., in single-dose ampules), or in vials containing several doses and in which a suitable preservative may be added (see below). The composition may be in the form of a solution, a suspension, an emulsion, an infusion device, or a delivery device for implantation, or it may be presented as a dry powder to be reconstituted with water or another suitable vehicle before use. Apart from the active agent (e.g., a polynucleotide, viral vector or particle described herein), the composition may include suitable parenterally acceptable carriers and/or excipients. The active therapeutic agent(s) may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing, agents.

In some embodiments, the composition comprising the active therapeutic(s) (i.e., a polynucleotide, viral vector or particle described herein) is formulated for intravenous delivery. As noted above, the pharmaceutical compositions according to the invention may be in the form suitable for sterile injection. To prepare such a composition, the suitable therapeutic(s) are dissolved or suspended in a parenterally acceptable liquid vehicle. Acceptable vehicles and solvents that may be employed include water, water adjusted to a suitable pH by addition of an appropriate amount of hydrochloric acid, sodium hydroxide or a suitable buffer, 1,3-butanediol, Ringer's solution, isotonic sodium chloride solution and dextrose solution. The aqueous formulation may also contain one or more preservatives (e.g., methyl, ethyl or n-propyl p-hydroxybenzoate). In cases where one of the agents is only sparingly or slightly soluble in water, a dissolution enhancing or solubilizing agent can be added, or the solvent may include 10-60% w/w of propylene glycol or the like.

Methods of Delivery

In embodiments, the viral vector, viral particle, or pharmaceutical composition of the invention may be delivered, such as to a cell (particularly a cancer or tumor cell) in any manner such that the viral vector, particle or composition is functional and active to express the encoded sequences. Illustratively, a Sindbis virus vector harboring a polynucleotide encoding a checkpoint protein or a ligand binding portion thereof may be delivered to cells for heterologous expression in the cells. Thus, the present invention features viral vectors, or viral particles delivered to a cell by contacting the cell with the Sindbis virus vector, or a composition comprising the vector, or viral particles, or by heterologously expressing the polynucleotides, viral vectors, or viral particles in the cell.

Polynucleotide Therapy

One therapeutic approach for treating a cancer or tumorigenesis is polynucleotide therapy using a polynucleotide encoding a checkpoint protein molecule as described herein. Expression of such polynucleotides or nucleic acid molecules in relevant cells and production of the protein is expected to stimulate an immune response, such as a cytotoxic T cell response, reduce survival of the cell and/or increase cell death. Such nucleic acid molecules can be delivered to cells of a subject having a cancer or tumor. The nucleic acid molecules must be delivered to the cells of a subject in a form in which they can be taken up so that therapeutically effective levels of the encoded products can be produced.

Transducing viral (e.g., retroviral, adenoviral, and adeno-associated viral) vectors can be used for delivering encoded proteins and peptide products to cells, especially because of their high efficiency of infection and stable integration and expression (see, e.g., Cayouette et al., *Human Gene Therapy*, 8:423-430, 1997; Kido et al., *Current Eye Research*, 15:833-844, 1996; Bloomer et al., *Journal of Virology*, 71:6641-6649, 1997; Naldini et al., *Science*, 272: 263-267, 1996; and Miyoshi et al., *Proc. Natl. Acad. Sci. U.S.A.*, 94:10319, 1997).

For example, a polynucleotide encoding a checkpoint protein or a ligand binding portion thereof, as well as a checkpoint protein minibody as described herein, can be cloned into a vector, e.g., a Sindbis virus vector or a pseudotyped virus vector, as described herein, and expression can be driven from its endogenous promoter, from a retroviral long terminal repeat, or from a promoter specific for a target cell type of interest. Other viral vectors that can be used include, for example, a vaccinia virus, a bovine papilloma virus, or a herpes virus (see, for example, the vectors of Miller, *Human Gene Therapy*, 15-14, 1990; Friedman, *Science*, 244:1275-1281, 1989; Eglitis et al., *BioTechniques*, 6:608-614, 1988; Tolstoshev et al., *Current Opinion in Biotechnology*, 1:55-61, 1990; Sharp, *The Lancet*, 337:1277-1278, 1991; Cornetta et al., *Nucleic Acid Research and Molecular Biology*, 36:311-322, 1987; Anderson, *Science*, 226:401-409, 1984; Moen, *Blood Cells*, 17:407-416, 1991; Miller et al., *Biotechnology*, 7:980-990, 1989; Le Gal La Salle et al., *Science*, 259:988-990, 1993; and Johnson, *Chest*, 107:77S-83S, 1995). Retroviral vectors are well developed and have been used, for example, as described in Rosenberg et al., *NEJM*, 323:370, 1990; Anderson et al., and U.S. Pat. No. 5,399,346. In some embodiments, the viral vector containing a polynucleotide encoding a checkpoint protein, a ligand binding portion thereof, or a checkpoint protein minibody is administered systemically. In an embodiment, administration is performed intravenously or intraperitoneally.

As will be appreciated by the skilled practitioner, non-viral approaches can also be employed for the introduction of a therapeutic polypeptide to a cell of a subject requiring induction of a T cell immune response to inhibit growth of a cancer or tumor or to induce cancer or tumor cell death. For example, a nucleic acid molecule can be introduced into a cell by administering the nucleic acid in the presence of lipofection (Feigner et al., *Proc. Natl. Acad. Sci. U.S.A.* 84:7413, 1987; Ono et al., *Neuroscience Letters*, 17:259, 1990; Brigham et al., *Am. J. Med. Sci.*, 298:278, 1989; Staubinger et al., *Methods in Enzymology*, 101:512, 1983), asialoorosomucoid-polylysine conjugation (Wu et al., *Journal of Biological Chemistry*, 263:14621, 1988; Wu et al., *Journal of Biological Chemistry*, 264:16985, 1989), or by micro-injection under surgical conditions (Wolff et al., *Science*, 247:1465, 1990). In addition, the nucleic acids can be administered in combination with a liposome and protamine.

Gene transfer can also be achieved using in vitro transfection methods. Such methods include the use of calcium phosphate, DEAE dextran, electroporation, and protoplast fusion. Liposomes can also be potentially beneficial for delivery of DNA into a cell.

cDNA expression for use in polynucleotide therapy methods can be directed from any suitable promoter (e.g., the Sindbis virus promoter, the human cytomegalovirus (CMV), simian virus 40 (SV40), or metallothionein promoters), and regulated by any appropriate mammalian regulatory element. For example, if desired, enhancers known to preferentially direct gene expression in specific cell types can be used to direct the expression of a nucleic acid. The enhancers used can include, without limitation, those that are characterized as tissue- or cell-specific enhancers. Alternatively, regulation can be mediated by the cognate regulatory sequences or, if desired, by regulatory sequences derived from a heterologous source, including any of the promoters or regulatory elements described above.

Methods of Administration and Treatment Protocols

Provided are methods of administering a therapeutic agent to a subject in need, such as a subject having cancer or a tumor, or identified as needing such treatment), in which an effective amount of a polynucleotide, viral vector, or viral particle as described herein, or a composition described herein, is administered to a subject to produce a therapeutic effect. According to the present invention, a therapeutic effect includes, without limitation, an immune response against cancer and tumor cells expressing checkpoint protein binding molecules (e.g., receptors that bind checkpoint protein) on their surface, e.g., by effector T cells (e.g., CD8+ T cells). Identifying a subject in need of such treatment can be achieved based on the judgment of a subject or a health or medical care professional and can be subjective (e.g. opinion) or objective (e.g. measurable by a test or diagnostic method).

The therapeutic methods of the invention (which include prophylactic treatment) in general comprise administration of a therapeutically effective amount of the agents described herein, such as a polynucleotide, a viral vector, a viral particle, or composition containing the aforementioned agents, to a subject (e.g., animal, human) in need thereof, including a mammal, particularly a human. Such treatment will be suitably administered to subjects, particularly humans, suffering from, having, susceptible to, or at risk for cancer or a tumor. Determination of those subjects "at risk" can be made by any objective or subjective determination by a diagnostic test or opinion of a subject or health care provider (e.g., genetic test, enzyme or protein marker or biomarker, family history, and the like). The polynucleotide and viral vector agents described herein may be also used in the treatment of any other diseases or disorders in which checkpoint proteins and their interacting binding molecules (protein receptors) may be implicated.

In preclinical studies using mice, intraperitoneal (i.p.) injections of a therapeutically effective amount of the Sindbis viral vector encoding the checkpoint protein (e.g., a checkpoint protein minibody), (~$10^5$ virus particle transforming units), resulted in an immune response directed against the tumor and a reduction in tumor growth and increased survival of treated animals (Example 2, infra). It will be appreciated by the skilled practitioner that other regimens may be necessary for achieving a maximal response in human subjects. For example, in human patients, therapeutically effective amounts of the vectors described herein can broadly range between about 6 and about 12 $Log_{10}$ vector particles/kg per treatment administered over time, e.g., between about 1 and about 8 i.p. (intraperitoneal) injections over a time period of between about 1 week and many weeks, with the possibility of injecting one or more booster injections, week, months, or years, e.g., 1 or more years, later.

Viral vectors, polynucleotides and pharmaceutical compositions of the present invention can be used therapeutically to treat patients suffering from cancer or tumors, or prophylactically to vaccinate patients at risk for certain cancers or tumors, such as a prophylactic vaccine for cancer in the general population. A prophylactically effective amount of the vectors of the present invention may range between about $10^2$ TU (transducing units) per kilogram body weight of the recipient and about $10^8$ TU kilogram body weight of the recipient. Mouse models of relevant cancers can be used to optimize dosages and regimens. To promote an effective, persistent immune response that includes both effector and memory CD8+ T cells, optimal dosage and immunization intervals are established. A CD8+ T cell response to an initial *Alphavirus* vaccine quickly contracts, allowing development of memory T cells. Prior to this contraction, additional administration of the viral vector does not increase the immune response (Knudsen, M. L. et al., 2014, *J Virol.*, 88:12438-12451). The strong type I interferon (IFN) response to *Alphavirus* RNA amplification stimulates the generation of memory T cells by activating dendritic cells to promote cross-priming (Fuertes, M. B. et al., *J Exp Med*, 208: 2005-2016).

A typical treatment regimen using a vector or composition as described herein may include SV_checkpoint protein viral vector administration followed by monitoring of lymphocytes, several times per week, using flow cytometry to determine the peak and decline of effector CD8+ T cells ($CD62L^-CD127^-$ phenotype). In an embodiment, a boost of vector can be administered allowing an increase in effector memory T cells ($CD62L^-CD127+$), central memory T cells ($CD62L^+CD127^+$) and T cells with persistent high recall capacity ($CD27^+CD43^-$). Efficacy is determined by positive immune response and low tumor recurrence.

The vectors used for immunization boost(s) are not limiting. The distribution of T cell subpopulations induced by a DNA-launched *Alphavirus* replicon can be altered by heterologous boost (Knudsen, M. L. et al., 2-14, J. Virology, 88:12438-12451). For example, boosting with a poxvirus vector (Modified Vaccinia Ankara or MVA) can boost the expansion of T cell compartments that can greatly augment efficacy. In this embodiment, the viral vector employed in the booster administration encodes multiple (e.g., two or more) epitopes of one or more tumor associated antigens. Any antigen delivery system can be used to boost the immune response induced by the vectors of the present invention. Non-limiting examples include replication-defective adenoviruses, fowl pox viruses, vaccinia virus, influenza virus, Sendai virus, naked DNA, plasmids and peptides (Woodland, D. L., 2004, *TRENDS in Immunology*, Vol. 25 (2):98-104).

Exemplary routes of vector administration include, without limitation, parenteral administration, such as by intraperitoneal, intravenous, subcutaneous, stereotactic, intramuscular, intranasal, intradermal, intraorbital, intranodular and intratumoral injection. Other modes of administration may include oral, intracranial, ocular, intraorbital, intra-aural, rectal, intravaginal, suppositories, intrathecal, inhalation, aerosol, and the like.

In a certain embodiment, the vector used for treatment is a defective Sindbis viral vector, the tumor is a cancer or tumor, such as colon cancer or ovarian cancer, and the checkpoint protein encoded by the viral vector is PD-1. In other embodiments, one or more checkpoint proteins selected from PD-L1, OX40, OX40L, CTLA-4, 4-1BB, 4-1BBL, KIR, LAG-3, IDO1, TIM-3, A2AR, B7-H3, B7-H4, B7-1/B7-2, BTLA, VISTA, or a cognate ligand binding portion thereof may be used.

Patients to whom the viral vectors of the present invention are administered may also benefit from adjunct or additional treatments, such as an anti-cancer or tumor agent, chemotherapy and/or radiation treatments, as are well known to the skilled practitioner in the art. In particular, the Sindbis viral vector encoding a checkpoint protein (SV/checkpoint protein) can be combined with chemotherapy treatment. In certain cases, SV and chemotherapy synergize (e.g., U.S. Patent Application Publication No. 2016/0008431), thus providing the potential for an improved treatment effect and/or outcome. Suitable chemotherapy includes, without limitation, chemotherapy treatment that stimulates the immune system, or that inhibits suppressor elements in the immune system, or that affects tumor cells and makes them more susceptible to T cell (or other immune cell) cytotoxicity. For example, there are certain chemotherapies that can facilitate treatment and therapy with the Sindbis viral vectors described herein, because they attenuate the activity of immunosuppressive cells, thereby enhancing immunostimulation by the viral vector. In addition, chemotherapy may enhance tumor cell susceptibility to T cell mediated cytotoxicity.

Kits

Provided are kits for the treatment or prevention of cancer or tumors. In one embodiment, the kit includes a therapeutic or prophylactic composition containing an effective amount of a polynucleotide, viral vector, or viral particle as described herein, which comprises a polynucleotide that encodes a checkpoint protein, a ligand binding portion of the checkpoint protein (e.g., an extracellular domain of the checkpoint protein), or a minibody checkpoint protein fusion protein. In an embodiment, the polynucleotide encodes an *Alphavirus* protein or a fragment thereof. In an embodiment, the *Alphavirus* protein or a fragment thereof is a Sindbis virus protein or a fragment thereof. In an embodiment, the encoded checkpoint protein is PD-1. In other embodiments, the checkpoint protein is one or more of PD-L1, OX40, OX40L, CTLA-4, 4-1BB, 4-1BBL, KIR, LAG-3, IDO1, TIM-3, A2AR, B7-H3, B7-H4, B7-1/B7-2, BTLA, VISTA, or a cognate ligand binding portion thereof. In some embodiments, the kit comprises a sterile container which contains the therapeutic or prophylactic composition; such containers can be boxes, ampoules, bottles, vials, tubes, bags, pouches, blister-packs, or other suitable container forms known in the art. The containers can be made of plastic, glass, laminated paper, metal foil, or other materials suitable for holding medicaments.

If desired, a composition comprising one or more checkpoint protein-encoding viral vector agents of the invention is provided together with instructions for administering the agent to a subject having or at risk of developing cancer or a tumor. The instructions will generally include information about the use of the composition for the treatment or prevention of the cancer or tumor. In other embodiments, the instructions include at least one of the following: description of the therapeutic agent; dosage schedule and administration for treatment or prevention of ischemia or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

One having skill in the art will appreciate that the practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides, viral vectors and viral particles of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the virus products, compositions and therapeutic methods as described, and are not intended to limit the scope of what the inventors regard as their invention.

EXAMPLES

Example 1—Methods

Vector preparation: Construction of recombinant viral vectors was performed using standard techniques well known to those of ordinary skill in the field of molecular biology, including, but not limited to, plasmid purification, restriction endonuclease digestion, ligation, transformation, polymerase chain reaction and DNA sequencing (e.g., Current Protocols in Molecular Biology, E M. Ausubel et al. (Eds), John Wiley and Sons, Inc., NY, USA. (1998) and Molecular Cloning: A Laboratory Manual (2nd Ed.), J. Sambrook, E. F. Fritsch and T. Maniatis (Eds), Cold Spring Harbor Laboratory Press, NY, USA. (1989)).

For the experiments using Sindbis viral vector encoding PD-1 (SV/PD-1) and SV/Fluc and SV/GFP as control vectors, the vectors were produced as previously described. (Tseng J. C. et al, 2004, Nat. Biotechnol., 22:70-77). Briefly, plasmids carrying the replicon (SinRep5-LacZ, SinRep5-GFP, or SinRep5-Fluc) or DHBB helper RNAs (SinRep5-tBB) were linearized with XhoI (for SinRep5-LacZ, SinRep5-GFP, and SinRep5-tBB) or PacI (for SinRep5-Fluc). In vitro transcription was performed using the mMessage mMachine RNA transcription kit (Ambion, Austin, TX). Helper and replicon RNAs were then electroporated into BHK cells and incubated at 37° C. in α-MEM supplemented with 10% FBS. After 12 hours, the medium was replaced with OPTI-MEM I (Invitrogen, Carlsbad, CA), supplemented with $CaCl_2$ (100 μg/ml), and cells were incubated at 37° C. After 24 hours, the supernatant was collected, centrifuged to remove cellular debris, and frozen at −80° C. Vector titers were determined as known in the art (Tseng J. C., et al., 2002, *J Natl Cancer Inst.*, 94:1790-1802) and were similar in all three vectors (SV/LacZ, SV/Fluc, and SV/GFP).

Cell lines and Cell Culture: Baby hamster kidney (BHK), CT26.WT cells were obtained from the American Type Culture Collection (ATCC), (Manassas, VA). BHK cells were maintained in minimum essential α-modified media (α-MEM) (Mediatech, VA) with 10% fetal bovine serum (FBS) (Atlanta Biologicals, Norcross, GA). CT26.WT cells were maintained in Dulbecco modified essential media (DMEM) containing 4.5 g/L glucose (Mediatech) supplemented with 10% FBS. All basal medium was supplemented with 100 mg/mL of penicillin-streptomycin (Mediatech) and 0.5 mg/mL of amphotericin B (Mediatech).

Virion Production: Sindbis virus vectors were produced as described in U.S. Pat. Nos. 7,303,898, 7,306,792, and 8,093,021. Briefly, plasmids carrying the replicon pT7StuI-R or DHBB helper RNAs (SinRep5-tBB) were linearized with appropriate restriction enzymes. In vitro transcription was performed using the mMessage RNA transcription kit (Ambion, TX) according to the manufacturer's instructions. Helper and replicon RNAs were then electroporated into BHK cells and incubated at 37° C. in MEM supplemented with 10% FBS. After 12 hours, the medium was replaced with OPTIMEM I (Life Sciences, CA) supplemented with $CaCl_2$ (100 g/mL) and cells were incubated at 37° C. After 24 hours, the supernatant was collected, centrifuged to remove cellular debris, and frozen at −80° C. Titers of the vectors were determined using RT-qPCR as practiced in the art.

Therapeutic Efficacy: Therapeutic efficacy was monitored in three ways: tumor volume (for subcutaneous tumors, measured with mechanical calipers), tumor luminescence and survival. Noninvasive bioluminescent imaging was performed using the IVIS Spectrum imaging system (Caliper Life Sciences, Inc., MA), and tumor growth was quantified using the Living Image 3.0 software (Caliper Life Sciences). Survival of the animals was monitored and recorded daily.

Flow cytometry: Flow cytometry was used to analyze lymphocytes extracted from organs, peritoneum or peripheral blood. Cells were treated with 1× RBC lysis buffer (eBioscience) to eliminate red blood cells. Peritoneal cells were collected and stained with various Abs, washed twice with HBSS buffer (Mediatech), and analyzed using an LSR II machine (BD Biosciences, San Jose, CA). Data were analyzed using FlowJo (Tree Star, San Carlos, CA).

Bioluminescent imaging of SV/Fluc: Tumor-bearing and tumor-free mice were injected with SV/Fluc (~$10^7$ plaque-forming units in 0.5 ml of OPTI-MEM I 0.5ml) i.p. After the treatment, bioluminescence signal was detected by IVIS at the indicated time points (Tseng, J. C. et al., 2004).

Example 2—Sindbis Virus Vector Encoding the Immune Checkpoint Protein PD-1 Provided Anti-tumor Efficacy In Vivo This Example describes studies conducted utilizing a Sindbis virus vector which contained a polynucleotide encoding the extracellular portion of PD-1, a checkpoint protein (receptor protein) expressed by T cells, which plays a role in downregulating the immune response.

Materials and Methods

Cell Lines

Baby hamster kidney cells (BHK-21; ATTC CCL-10) were maintained in minimum essential α-modified medium (α-MEM) (Corning CellGro) supplemented to contain 5% fetal bovine serum (FCS, Gibco) and 100 mg/mL penicillin-streptomycin (Corning CellGro). BHKSINLuc2 cells (ATCC CRL12071) were cultured in a manner similar to that of BHK cells, and 400 μg/mL Geneticin was included in the culture medium.

The BALB/c colon carcinoma (CT26) cell line was obtained from the American Type Culture Collection (ATCC: CRL 2638). Firefly luciferase (Fluc)-expressing CT26 cells (CT26.Fluc) were generated by stable transfection of the pGL4.20_Fluc plasmid that expresses luciferase from an SV40 promoter and has puromycin as a selection marker. The CT26 cell line expressing both Firefly luciferase and NYESO1 (CT26.Fluc.NYESO1) was generated by stably transfecting the CT26.Fluc cell line with the expression plasmid pReceiver-M02 (GeneCopoeia) that contains the polynucleotide encoding NYESO1 (NM_001327.1) under the control of the CMV promoter and that contains neomycin as a selection marker. The CT26.Fluc.NYESO1 cell line was maintained in Dulbecco's modified Eagles medium (DMEM) containing 4.5 g/L Glucose (Corning CellGro) supplemented to contain 10% FCS, 100 mg/mL penicillin-streptomycin, 7.5 μg/mL Puromycin and 800 μg/mL Geneticin. All cell lines were cultured at 37° C. and 5% $CO_2$.

Preparation of pT7StuIR-WT PD-1 Minibody Vector

The extracellular domain of the human PD-1 protein is encoded by nucleotides 69-576 of the GenBank-NCBI sequence, Ref. Seq. NM_005018.2 (FIG. 1A). The encoded human polypeptide is 59% identical and 69% similar to the mouse PD-1 sequence. To produce the Sindbis virus vector encoding PD-1 protein, the wild-type human PD-1 sequence was fused to the hinge region and the CH3 heavy chain constant region domain of human immunoglobulin (Ig) G isotype 1, IgG1 (GenBank, P01857.1). (FIG. 1A). A glycine-rich, artificial spacer or linker sequence was added between the hinge and CH3 domains to provide greater flexibility between the protein domains. Amino acid sequences were optimized for expression and function in the mouse. The sequence was synthesized by GenArt (Lifetechnologies). The PD-1 sequence fused to the IgG1 hinge region and the heavy chain constant region CH3 domain is termed a "minibody" or "minibody fragment" herein. An XbaI restriction enzyme site was included to facilitate subcloning from the GenArt pMK-RQ-Bb vector. The synthesized sequence was excised from the pMK-RQ-Bb plasmid using the restriction enzymes XbaI and PmeI. The Sindbis virus plasmid, pT7StuIR, was also digested with the XbaI/PmeI enzymes and was ligated with the PD-1 minibody fragment. Plasmid DNAs, isolated from bacterial colonies obtained following transformation with the ligation reactions, were analyzed by restriction enzyme digestion and positive plasmids were sequenced. FIG. 1B shows an amino acid sequence comparison (alignment) of the human WT-PD-1 amino acid sequence to PD-1 amino acid sequences of other species, e.g., mouse and monkey.

To produce the Sindbis virus_PD-1WT minibody viral vector (SV_PD-1WT), the DNA plasmids pT7StuIR1-PD-1 WT Minibody and T7DM-Helper (maps in FIG. 2) were linearized with PacI and XhoI restriction enzymes, respectively, before performing in vitro transcription using the mMACHINE RNA transcription kit (Ambion, Austin, TX) following the manufacturer's protocol. Helper and replicon RNAs were mixed at a 1:1 ratio and then were electroporated into BHK cells. After 8 to 10 hours, the cell culture medium was replaced with OPTI-MEM (Invitrogen), supplemented to contain 100 μg/mL CaCl₂. After 24 hours, the supernatant was collected, centrifuged to remove cellular debris and stored at –80° C.

The vector titer was determined by infecting BHK-SINLuc2 cells that expressed Firefly luciferase under the Sindbis promoter, which produced Luciferase signal only in infected cells in which the Sindbis replicase wa expressed. Briefly, $10^5$ BHKSINLUC2 cells in 12 well plates were infected with serial dilutions of vector (250 μL/well) in Optimem-CaCl₂ for an hour at room temperature (RT). Cells were washed with α-MEM medium and were incubated overnight (O/N) at 37° C. and in 5% CO₂. Thereafter, the medium was removed and the cells were lysed using M-PER Mammalian Protein Extraction Reagent (100 μL/well) for 10 min at RT. Thereafter, 100 μL of SteadyGlo Reagent (Promega E2520) was added. Following shaking at RT for 10 min, bioluminescence was measured in a Glomax Biorad luminometer. The SV_PD1WT vector was titered in parallel to Sindbis virus vector expressing GFP (Sindbis-GFP) to establish a correlation between the visual titer (GFP positive cells) and the Luminescent signal. Vector titers refer to the number of infectious particles, transducing units (TU), per milliliter of supernatant (TU/mL). In this study the SV_PD-1WT vector was used at titer of $5-10^5$ TU/ml.

In Vivo Studies Using the SV PD-1WT Vector

All experiments were performed in accordance with the Institute of Animal Care and Use Committee at New York University Health.

Figure 3:
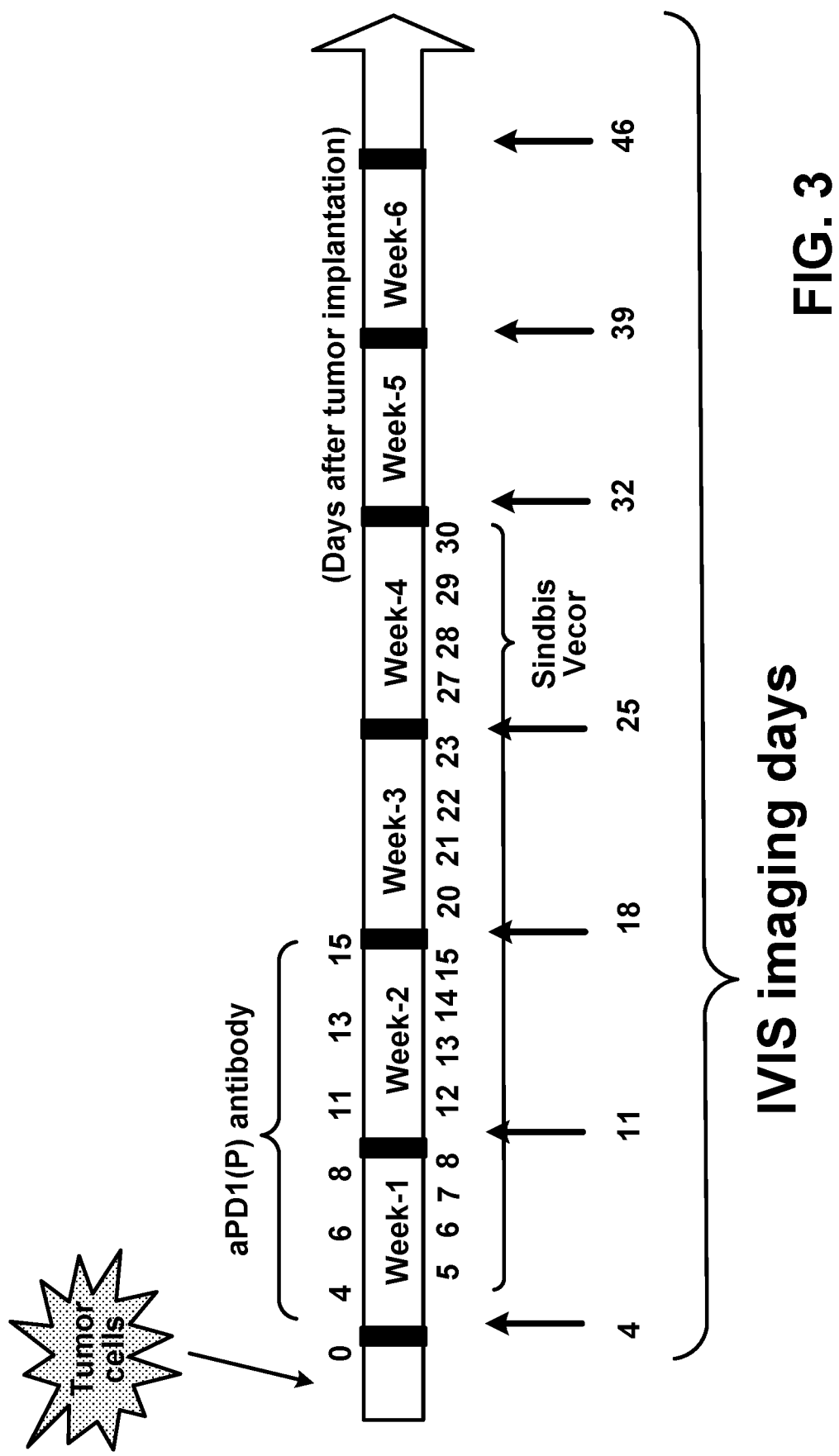
FIG. 3: presents a schematic depiction of the design of the in vivo experiments described herein. For animals that received treatment with the immune checkpoint inhibitor, anti-PD-1 antibody, (aPD-1), the mice were dosed at days 4, 6, 8, 11, 13, 15; as shown the diagram. For animals that received treatment with the SV vector, SV_PD-1WT, Sindbis virus vector treatment was administered to the animals 4 times a week for 4 weeks, at days 5, 6, 7, 8 (week 1); 12, 13, 14, 15 (week 2); 20, 21, 22, 23 (week 3) and 27, 28, 29, 30 (week 4), as indicated. Tumor growth analysis was performed once a week bioluminescence was measured in the mice using IVIS at days 4, 11, 18, 25, 32, 39 and 46.

Four to eight week old female BALB/c mice were purchased from Taconic (Germantown, NY). For the animal tumor model, $7\times10^4$ CT26.Fluc.NYESO1 cells in 500 μL OPTI-MEM medium were injected (i.p. administration) into animals 5 days before treatment with the Sindbis vector (SV_PD-1WT), (day 0). Four days after the cells were injected, tumor implantation in mice was assessed by IVIS imaging, and mice in the group receiving anti-PD-1 antibody received a first dose (250 μg/mouse) of anti-PD-1 antibody (clone RPMI-14, BioXCell) via i.p. injection. Anti-PD-1 antibody was administrated 3 days a week for a total of 2 weeks: days 4, 6, 8 and 11, 13 15 after tumor cell implantation. For treatments, $10^5$ TU of SV_PD-1WT vector in a total volume of 500 μL was injected into mice (i.p.) 4 days a week for a total of 4 weeks. Days after cells inoculation: 5, 6, 7, 8 (week one); 12, 13, 14, 15 (week 2); 20, 21, 22, 23 (week 3); and 27, 28, 29, 30 (week 4). The schematic diagram of the experiment design is shown in FIG. 3. The therapeutic efficacy of the treatment was monitored in two ways: by tumor luminescence and by animal survival.

Figure 4:
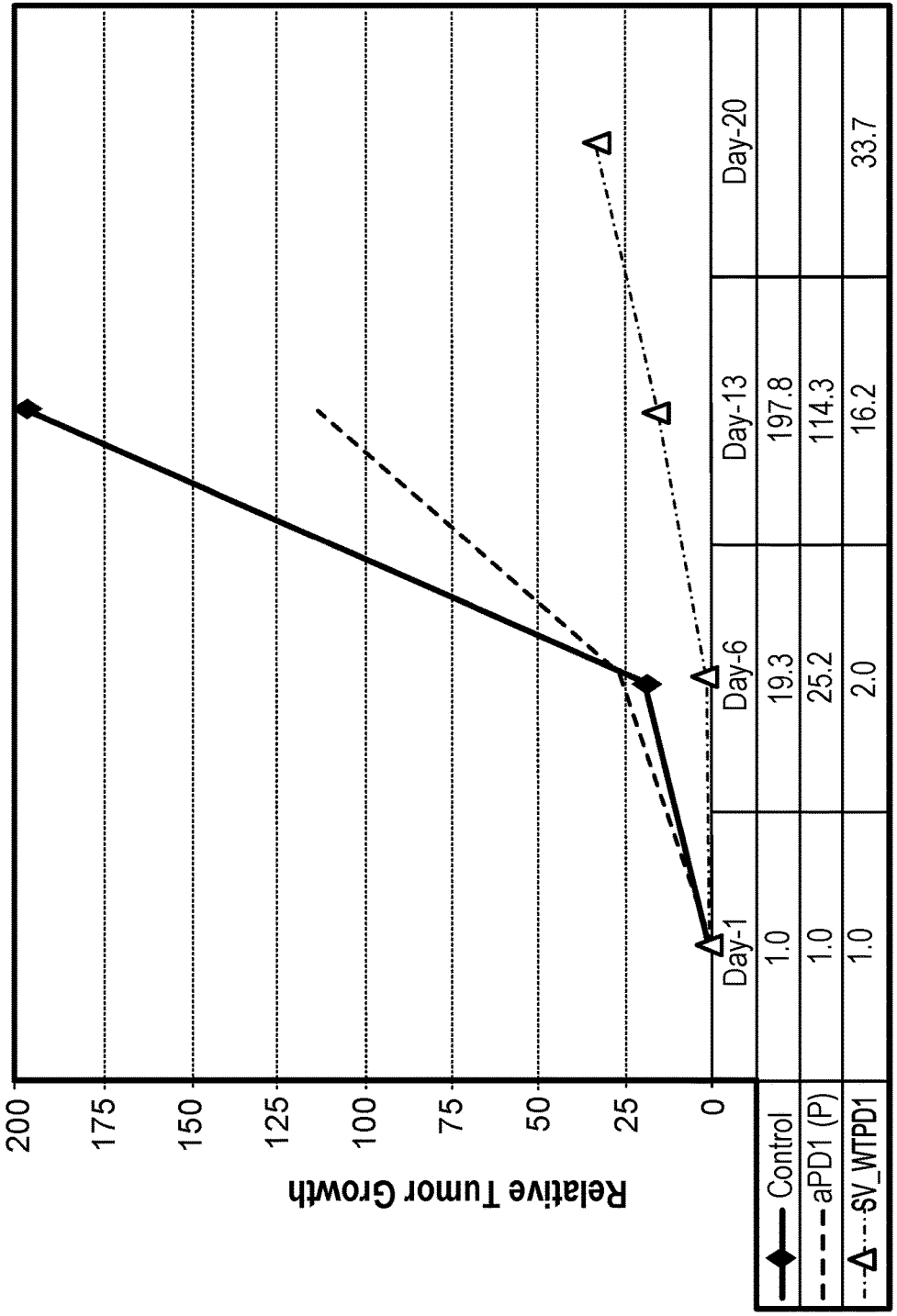
FIG. 4 presents graphs of tumor growth curves of mice treated with SV_PD-1WT Sindbis vector and of untreated (control) mice. Tumor growth is shown as fold changes relative to bioluminescence on the day before treatment of the same mouse with the Sindbis virus vector: (day–1/day–1); (day 6/day–1); (day 13/day–1) and (day 20/day–1). Each time point shows the tumor growth average of the 5 mice in each group. Day 13 is the last day, with 5 mice/group for control (untreated) and PD1 antibody treated groups.
Figure 5:
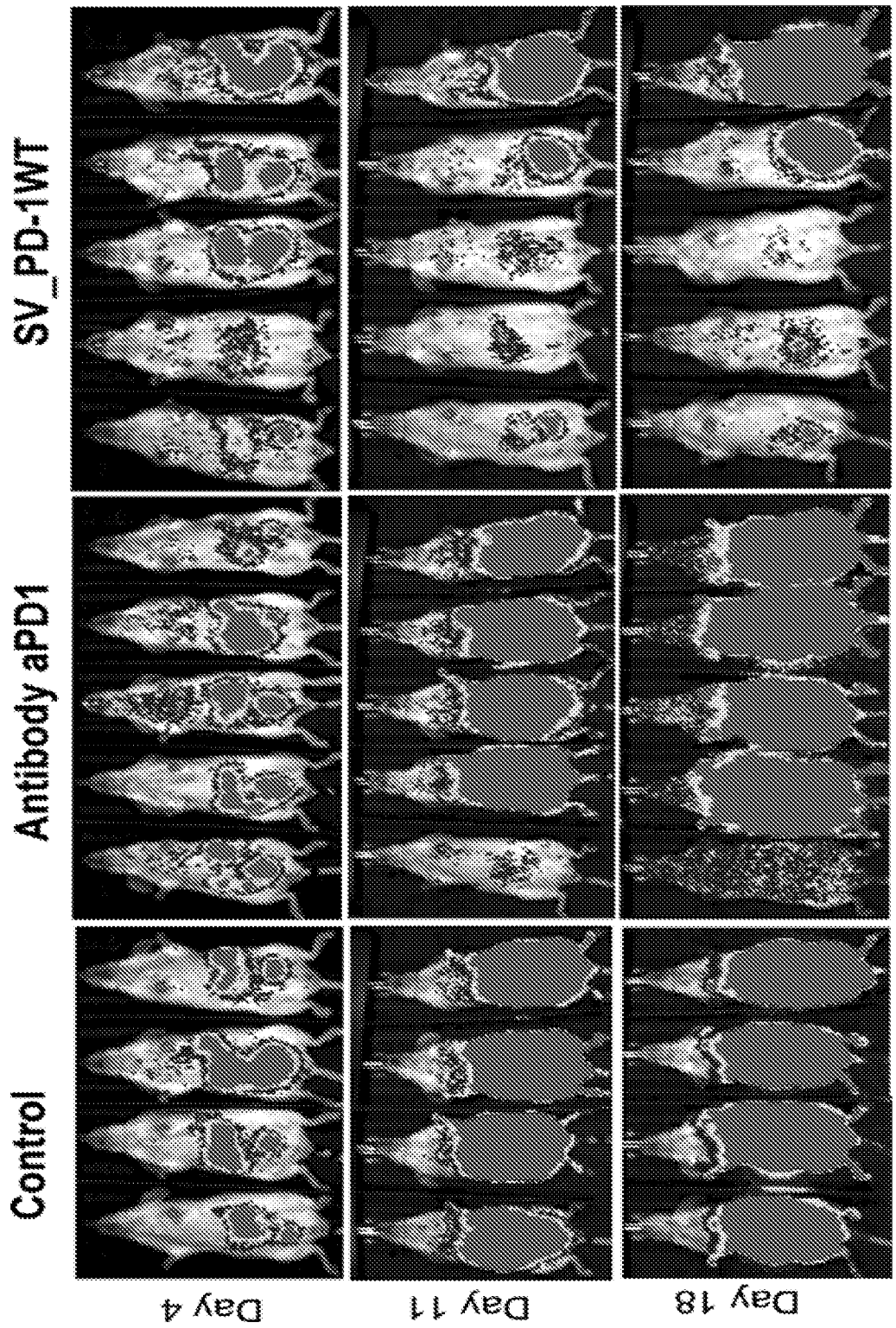
FIG. 5 shows representative bioluminescence images of control mice, anti-PD1 antibody-treated mice and SV_PD-1WT vector-treated mice bearing CT26.Fluc.NYESO1 tumors. Images correspond to days 4, 11 and 18 after tumor inoculation. Image scale min=50 Max=150 counts.
Figure 6:
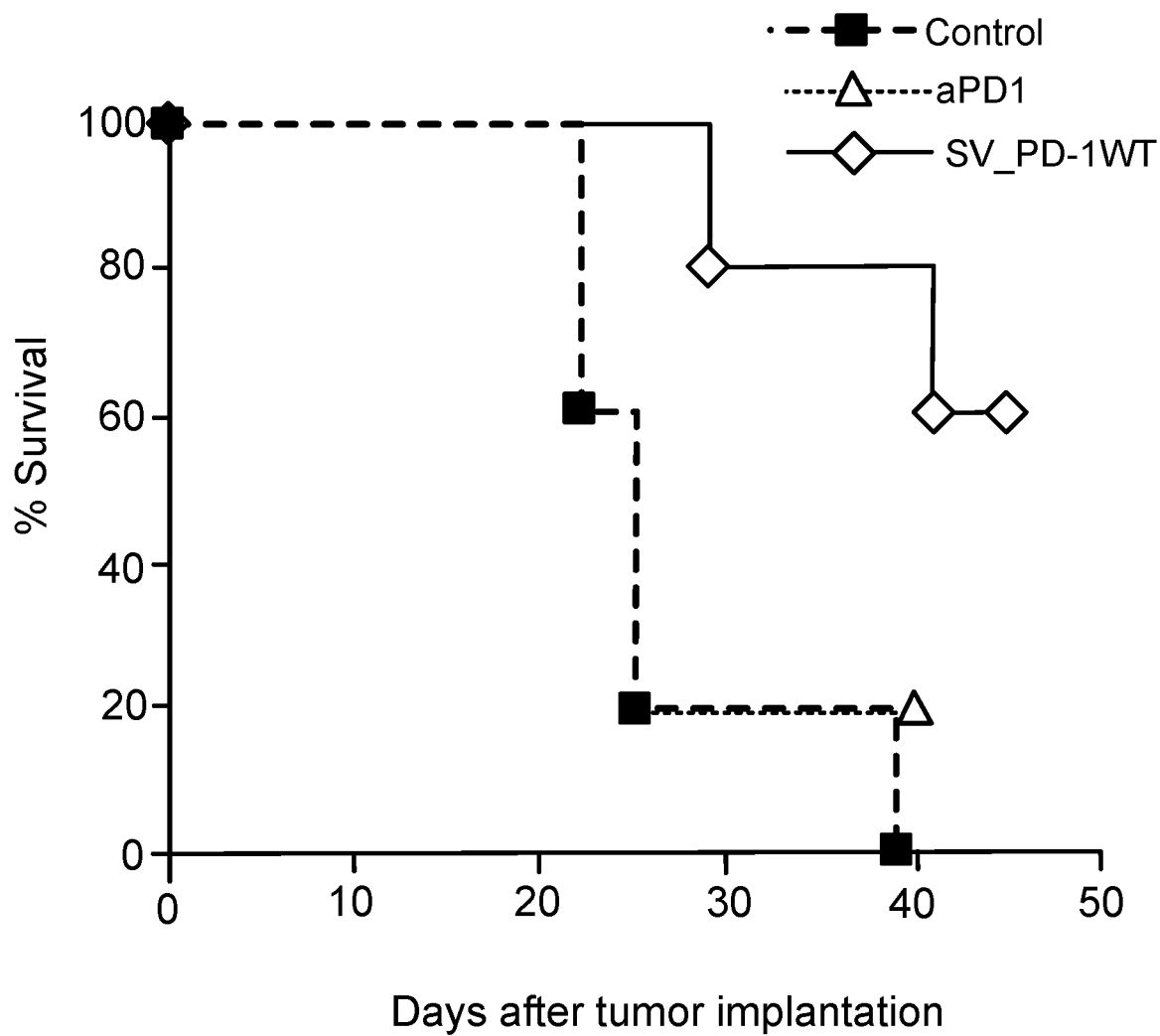
FIG. 6 shows survival curves of untreated Control animals (n=5), animals treated with anti-PD-1 antibody, (aPD1), (n=5) and animals treated with the Sindbis virus vector SV_PD-1WT, (n=5).

Noninvasive bioluminescent imaging was performed using the IVIS Spectrum imaging system (Caliper Life Science) and tumor growth was quantified using the Living Image 3.0 software (Caliper Life Science). The first tumor bioluminescent image was collected on day 4 after tumor cell inoculation, and then imaging was continued weekly for 6 weeks. Relative tumor growth for each mouse was calculated by dividing total body counts on a given day by total body counts on the first day of IVIS imaging (at day 4). Graphs showing relative tumor growth (fold change) at different days after treatment are shown in FIG. 4. Representative bioluminescent images of control, anti-PD1 antibody treated and SV_PD-1WT vector-treated mice bearing established CT26.Fluc.NYESO1 tumors are shown in FIG. 5. Animal survival was monitored and recorded daily; survival plots of untreated and SV_PD-1WT treated mice are shown in FIG. 6.

Example 3—Sindbis Virus Vector Encoding the Immune Checkpoint Protein 4-1BB Ligand (4-1BBL)

(4-1BB ligand) is a transmembrane cytokine that is part of the tumor necrosis factor (TNF) ligand superfamily. 4-1BBL is a bidirectional signal transduction molecule that serves as a ligand for 4-1BB (alternatively called "tumor necrosis factor receptor superfamily member 9 (TNFRSF9), CD137, and "induced by lymphocyte activation" (ILA)), which is a costimulatory receptor/immune checkpoint molecule expressed by T cells. 4-1BBL and its receptor, 4-1BB (TNFRSF9), play a role in antigen presentation by cells of the immune system, e.g., dendritic cells, macrophages, APC, and in the generation of cytotoxic T cells. While the 4-1BB receptor (4-1BBR) is absent from resting T cells, its expression is rapidly induced in T cells upon antigenic stimulation. 4-1BB reactivates anergic T cells and promotes T cell proliferation. 4-1BBL is involved in generating an optimal response in CD8+ T cells. 4-1BBL is also expressed by carcinoma cell lines and is thought to be involved in T cell-tumor cell interaction. 4-1BBL is expressed as a transmembrane surface protein on activated B cells, macrophages, dendritic cells, activated T cells, neurons and astrocytes.

The interaction of 4-1BBL with its receptor on activated T cells and natural killer (NK) cells promotes the upregulation of anti-apoptotic molecules, proliferation and IL-2 production. Both 4-1BB ligand and agonist 4-1BB receptor antibodies have been shown to have anti-tumor effects in preclinical mouse models (Melero, I. et al., 1997, *Nature Medicine*, 3:682-685).

The full-length murine 4-1BBL cDNA sequence (shown supra) was excised from MG50067-UT plasmid DNA (Sino Biological Inc., Wayne, PA) using HindIII and XbaI restriction enzymes. The cDNA fragment was purified by agarose gel electrophoresis. An XbaI-HindIII linker adaptor was ligated to the 5' end of the agarose gel purified fragment, and an XbaI-ApaI linker adapter was ligated to the 3' end. The fragment containing the 5' and 3' end linkers was then ligated into pT7-StuIR Sindbis virus vector (SV) digested with XbaI/ApaI, e.g., as described in Example 6 infra.

A cDNA polynucleotide encoding a soluble form of the 4-1BBL (s4-1BBL) polypeptide, corresponding to amino acids 106-314 of the 4-1BBL amino acid sequence identified as NCBI Ref Seq NP_033430.1, presented supra, was cloned into the pT7-StuIR SV vector. The s4-1BBL sequence lacked the transmembrane and cytoplasmic domains. The s4-1BBL amino acid sequence is as shown below:

(SEQ ID NO: 21)
MRTEPRPALTITTSPNLGTRENNADQVTPVSHIGCPNTTQQGSPVFAKLL

AKNQASLCNTTLNWHSQDGAGSSYLSQGLRYEEDKKELVVDSPGLYYVFL

ELKLSPTFTNTGHKVQGWVSLVLQAKPQVDDFDNLALTVELFPCSMENKL

VDRSWSQLLLLKAGHRLSVGLRAYLHGAQDAYRDWELSYPNTTSFGLFLV

KPDNPWE.

The cDNA polynucleotide sequence encoding s4-1BBL is as shown below:

```
                                         (SEQ ID NO: 22)
gccaccatgcgcaccgagcctcggccagcgctcacaatcaccacctcgcc caacctgggtacccgagagaataatgcagaccaggtcaccoctgtttccc acattggctgccccaacactacacaacagggctctcctgtgttcgccaag ctactggctaaaaaccaagcatcgttgtgcaatacaactctgaactggca cagccaagatggagctgggagctcatacctatctcaaggtctgaggtacg aagaagacaaaaaggagttggtggtagacagtcccgggctctactacgta tttttggaactgaagctcagtccaacattcacaaacacaggccacaaggt gcagggctgggtctctcttgttttgcaagcaaagcctcaggtagatgact ttgacaacttggccctgacagtggaactgttcccttgctccatggagaac aagttagtggaccgttcctggagtcaactgttgctcctgaaggctggcca ccgcctcagtgtgggtctgagggcttatctgcatggagcccaggatgcat acagagactgggagctgtcttatcccaacaccaccagctttggactattc ttgtgaaacccgacaacccatgggaatga.
```

The s4-1BBL sequence was synthesized by GenArt (Invitrogen GenArt Gene Synthesis, Lifetechnologies.com, ThermoFisher Scientific, Waltham, MA). A 5' XbaI site and a 3' ApaI were included to facilitate subcloning from the GenArt pMK vector into the SV vector (PT7-StuIR SV vector). The synthesized sequence was excised from the pMK plasmid using the restriction enzymes XbaI and ApaI.

In some cases, a secretory signal sequence was ligated to the amino (N) terminus of the polypeptide, e.g., the 4-1BBL, to optimize the synthesis of the soluble ligand. A non-limiting secretory signal sequence that is suitable for use can be obtained from IgK and has the amino acid sequence METDTLLLWVLLLWVPGSTGD (NCBI Accession No. NCBI:AAH80787.1), (SEQ ID NO: 23)

In some cases, a trimerization domain was also added to the carboxy (C) terminus of the polypeptide to increase the affinity of the soluble ligand for the 4-1BB receptor. An example of a trimerization domain that is suitable for use has the amino sequence IKQIEDKIEEILSKIYHIENE-IARIKKL (SEQ ID NO: 24). This sequence is an isoleucine zipper from the yeast protein GCN4 (Morris, N. P. et al., 2007, *Mol. Immunol.*, 44:3112-3121).

Example 4—Sindbis Virus Vector Encoding the Immune Checkpoint Protein OX40 Ligand (OX40L)

OX40 ligands (OX40Ls) are expressed on activated antigen presenting cells. The OX40 receptor is transiently expressed after antigen recognition by T cells. The interaction between OX40L and its receptor OX40 is important for survival of effector T cells and for the generation of memory T cells. In preclinical tumor models, OX40 agonists were shown to be effective in eradicating immunogenic tumors, though they were less effective in poorly immunogenic tumors (Sanmamed, M. F., 2015, *Seminars in Oncology*, 42:640-655).

Sindbis virus vectors were designed to contain a polynucleotide encoding the complete OX40L polypeptide; a soluble form of the OX40 ligand that contained an immunoglobulin Fc region, and an OX40 ligand coexpressed with a TAA.

The full-length murine OX40L cDNA sequence was excised from plasmid MG53582-UT (Sino Biological Inc.) using the restriction enzymes KpnI and XbaI. The cDNA fragment was purified using agarose gel electrophoresis. An XbaI-KpnI linker adaptor was ligated to the 5' end of the agarose gel purified fragment and an XbaI-ApaI linker adapter was ligated to the 3' end. The fragment containing the 5' and 3' end linkers was then ligated into pT7StuIR SV digested with XbaI/ApaI.

OX40L Polypeptide

A cDNA polynucleotide encoding the mouse OX40 ligand (OX40L) polypeptide amino acid sequence was cloned into the SV vector. The OX40L amino acid sequence identified by Accession No. NCBI P43488 is as shown below:

OX40L: NCBI P43488 Mouse Amino Acid Sequence

```
                                         (SEQ ID NO: 25)
MEGEGVQPLDENLENGSRPRFKWKKTLRLVVSGIKGAGMLLCFIYVCLQL

SSSPAKDPPIQRLRGAVTRCEDGQLFSSYKNEYQTMEVQNNSVVIKCDGL

YIIYLKGSFFQEVKIDLHFREDHNPISIPMLNDGRRIVFTVVASLAFKDK

VYLTVNAPDTLCEHLQINDGELIVVQLTPGYCAPEGSYHSTVNQVPL.
```

The cDNA polynucleotide sequence encoding OX40L identified by Accession No. NM_009452.2 is as shown below:

OX40L: NM_009452.2 Mouse cDNA Sequence

```
                                         (SEQ ID NO: 26)
atggaagggaaggggttcaaccoctggatgagaatctggaaaacggatc aaggccaagattcaagtggaagaagacgctaaggctggtggtctctggga tcaaggagcagggatgcttctgtgcttcatctatgtctgcctgcaactc tcttcctctccggcaaaggaccctccaatccaaagactcagaggagcagt taccagatgtgaggatgggcaactattcatcagctcatacaagaatgagt atcaaactatggaggtgcagaacaattcggttgtcatcaagtgcgatggg ctttatatcatctacctgaagggctccttttccaggaggtcaagattga ccttcatttcggagatcataatcccatctctattccaatgctgaacg atggtcgaaggattgtcttcactgtggtggcctctttggctttcaaagat aaagtttacctgactgtaaatgctcctgatactctctgcgaacacctcca gataaatgatgggagctgattgttgtccagctaacgcctggatactgtg ctcctgaaggatcttaccacagcactgtgaaccaagtaccactgtga.
```

Soluble Form of OX40L Containing an Immunoglobulin Fc Region (FcOX40L)

A DNA sequence encoding encodes a soluble form of the OX40L polypeptide was synthesized by GenArt (Lifetechnologies.com). More specifically, the sequence encodes a polypeptide (called FcOX40L herein) that comprises a secretory signal sequence (amino acids 1-18, from murine Ig heavy chain gamma-2A (NCBI: CAA49868.1), followed by the heavy chain constant (C_H) region of IgG2a (amino acids 19-250), a flexible spacer or linker amino acid sequence (amino acids 250-260) and the external (extracellular) region of the OX40L polypeptide (amino acids 260-405) of the NCBI sequence P43488, shown supra.

A 5' XbaI restriction enzyme site and a 3' ApaI restriction enzyme site were included to facilitate subcloning from the GenArt pMK vector into SV. The synthesized sequence was excised from the pMK plasmid using the restriction enzymes XbaI and ApaI. Shown below are the amino acid sequence and the cDNA polynucleotide sequence of FcOX40L. In the FcOX40L amino acid sequence shown below, the secretory signal sequence at the N-terminus of the amino acid sequence is in bold font; the IgG2a C_H region is underlined; the spacer sequence is in italic font; and the C-terminal OX40L external sequence is in regular font following the spacer sequence.

FcOX40L Amino Acid Sequence (SEQ ID NO: 27)
MGWSWIFLFLLSGTAGVHPRGPTIKPCPPCKCPAPNLLGGPSVFIFPPKI

KDVLMISLSPIVTCVVVDVSEDDPDVQISWFVNNVEVHTAQTQTHREDYN

STLRVVSALPIQHQDWMSGKEFKCKVNNKDLPAPIERTISKPKGSVRAPQ

VYVLPPPEEEMTKKQVTLTCMVTDFMPEDIYVEWTNNGKTELNYKNTEPV

LDSDGSYFMYSKLRVEKKNWVERNSYSCSVVHEGLHNHHTTKSFSRTPGK

*GGGSSGGGSGS*PAKDPPIQRLRGAVTRCEDGQLFISSYKNEYQTMEVQNN

SVVIKCDGLYITYLKGSFFQEVKIDLHFREDHNPISIPMLNDGRRIVFTV

VASLAFKDKVYLTVNAPDTLCEHLQNDGELIVVQLTPGYCAPEGSYHSTV

NQVPL.

In the FcOX40L-encoding cDNA sequence shown below, the secretory signal encoding polynucleotide sequence at the N-terminus is in bold font; the IgG2a C_H region-encoding sequence is underlined; the spacer/linker-encoding sequence is in italic font; and the C-terminal OX40L external region encoding sequence is in regular font following the sequence encoding the spacer/linker.

FcOX40L cDNA Sequence (SEQ ID NO: 28)
gccaccatgggctggtcctggatcttcctgttcctgctgtccggcaccgc cggcgtgcaccctcggggacccaccatcaagccctgcctccctgcaagt gtcccgctcccaacctgctgggcggccctccgtgttcatctttccaccc aagatcaaggacgtgctgatgatctccctgtctcccatcgtgacctgcgt ggtggtggacgtgtccgaggacgacccgacgtgcagatctcctggttcg tgaacaacgtggaggtgcacaccgcccagacccagacccaccgggaggac tacaactccaccctgcgggtggtgtccgccctgcccatccagcaccagga ctggatgtccggcaaggagttcaagtgcaaggtgaacaacaaggacctgc ccgcccccatcgagcggaccatctccaagcccaagggctccgtgcgggct ccccaggtgtacgtgctgcctcctcctgaggaggagatgaccaagaagca -continued ggtgaccctgacctgcatggtgaccgacttcatgcccgaggacatctacg tggagtggaccaacaacggcaagaccgagctgaactacaagaacaccgag cccgtgctggactccgacggctcctacttcatgtactccaagctgcgggt ggagaagaagaactgggtggagcggaactcctactcctgctccgtggtgc acgagggcctgcacaaccaccacaccaccaagtccttctcccggacccct ggcaag*ggaggaggctctagcggaggagggt*ctggatccctgccaagga ccctcccatccagcggctgcggggcgccgtgacccggtgcgaggacggcc agctgttcatctcctcctacaagaacgagtaccagaccatggaggtgcag aacaactccgtggtgatcaagtgcgacggcctgtacatcatctacctgaa gggctccttcttccaggaggtgaagatcgacctgcacttccgggaggacc acaacccatctccatccccatgctgaacgacggccggcggatcgtgttc accgtggtggcctccctggccttcaaggacaaggtgtacctgaccgtgaa cgctcccgacaccctgtgcgagcacctgcagaacgacggcgagctgatcg tggtgcagctgacacccggctactgcgctcccgagggctcctaccactcc accgtgaaccaggtgcccctgtga.

Example 5—Sindbis Virus Vector Encoding the Immune Checkpoint Protein 4-1BB Ligand (4-1BBL) or OX40 Ligand (OX40L) Reduced Tumor Size in In Vivo Mouse Models SV Vector Titers SV vector titers are determined by infecting BHK-SINLuc2 cells that express the Firefly luciferase under control of the Sindbis virus promoter, which allows a luciferase signal only in infected cells where Sindbis replicase is expressed. Briefly, $10^5$ BHKSINLuc2 cells in 12 well tissue culture plates were infected with 250 μl/well of the vector serial dilutions in Optimem-CaCl$_2$ for one hour at room temperature (RT). Cells were washed with α-MEM medium and were incubated overnight (O/N) at 37° C. and 5% CO$_2$. The medium was then removed, and the cells were lysed with M-PER Mammalian Protein Extraction Reagent (100 μl/well) for 10 minutes at RT. Thereafter, 100 μl of SteadyGlo Reagent (Promega E2520) was added; the culture plates were shaken for 10 minutes at RT; and bioluminescence was measured in a Glomax Biorad luminometer. SV vectors containing polynucleotides encoding the multimer polypeptides, e.g., checkpoint protein ligand and TAA, were titered in parallel to the SV vectors encoding GFP to establish a correlation between the visual titer (GFP positives cells) and the luminescent signal. SV vector titers refer to the number of infectious virus particles, transducing units, per milliliter of supernatant (TU/ml).

In Vivo Studies in Mice

All experiments were performed in accordance with the Institute of Animal Care and Use Committee, New York University Langone Health System.

Figure 7:
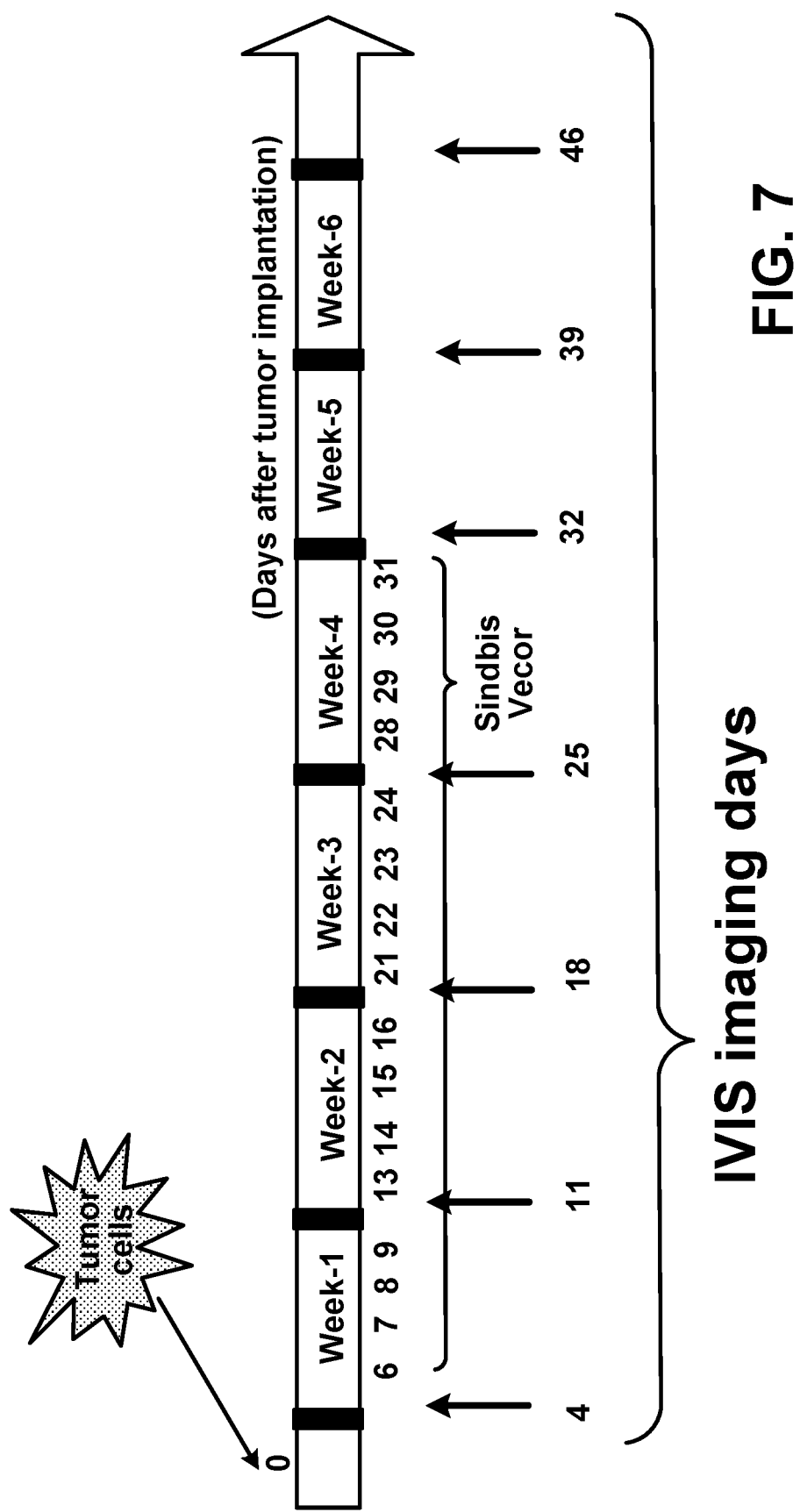
FIG. 7 shows a schematic depiction of the experimental design of the in vivo study described in Example 5. In accordance with the study, Sindbis virus vector treatments were administered to animals 4 times a week for 4 weeks at days: 6, 7, 8, 9 (week 1); days 13, 14, 15, 16 (week 2); days 21, 22, 23, 24 (week 3); and days 28, 29, 30, 31 (week 4) after tumor cell inoculation.

Four-to-eight week old female BALB/c mice were purchased from Taconic Biosciences (Germantown, NY). For the CT26 mouse solid tumor model (Lechner, M. et al., 2013, *J. Immunother.*, 36 (9):477-489), CT26.Fluc.NY-ESO1 cells ($7 \times 10^4$ cells in 500 μl OPTI-MEM medium) were injected into mice intraperitoneally (i.p.) 6 days before Sindbis virus vector treatment (day 0). Four days after cell injection, tumor implantation in mice was assessed by IVIS imaging. Six days after tumor inoculation, the first dose of $10^7$ TU of the appropriate Sindbis vector in a total volume of 500 µl was administered to the mice via i.p. injection. The treatment continued 4 days a week for a total of 4 weeks; days after cells inoculation: 6, 7, 8, 9 (Week one); 13, 14, 15, 16 (week 2); 21, 22, 23, 24 (week 3); and 28, 29, 30, 31 (Week 4). The experimental design of this study is shown in FIG. 7. The therapeutic efficacy of the treatment was monitored in two ways: tumor luminescence and survival.

Noninvasive bioluminescent imaging was performed using the IVIS Spectrum imaging system (Caliper Life Sciences/PerkinElmer, Hopkinton, MA), and tumor growth was quantified using the Living Image 3.0 software (Caliper Life Sciences/PerkinElmer). The first tumor bioluminescent image was obtained day 4 after inoculation of tumor cells, and then weekly thereafter for 6 weeks. Relative tumor growth for each mouse was calculated by dividing total body counts on a given day by total body counts on the first IVIS image at day 4.

The relative tumor growth curves at different days after treatment of animals with an anti-4-1BB antibody or with vector SV-4-1BBL (SV vector expressing 4-1BBL) alone or in combination with SV-NYESO1 (SV vector expressing NY-ESO-1) are shown in FIG. 8, which demonstrates an example of the antitumor efficacy of Sindbis virus vectors encoding checkpoint protein ligands and/or TAAs (called "armed" SV vectors herein) compared with an antibody directed against 4-1BB (an anti-4-1BB antibody), (Bio-X-Cell, West Lebanon, NH; InVivoMAb anti-mouse 4-1BB (CD137), Clone 3H3, Catalog #BE0239). As observed in FIG. 8, used alone, the anti-4-1BB antibody was not effective in reducing tumor growth in these in vivo mouse model studies. By contrast, the SV-4-1BBL vector expressing 4-1BBL demonstrated effectiveness in reducing tumor growth. Of note, use of the anti-4-1BB antibody and the SV-NY-ESO-1 vector expressing NY-ESO-1 TAA in combination, as well as use of the SV vector expressing NY-ESO-1 TAA (SV-NYESO1) and the SV vector expressing 4-1BBL (SV-4-1BBL) in combination were highly effective in reducing tumor growth over time.

In another study, treatment of animals with an anti-OX40L antibody ("aOX40L") alone was compared with treatments using (i) Sindbis virus vector harboring NY-ESO-1 TAA encoding polynucleotide (SV-NYESO1) alone and (ii) a combination of anti-OX40L antibody and (SV-NYESO1) together, versus controls (FIG. 9A). In another study, treatment of animals with (i) Sindbis virus vector harboring NY-ESO-1 TAA encoding polynucleotide (SV-NYESO1) alone; (ii) Sindbis virus vector harboring OX40L encoding polynucleotide (SV-OX40L) alone; and (iii) a combination of SV-NYESO1 and SV-OX40L together were compared versus controls (FIG. 9B). As is observed by comparing the results shown in FIG. 9B and FIG. 9A, treatment with SV-OX40L was more efficacious than treatment with anti-OX40L antibody (i.e., a higher percentage of animals survived longer following treatment with SV-OX40L versus treatment with anti-OX40L antibody (aOX40L). In addition, the combination treatment using SV-NYESO1 and SVOX40L conferred 100% survival to animals (FIG. 9B), a result which is superior to the combination treatment using anti-OX40L antibody and SV-NYESO1 together (FIG. 9A). These results support the use of "armed" Sindbis virus vectors, which provide superior and more effective treatment compared with the use of antibody-mediated therapy.

Example 6—General Protocols for Sindbis Virus Vector Preparation

Construction of recombinant vectors, particularly for the studies described in Example 5 supra, were performed using standard molecular biology techniques, including plasmid growth and purification, restriction endonuclease digestion, agarose gel electrophoresis and fragment extraction, ligation, transformation, polymerase chain reaction (PCR) methods and DNA sequencing, as described in Current Protocols in Molecular Biology, E M. Ausubel et al. (Eds), John Wiley and Sons, Inc., NY, USA. (1998) and Molecular Cloning: A Laboratory Manual (2nd Ed.), J. Sambrook, E. F. Fritsch and T. Maniatis (Eds), Cold Spring Harbor Laboratory Press, NY, USA. (1989).

Figure 10:
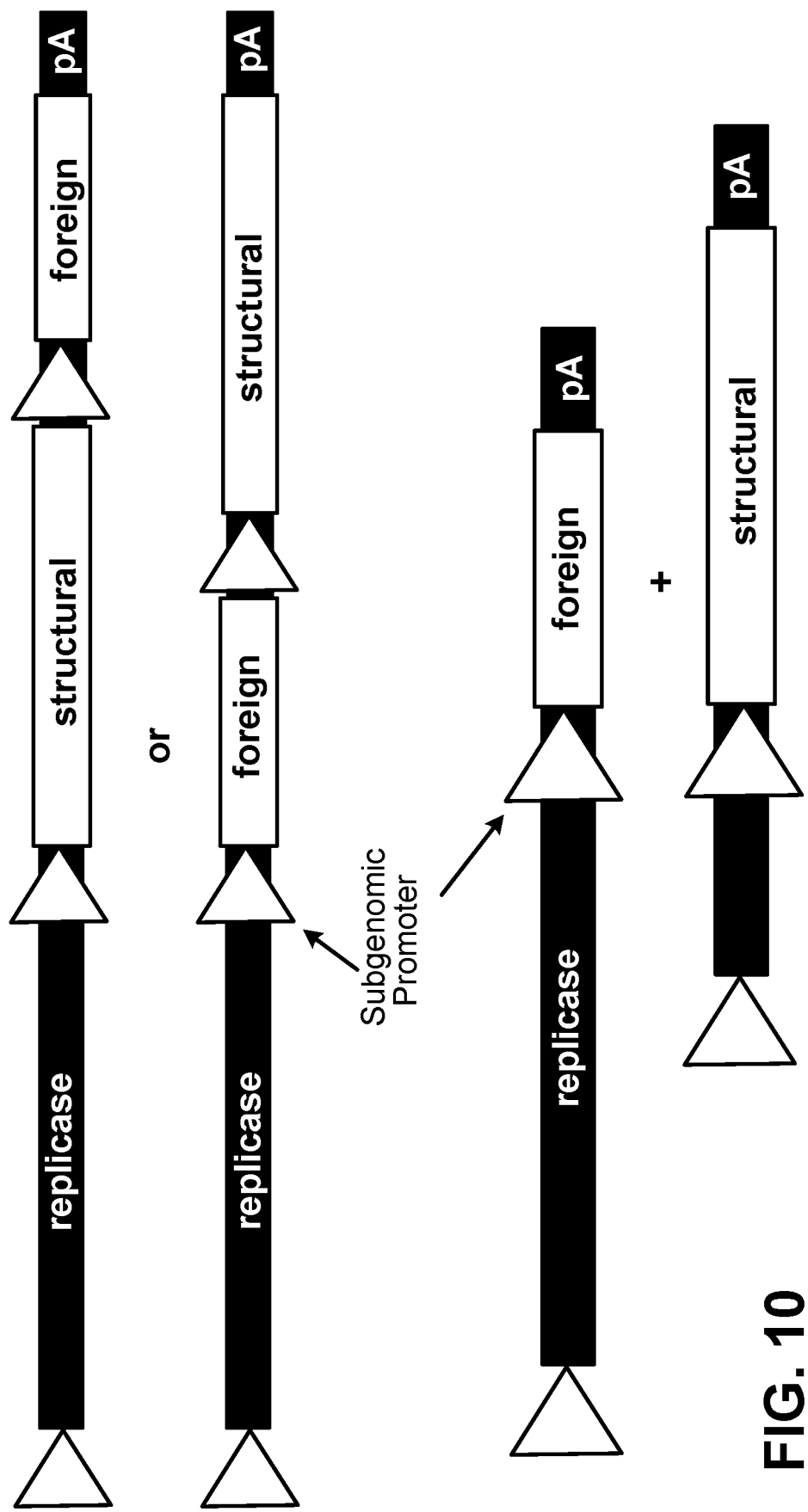
FIG. 10 presents a schematic depiction illustrating that a Sindbis virus vector is typically capable of expressing two full sized genes, one from each subgenomic promoter.

Unless otherwise described, sequences were ligated into the 5' XbaI site and the 3' ApaI site of the pT7StuIR-LacZ vector, in which the LacZ sequence was removed. If cDNA sequences contained XbaI or ApaI restriction sites, these sites were mutated to remove them, while maintaining the native amino acid sequence. A schematic depiction of a Sindbis virus vector capable of expressing heterologous gene, e.g., a checkpoint molecule-encoding gene or a TAA-encoding gene, from each of its two subgenomic promoters is shown in FIG. 10. Plasmid DNAs, isolated from bacterial colonies obtained following transformation with the ligation reactions, were analyzed by restriction digestion and positive plasmids were sequenced.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A therapeutic composition comprising a Sindbis virus encoding an immune checkpoint protein or a cognate ligand binding portion thereof fused to an immunoglobulin hinge region and an immunoglobulin heavy chain constant domain.

2. The therapeutic composition of claim 1, wherein the Sindbis virus encoding a fusion polypeptide comprises a secretory signal sequence linked to the immunoglobulin heavy chain constant domain, which is linked to the immune checkpoint protein, or an extracellular domain thereof; and wherein the fusion protein comprises one or more linker sequences.

3. The therapeutic composition of claim 1, wherein the fusion protein comprises a linker sequence between the hinge region and the immunoglobulin heavy chain constant domain.

4. The therapeutic composition of claim 1, wherein the immunoglobulin is IgG, IgG1, or IgG2a.

5. The therapeutic composition of claim 4, wherein the heavy chain constant domain is the CH3 domain.

6. The therapeutic composition of claim 2, wherein the linker sequence comprises the sequence GGGSSGGGSGG (SEQ ID NO: 1) or GGGSSGGGSGS (SEQ ID NO: 2).

7. The therapeutic composition of claim 2, wherein the secretory signal sequence comprises the amino acid sequence METDTLLLWVLLLWVPGSTGD (SEQ ID NO: 23).

8. The therapeutic composition claim 1, wherein the immune checkpoint protein is selected from the group consisting of PD-1, PD-LI, OX40, OX40L, CTLA-4, 4-1BB, 4-1BBL, KIR, LAG-3, IDOI, TIM-3, A2AR, B7-H3, B7-H4, B7-1/87-2, BTLA and VISTA, or a cognate ligand binding portion thereof.

9. The therapeutic composition of claim 1, wherein the Sindbis virus further encodes a tumor associated antigen (TAA) or an epitope of the TAA.

10. The therapeutic composition of claim 9, wherein the TAA is NY-ESO-1.

11. The therapeutic composition of claim 2, wherein the fusion polypeptide encoded by Sindbis virus comprises soluble 4-1BBL and a carboxy (C) terminal trimerization domain.

12. The therapeutic composition of claim 11, wherein the trimerization domain has the amino sequence KQIEDKIEE-ILSKIYHIENEIARIKKL 25 (SEQ ID NO: 24).

* * * * *